(12) United States Patent
Hardin et al.

(10) Patent No.: US 7,211,414 B2
(45) Date of Patent: May 1, 2007

(54) ENZYMATIC NUCLEIC ACID SYNTHESIS: COMPOSITIONS AND METHODS FOR ALTERING MONOMER INCORPORATION FIDELITY

(75) Inventors: Susan H. Hardin, Bellaire, TX (US); Xiaolian Gao, Houston, TX (US); James Briggs, Katy, TX (US); Richard Willson, Houston, TX (US); Shiao-Chun Tu, Houston, TX (US)

(73) Assignee: Visigen Biotechnologies, Inc., Houston, TX (US)

(*) Notice: Subject to any disclaimer, the term of this patent is extended or adjusted under 35 U.S.C. 154(b) by 76 days.

(21) Appl. No.: 10/007,621

(22) Filed: Dec. 3, 2001

(65) Prior Publication Data
US 2003/0134807 A1 Jul. 17, 2003

(51) Int. Cl.
C12P 19/34 (2006.01)
C12Q 1/68 (2006.01)
A01N 43/04 (2006.01)
C07H 21/04 (2006.01)

(52) U.S. Cl. .................. 435/91.1; 435/6; 536/23.1; 514/44

(58) Field of Classification Search .......... 435/6, 435/91.1; 514/44; 536/23.1
See application file for complete search history.

(56) References Cited

U.S. PATENT DOCUMENTS 5,512,462 A 4/1996 Cheng .................. 435/91.2

6,399,335 B1 * 6/2002 Kao et al. .................. 435/91.1

FOREIGN PATENT DOCUMENTS

| WO | WO 98/22615 | 5/1998 |
|---|---|---|
| WO | WO 99/05315 | 2/1999 |
| WO | WO 99/53034 | 10/1999 |
| WO | WO 00/06770 | 2/2000 |
| WO | WO 00 36151 A | 6/2000 |
| WO | WO 00 36152 A | 6/2000 |
| WO | WO 00/60114 | 10/2000 |
| WO | WO 00/67698 A3 | 11/2000 |
| WO | WO 00 70073 A | 11/2000 |
| WO | WO 67698 A2 | 11/2000 |
| WO | W0 1/23610 A2 | 4/2001 |
| WO | WO 01/25480 A2 | 4/2001 |
| WO | WO 02/04680 A2 | 1/2002 |

OTHER PUBLICATIONS

Sanger, et al. *DNA sequencing with chain-terminating inhibitors.* Proc. natl. Acad Sci USA, vol. 74, No. 12, pp. 5463-5467, Dec. 1977.
Church, et.al. *Multiplex DNA Sequencing*, Science, New Series, vol. 240, Issue 4849(Apr. 8, 1988), 185-88.
Hunkapiller, et al. *Large-Scale and Automated DNA Sequence Determination.* Science, New Series, vol. 254, Issue 5028, Special Issue: Instrumentation (Oct. 4, 1991), 59-67.

(Continued)

*Primary Examiner*—Jezia Riley
(74) *Attorney, Agent, or Firm*—Robert W Strozier

(57) ABSTRACT

Nucleotide triphosphate probes containing a molecular and/or atomic tag on a a γ and/or β phosphate group and/or a base moiety having a detectable property are disclosed, and kits and method for using the tagged nucleotides in sequencing reactions and various assay. Also, phosphate and polyphosphate molecular fidelity altering agents are disclosed.

31 Claims, 14 Drawing Sheets

OTHER PUBLICATIONS

Maxam, et. al. *A new methods for sequencing DNA.* Proc. Natl. Acad. Sci. USA vol. 74, No. 2, pp. 560-564, Feb. 1977.

Fleischmann, et.al., *Whole-Genome Random Sequencing and Assembly of Haemophilus influenzae* Rd. Science, New Series, vol. 269, Issue 5223 (Jul. 28, 1995), 496-498+507-512.

Velculescu, et. al. Serial Analysis of Gene Expression. *Science,* New Series, vol. 270, Issue 5235 (Oct. 20, 1995), 484-487.

Koster, et. al. *A strategy for rapid and efficient DNA sequencing by mass spectrometry.* Nature Biotechnology vol. 14, Sep. 19961123-1128.

Jett, et. al. *High-Speed DNA Sequencing: An Approach Based Upon Fluorescence Detection of Single Molecules.* J. Biomol. Struct. Dyn. vol. 7, pp. 301-, 1989.

Garcia. *Determination of Ion Permeability by Fluorescence Quenching.* Methods in Enzymology, vol. 207., pp. 501-511,1992.

Yanlong, et. al. *Design, Synthesis, and Spectroscopic Properties of Peptide-Bridged Fluorescence Energy-Transfer Cassettes.* Bioconjugate Chem., vol. 10, pp. 241-245, 1999.

Tabor, et. al. *DNA Sequence Analysis with a Modified Baceteriophage T7 DNA Polymerase.* Journal of Biological Chemistry, vol. 265, pp. 8322-8328, 1990.

Nyren. *Enzymatic Methods for Continuous Monitoring of DNA Polymerase Activity.* Analytical Biochemistry 167, 235-238, 1987.

Johnson, et. al. *An Enzymatic Method for Determination of Inorganic Pyrophosphate and Its Use as an Assay for RNA Polymerase.* Analytical Biochemistry vol. 26, 137-145, 1968.

Driscoll, et. al. *Atomic-scale imaging of DNA Using Scanning Tunnelling Microscopy.* Nature, vol. 346, pp. 294-296, 1990.

Bains, et. al. *A Novel Method for Nucleic Acid Sequence Determination.* J. Theor. Biol., vol. 135, pp. 303-307, 1988.

Syvanen, et. al. *A Primer-Guided Nucleotide Incorporation Assay in the Genotyping of Apolipoprotein E.* Genomics, vol. 8, 684-692, 1990.

Wainberg, et. al. *Enhanced Fidelity of 3TC-Selected Mutant HIV-1 Reverse Transcriptase.* Science, New Series, vol. 271, pp. 1282-1285. 1996.

Lewis, et. al. *Uniquely Altered DNA Replication Fidelity Conferred by an Amino Acid Change in the Nucleotide Binding Pocket of Human Immunodeficeincy Virus Type 1 Reverse Transcriptase.* Journal of Biological Chemistry vol. 274, pp. 32924-32930, 1999.

Narasimhan, et. al. *p-Benzoquinone activation of metal oxide electrodes for attachment of enzymes.* Enzyme Microb. Technol., vol. 7, pp. 283-286, 1985.

Asanov, et. al. Regenerable Biosensor Platform: A Total Internal Reflection Fluorescence Cell with Electrochemical Control. Analytical Chemistry, vol. 70, pp. 1156-1163, 1998.

Tokunaga, et. al. *Single Molecule Imaging of Fluorophores and Enzymatice Reactions Achieved by Objective-Type Total Internal Reflection Fluorescence Microscopy.* Biochemical and Biophysical Research Communications vo. 235, pp. 47-53, 1997.

Xu, et. al. Long-Range *Electrostatic Trapping of Single-Protein Molecules at a Liquid-Solid Interface.* Science, vol. 281, pp. 1650-1653, 1998.

Edman, et. al. *Conformational transitions monitored for single molecules in solution.* Proc. Natl. Acad. Sci. USA, pp. 6710-6715, 1996.

Kinjo, et. al. *Ultrasensitive hybridization analysis using fluorescence correlation spectroscopy.* Nucleic Acids Research, vo. 23, 1795-1799, 1995.

Castro, et. al. *Single-Molecule Detection of Specific Nucleic Acid Sequences in Unamplified Genomic DNA.* Analytical Chemistry, vol. 69, pp. 3915-3920, 1997.

Nie, et. al., *Probing Individual Molecules with Confocal Fluorescence Microscopy.* Science, vol. 266, pp. 1018-1021, 1994.

Nie, et. al. *Real-Time Detection of Single Molecules in Solution by Confocal Fluorescence Microscopy. Analytical Chemistry,* vol. 67, pp. 2849-2857, 1995.

Schimidt, et. al. *Imaging of single molecule diffusion.* Proc. Natl. Acad. Sci. USA vol. 93, pp. 2926-2929, Apr. 1996.

Zuckerman, et. al. *Efficient Methods for attachment of thiol specefic probes to the 3'ends of synthetic . . .* Nucleic Acids Research vol. 15, pp. 5305-5321, 1987.

Gupta, et. al. *A general method for the synthesis of 3'-sulfhydryl and phosphate group containing oligonucleotides.* Nucleic Acids Research, vol. 19, pp. 3019-3025,1991.

Agrawal, et. al. *Site-Specific Functionalization of Oligodeoxynucleotides For Non-Radioactive Labelling.* Tetrahedron Letters, vol. 31, pp. 1543-1546, 1990.

Sproat, et. al. *The synthesis of protected 5'-mercapto-2',5'-dideoxyribonucleoside-3'-O-phosphoramidites; uses of 5'-mercapto-oligodeoxyribonucleotides.* Nucleic Acids Research, vol. 15, pp. 4837-4849.

Nelson, et. al. *Multifunctional oligonucleotide probes synthesized using a novel CPG support are able to detect single base pair mutations.* Nucleic Acids Research, vol. 17, pp. 7187-7193, 1989.

LeBel, et. al. *Characterization and Purification of a Calcium-sensitive ATP Diphosphohydrolase from Pig Pancreas.* Journal of Biological Chemistry, vol. 255, pp. 1227-1233, 1980.

Guatelli, et. al. *Isothermal, in vitro amplification of nucleic acids by a mutltienzyme reaction modeled after retroviral replication.* Proc. Natl. Acad. Sci. USA, vol. 87, pp. 1874-1878. 1990.

Fu, et al. *Sequencing double-stranded DNA by strand displacement.* Nucleic Acids Research, vol. 25 pp. 677-679, 1977.

Biotechniques 20: 1004-1010 ( Jun. 1996) *Modulation of nontemplated Nucleotide Addition by Tag DNA Polymerase Primer Modifications that Facilitate Genotyping.*

Osheroff, et. al. *The Fidelity of DNA Polymerase b During Distributive and Processive DNA Synthesis.* Journal of Biological Chemistry, vo. 274, Feb. 5, pp. 3642-3650, 1999.

Kim, et al. New Human Immunodeficiency Virus, Type I Reverse Transcriptase (HIV-IRT) Mutants with Increased Fidelity of DNA Synthesis. Journal of Biological Chemistry vol. 274, pp. 27666-2773, 1999.

Jones, et. al. *An Iterative and Regenerative Method for DNA Sequencing.* Biotechniques vol. 22, pp. 938-946, 1997.

Hultman, et al. *Direct solid phase sequencing of genomic and plasmid DNA using magnetic beads as solid support,* Nucleic Acis Research, vol. 17, pp. 4937-4946. 1988.

PCT International Search Report.

Yarbrough, LR. Synthesis and properties of a new fluorescent analog of ATP: Biochemical and Biophysical Research Communications. United States. Mar. 15, 1978 vol. 81, No. 1; pp. 35-41. (XP009007956).

Wu Fy-H, et. al. Synthesis and Properties of Adenosine-5 . . . Archives of Biochemistry and Biophysics vol. 246, No. 2, May 1, 1986 pp. 564-571, (XP009006405).

Schlageck, JG, et. al. "Spectroscopic Techniques for Study of Phospho DI Ester Bond Formation By *Excherichia-coli* RNA Polymerase". Journal of Biological Chemistry, vol. 254, No. 23, 1979, pp. 12074-12077, (XP002235051).

Eigen M: "The Fifth Paul Ehrlich Lecture Virus Strains As Models of Molecular Evolution" Medicinal Research Reviews, New York, NY US. vol. 13, No. 4, Jul. 1993, pp. 385-398 (XP000430626).

Arion D, et. al.: "HIV Resistance To Zidovudine: The Role of Pyrophosphorolysis" Drug Resistance Updates, vol. 2, No. 2, Apr. 1999, pp. 91-95, (XP009008252).

Ronaghi M, et. al. "Real-Time DNA Sequencing Using Detection of Pyrosphosphate Release" Analytical Biochemistry, vol. 242, Nov. 1, 1996 pp. 84-89, (XP002055379).

Kunkel, TA: "DNA Replcation Fidelity." Journal of Biological Chemistry, vol. 267, No. 26, 1992, pp. 18251-18254, (XP002235051).

Yarbrough, LR, et. al. "Synthesis and Properties of Fluorescent Nucleotide Substrates For DNA Dependent RNA Polymerases" Journal of Biological Chemistry, vol. 254, No. 23, 1979, pp. 12069-12073, (XP002235050).

Wong I, et. al. "An Induced-Fit Kinetic Mechanism for DNA Replication Fidelity Direct Measurement By Single-Turnover Kinetics" Biochemistry. vol. 30, No. 2, 19991, pp. 526-537, (XP002237615).

* cited by examiner

γ implies the presence of an ANS-tag attached at the dNTP
γ-phosphate

|  | | | | Pfu | | | | | | | | Taq | | |
|---|---|---|---|---|---|---|---|---|---|---|---|---|---|---|
| Enzyme | − | + | + | + | + | + | + | + | + | + | + | + | + | + |
| Primer (TOP) | + | + | + | + | + | + | + | + | + | + | + | + | + | + |
| Template | − | − | − | BOT-3TC | | | BOT-TC | | | BOT-Sau | | | BOT-3TC | |
| Nucleotide | − | dA | γA | − | dG | dA | γA | dG | dA | γA | dG | dA | γA | dA | γA |

γ implies presence of an ANS-tag attached via the
dNTP γ−phosphate

FIG. 5

γ implies presence of an ANS-tag attached via the dNTP γ-phosphate

γ implies presence of an ANS-tag attached via
the dNTP γ–phosphate

Primer sequence: 5' GGTACTAAGCGGCCGCATG 3'

Template sequence: 3' CCATGATTCGCCGGCGTACTGTTGCCAAATGTGACCCAAGGTT 5'

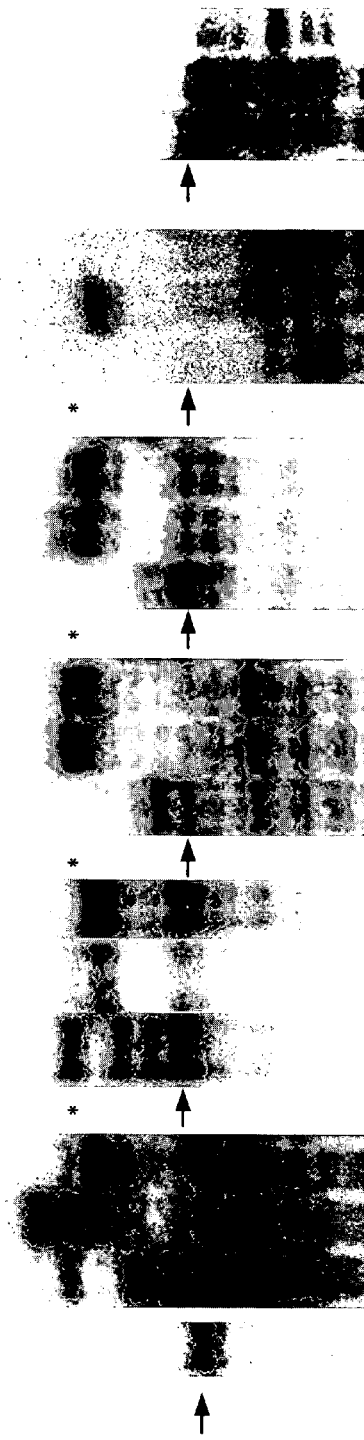

FIG. 12

Different Polymerases React Differently to the ANS-g-modified Nucleotides: primer extension reactions were performed to determine the ability of various polymerases to incorporate -tagged dNTPs during DNA polymerization.Control reactions contained natural dNTPs to monitor for template-directed nucleotide incorporation as well as for misincorporation. The reactions were performed in the appropriate buffer and contained the specified polymerase, primer/template duplex (radiolabeled 'TOP'primer annealed to 'BOT-3TC'template), and only the indicated dNTP. The reactions were carried out at room temperature or at 37C for 30 minutes and were stopped by the addition of 0.5mM EDTA. The volume of the reaction was then reduced to approximately 2-4l, loading dye was added and the polymerization products were electrophoresed through a 20% denaturing polyacrylamide gel.Arrows indicate the position of the free labeled 'TOP'. Asterisks indicate 3-base extension.

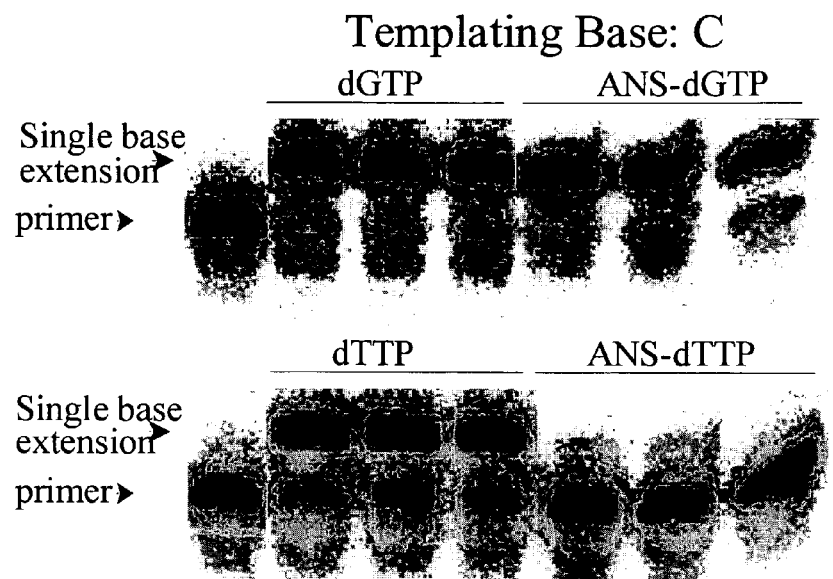
FIG. 14 TOP
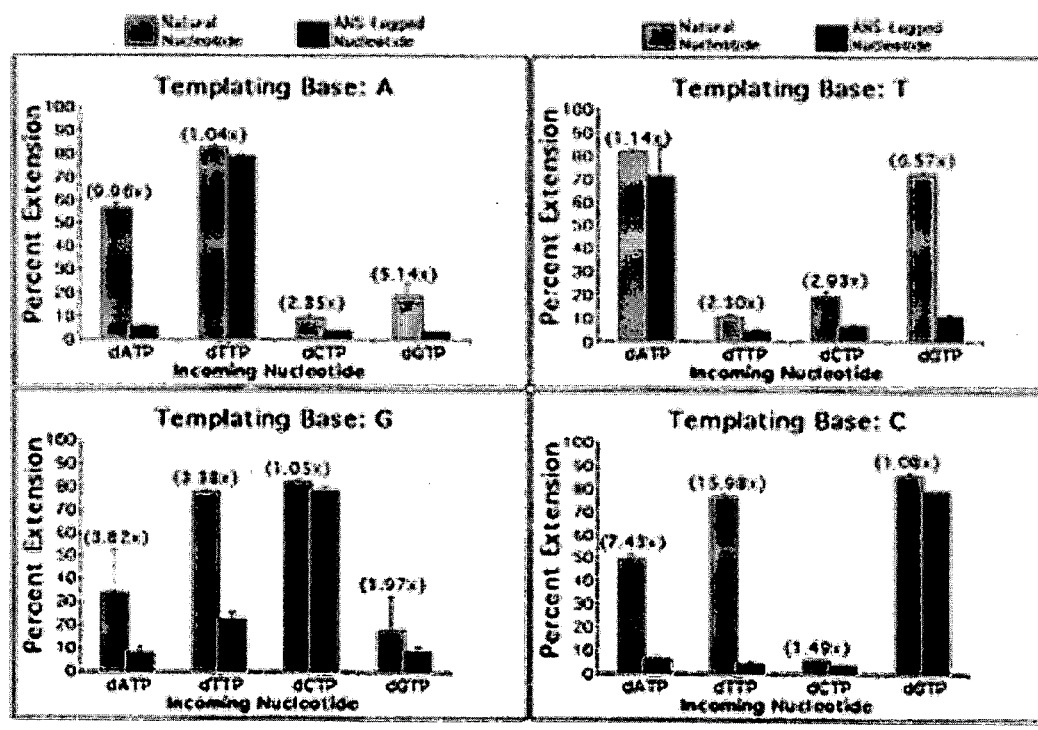
FIG. 14 BOTTOM

ENZYMATIC NUCLEIC ACID SYNTHESIS: COMPOSITIONS AND METHODS FOR ALTERING MONOMER INCORPORATION FIDELITY

BACKGROUND OF THE INVENTION

1. Field of the Invention

The present invention relates to compositions and methods for altering the fidelity of nucleic acid synthesis.

More particularly, the present invention relates to the following general areas: (1) nucleotide triphosphate monomers having at least one molecular or atomic tag bonded to and/or chemically and/or physically associated with one or more of the phosphate groups of the triphosphate moiety of the monomers, the base moiety, and/or the sugar moiety in the case of a nucleoside analog; (2) methods for enzymatic DNA synthesis with altered fidelity; (3) methods of sequencing DNA, based on the detection of base incorporation using tags bonded to and/or chemically and/or physically associated with the β and/or γ phosphates of the triphosphate of the nucleotide monomer, the base moiety of a nucleotide or nucleoside monomer, and/or the sugar moiety of a nucleotide or nucleoside monomer, the polymerase or by the release of the tagged pyrophosphate (PPi); (4) a template-mediated primer extension reaction with improved monomer incorporation fidelity using the tagged monomers; (5) methods for performing a primer extension reaction, such as a DNA sequencing reaction, or a polymerase chain reaction using the tagged monomers; (6) methods for improving nucleotide incorporation fidelity by adding tagged pyrophosphate ($PP_i$) to a monomer polymerization medium, where the monomers can be tagged or untagged; and (7) kits for conducting nucleotide sequencing, a polymerase chain reaction, a templated-mediated primer extension reaction or similar reaction with improved monomer incorporation fidelity using either tagged pyrophosphate and/or untagged or tagged monomers.

2. Description of the Related Art

Sequencing Nucleic Acids Using Tagged Monomers

The primary sequences of nucleic acids are crucial for understanding the function and control of genes and for applying many of the basic techniques of molecular biology. The ability to do rapid and reliable DNA sequencing is, therefore, a very important technology. The DNA sequence is an important tool in genomic analysis as well as other applications, such as genetic identification, forensic analysis, genetic counseling, medical diagnostics, etc. With respect to the area of medical diagnostic sequencing, disorders, susceptibilities to disorders, and prognoses of disease conditions, can be correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations and ras proto-oncogene mutations. See, e.g., Gyllensten et al., PCR Methods and Applications, 1: 91–98 (1991); U.S. Pat. No. 5,578,443, issued to Santamaria et al., incorporated herein by reference; and U.S. Pat. No.5,776,677, issued to Tsui et al., incorporated herein by reference.

Various approaches to DNA sequencing exist. The dideoxy chain termination method serves as the basis for all currently available automated DNA sequencing machines. See, e.g., Sanger et al., Proc. Natl. Acad. Sci., 74: 5463–5467 (1977); Church et al., Science, 240: 185–188 (1988); and Hunkapiller et al., Science, 254: 59–67 (1991)). Other methods include the chemical degradation method, see, e.g., Maxam et al., Proc. Natl. Acad. Sci., 74: 560–564 (1977); whole-genome approaches see, e.g., Fleischmann et al., Science, 269,496 (1995); expressed sequence tag sequencing see, e.g., Velculescu et al., Science, 270, (1995); array methods based on sequencing by hybridization, see, e.g., Koster et al., Nature Biotechnology, 14,1123 (1996); and single molecule sequencing (SMS), see, e.g., Jett et al., J. Biomol. Struct. Dyn. 7,301 (1989), Schecker et al., Proc. SPIE-Int. Soc. Opt. Eng. 2386,4 (1995), and Hardin et al. U.S. pat. appln. Ser. No. 09/901,782, filed Jul. 9, 2001, incorporated herein by reference.

Fluorescent dyes can be used in a variety of these DNA sequencing techniques. A fluorophore moiety or dye is a molecule capable of generating a fluorescence signal. A quencher moiety is a molecule capable of absorbing the energy of an excited fluorophore, thereby quenching the fluorescence signal that would otherwise be released from the excited fluorophore. In order for a quencher to quench an excited fluorophore, the quencher moiety must be within a minimum quenching distance of the excited fluorophore moiety at some time prior to the fluorophore releasing the stored fluorescence energy.

Fluorophore-quencher pairs have been incorporated into oligonucleotide probes in order to monitor biological events based on the fluorophore and quencher being separated or brought within a minimum quenching distance of each other. For example, probes have been developed wherein the intensity of the fluorescence increases due to the separation of the fluorophore-quencher pair. Probes have also been developed which lose their fluorescence because the quencher is brought into proximity with the fluorophore.

These fluorophore-quencher pairs have been used to monitor hybridization assays and nucleic acid amplification reactions, especially polymerase chain reactions (PCR), by monitoring either the appearance or disappearance of the fluorescence signal generated by the fluorophore molecule.

The decreased fluorescence of a fluorophore moiety by collision or direct interaction with a quencher is due mainly to a transfer of energy from the fluorophore in the excited state to the quencher. The extent of quenching depends on the concentration of quencher and is described by the Stern-Volmer relationship:

$$F_0/F = 1 + K_{SV}[Q]$$

wherein $F_0$ and $F$ correspond to the fluorescence in the absence and presence of quencher, respectively, and $[Q]$ is the quencher concentration. A plot of $F_0/F$ versus $[Q]$ yields a straight line with a slope corresponding to the Stern-Volmer constant, $K_{SV}$. The foregoing equation takes into account the dynamic and collisional quenching which is the dominant component of the quenching reaction. A linear S-V plot can be obtained when the quenching is completely due to a dynamic (or collisional) process or a static complex formation. A non-linear plot will occur when both static and collisional quenching are occurring simultaneously (see, A. M. Garcia, Methods in Enzymology, 207,501–511 (1992)).

In general, fluorophore moieties preferably have a high quantum yield and a large extinction coefficient so that the dye can be used to detect small quantities of the component being detected. Fluorophore moieties preferably have a large Stokes shift (i.e., the difference between the wavelength at which the dye has maximum absorbance and the wavelength at which the dye has maximum emission) so that the fluorescent emission is readily distinguished from the light source used to excite the dye.

One class of fluorescent dyes which has been developed is the energy transfer fluorescent dyes. For instance, U.S. Pat. Nos. 5,800,996, and 5,863,727, issued to Lee et al., disclose donor and acceptor energy fluorescent dyes and linkers useful for DNA sequencing, incorporated therein by reference. Other fluorophore-quencher pairs are disclosed in PCT Application Serial No. PCT/US99/29584, incorporated herein by reference. In energy transfer fluorescent dyes, the acceptor molecule is a fluorophore which is excited at the wavelength of light corresponding to the fluorescence emission the excited donor molecule. When excited, the donor dye transmits its energy to the acceptor dye.

Therefore, emission from the donor is partially or totally quenched due to partial or total energy transfer from the excited donor to the acceptor dye, resulting in the excitation of the latter for emission at its characteristic wavelength (i. e., a wavelength different from that of the donor dye which may represent a different color if the emissions are in the visible portion of the spectrum). The advantage of this mechanism is twofold; the emission from the acceptor dye is more intense than that from the donor dye alone when the acceptor has a higher fluorescence quantum yield than the donor (see, Li et al., Bioconjugate Chem., 10: 242–245, (1999)) and attachment of acceptor dyes with differing emission spectra allows differentiation among molecules by fluorescence using a single excitation wavelength.

Nucleotide triphosphates having a fluorophore moiety attached to the γ-phosphate are of interest as this modification still allows the modified NTPs to be enzyme substrates. For instance, Felicia et al., describe the synthesis and spectral properties of a "always-on" fluorescent ATP analog, adenosine-5'-triphosphoroyl-(5-sulfonic acid)naphthyl ethylamindate (γ-1,5-EDANS) ATP. Yarbrough et al. 1978, JBC. The analog is a good substrate for *E. coli* RNA polymerase and can be used to initiate the RNA chain. The ATP analog is incorporated into the RNA synthesized and is a good probe for studies of nucleotide-protein interactions, active site mapping and other ATP-utilizing biological systems. See, e.g., Felicia et al., Arch. Biochem Biophys., 246: 564–571 (1986).

In addition, Sato et al., disclose a homogeneous enzyme assay that uses a fluorophore moiety (bimane) attached to the γ-phosphate group of the nucleotide and a quencher moiety attached to the 5-position of uracil. The quencher moiety is in the form of a halogen, bound to the C-5 position of the pyrimidine. The quenching that is effected by this combination is eliminated by cleavage of the phosphate bond by the phosphodiesterase enzyme. The halogen quencher used in the assay is very inefficient producing only about a two fold decrease in fluorescent efficiency.

Template-Mediated Primer Extension Reaction

In a template-mediated primer extension reaction, an oligonucleotide primer having homology to a single-stranded template nucleic acid is caused to anneal to a template nucleic acid, the annealed mixture is then provided with a DNA polymerase in the presence of nucleoside triphosphates under conditions in which the DNA polymerase extends the primer to form a complementary strand to the template nucleic acid. In a Sanger-type DNA sequencing reaction, the primer is extended in the presence of a chain-terminating agent, e.g., a dideoxynucleoside triphosphate, to cause base-specific termination of the primer extension (Sanger). In a polymerase chain reaction, two primers are provided, each having homology to opposite strands of a double-stranded DNA molecule. After the primers are extended, they are separated from their templates, and additional primers caused to anneal to the templates and the extended primers. The additional primers are then extended. The steps of separating, annealing, and extending are repeated in order to geometrically amplify the number of copies of the template nucleic acid (Saiki).

In both DNA sequencing and PCR, it is critically important that the primer extension product accurately replicate the nucleotide sequence of the template nucleic acid. However, under certain conditions, peak "dropout" has been observed wherein certain nucleotides are not represented in the primer extension product. This problem is believed to be caused by pyrophosphorolysis of the primer extension product by a reverse nucleotide addition reaction promoted by the accumulation of pyrophosphates in the reaction mixture. See Mullis; Tabor 1990; Tabor 1996.

Pyrophosphate Effects on Nucleic Acid Synthesis and/or Sequencing

It has been recognized that pyrophosphorolysis, where an oligonucleotide is reduced in length, is detrimental to primer extension reactions. The pyrophosphorolysis is caused by the availability of pyrophosphate. For example, PCR is inhibited by the addition of pyrophosphate even at very low concentrations. According to U.S. Pat. No. 5,498,523, this pyrophosphorolysis can be prevented by providing an agent, for example, a pyrophosphatase, capable of removing pyrophosphate. Addition of pyrophosphatase to a PCR greatly enhances the progress of the reaction and provides superior results compared to the reaction without a pyrophosphatase. See U.S. Pat. No. 4,800,159, incorporated herein by reference.

Similarly, the addition of a pyrophosphatase to a sequencing reaction provides more uniformity in intensities of bands formed in a polyacrylamide gel used to identify products of the sequencing reaction. This uniformity is due to prevention of degradation of specific DNA products by pyrophosphorolysis. See also, Tabor, S. and Richardson, C. C., J. Biol. Chem. 265:8322 (1990) and U.S. Pat. No. 4,962,020, incorporated herein by reference.

Each product or band in a dideoxy sequencing experiment is a polynucleotide complementary to the template and terminated at the 3' end in a base-specific manner with a dideoxynucleotide. The dideoxy stabilizes the product, preventing further polymerization of the polynucleotide. However, in certain regions of the template, the bands, especially after prolonged reaction, will reduce in intensity or completely disappear ("drop-out" bands). In certain sequence contexts, the PPi contained within the enzyme is thought to remain there for an extended period of time. A drop-out may not be readily detected by the operator, leading to errors in the interpretation of the data either by a human or computer-driven analyzer. Since this phenomenon is stimulated by inorganic pyrophosphate, the effect is presumably due to pyrophosphorolysis (reverse polymerization), not 3'-exonucleolytic activity. It is hypothesized that DNA polymerase idling at the end of these terminated products and in the presence of sufficient pyrophosphate will remove the dideoxynucleotide, then extend from the now free 3'-hydroxyl end to another dideoxy termination. In effect, the bands are converted to longer polynucleotides bands. Removal of pyrophosphate as it is generated in the polymerization reaction eliminates this problem.

Sequencing by Direct Detection of Released Tagged Pyrophosphate

Researchers have used a series of enzyme reactions coupled to pyrophosphate generation to measure DNA polymerase activity. In the first (P. Nyren, Anal. Biochem. 167:235 (1987)), Nyren used ATP: sulfate adenylyltransferase to convert pyrophosphate and adenosine 5'-phosphosulfate to ATP and sulfate ion. The ATP was used to make light with luciferase. In the second (J. C. Johnson et al., Anal. Biochem. 26:137 (1968)), the researchers reacted the pyrophosphate with UDP-glucose in the presence of UTP: glucose-1-phosphate uridylyltransferase to produce UTP and glucose-1-phosphate. In two more steps, polymerase activity was measured spectrophotometrically by the conversion of NADP to NADPH. While these articles describe the use of ATP: sulfate adenylyltransferase and UTP: glucose-1-phosphate uridylyltransferase in measuring DNA polymerase activity, they do not describe their use to prevent or inhibit pyrophosphorolysis in nucleic acid synthesis reactions.

DNA sequencing is an essential tool in molecular genetic analysis. The ability to determine DNA nucleotide sequences has become increasingly important as efforts have commenced to determine the sequences of the large genomes of humans and other higher organisms.

The two most commonly used methods for DNA sequencing are the enzymatic chain-termination method of Sanger and the chemical cleavage technique of Maxam and Gilbert.

Both methods rely on gel electrophoresis to resolve, according to their size, DNA fragments produced from a larger DNA segment. Since the electrophoresis step as well as the subsequent detection of the separated DNA fragments are cumbersome procedures, a great effort has been made to automate these steps. However, despite the fact that automated electrophoresis units are commercially available, electrophoresis is not well suited for large-scale genome projects or clinical sequencing where relatively cost-effective units with high throughput are needed. Thus, the need for nonelectrophoretic methods for sequencing is great and several alternative strategies have been described, such as scanning tunnel electron microscopy (Driscoll et al. 1990, Nature, 346,294–296), sequencing by hybridization (Bains et al., 1988, J. Theo. Biol. 135, 308–307) and single molecule detection (Jeff et al., 1989, Biomol. Struct. Dynamics, 7, 301–306), to overcome the disadvantages of electrophoresis.

Techniques enabling the rapid detection of a single DNA base change are also important tools for genetic analysis. In many cases detection of a single base or a few bases would be a great help in genetic analysis since several genetic diseases and certain cancers are related to minor mutations. A mini-sequencing protocol based on a solid phase principle was described (Hultman, et al., 1988, Nucl. Acid. Res., 17, 4937–4946; Syvanen et al., 1990, Genomics, 8, 684–692). The incorporation of a radio labeled nucleotide was measured and used for analysis of the three-allelic polymorphism of the human apolipoprotein E gene. However, radioactive methods are not well suited for routine clinical applications and hence the development of a simple non-radioactive method for rapid DNA sequence analysis has also been of interest.

Methods of sequencing based on the concept of detecting inorganic pyrophosphate (PPi) which is released during a polymerase reaction have been described (WO 93/23564 and WO 89/09283). As each nucleotide is added to a growing nucleic acid strand during a polymerase reaction, a pyrophosphate molecule is released. It has been found that pyrophosphate released under these conditions can be detected enzymically e.g. by the generation of light in the luciferase-luciferin reaction. Such methods enable a base to be identified in a target position and DNA to be sequenced simply and rapidly whilst avoiding the need for electrophoresis and the use of harmful radio labels. See for example U.S. Pat. No. 5,498,523, incorporated herein by reference.

However, the PPi-based sequencing methods mentioned above are not without drawbacks. The template must be washed thoroughly between each nucleotide addition to remove all non-incorporated deoxynucleotides. This makes it difficult to sequence a template which is not bound to a solid support. In addition new enzymes must be added with each addition of deoxynucleotide.

Thus, there is a need for improved methods of sequencing which allow rapid detection, have increase fidelity and provision of sequence information and which are simple and quick to perform, lending themselves readily to automation.

SUMMARY OF THE INVENTION

The present invention overcomes the deficiencies of the prior art and provides a nucleotide polymerization using nucleotides having a molecular and/or atomic tag bonded to or associated with the nucleotide or nucleoside to alter fidelity of nucleotide incorporation. In a preferred embodiment, the tag is bonded to or associated with a portion of the nucleotide that is released after nucleotide incorporation in a growing polymer chain. Preferably, the released portion is the pyrophosphate moiety including the $\beta$ and $\gamma$ phosphate groups.

When a pyrophosphate group having a molecular and/or atomic tag bonded to or associated therewith is released from the nucleoside triphosphate upon incorporation in a growing polymer chain, the tagged pyrophosphate group does not (significantly) stimulate pyrophosphorolysis.

The present invention also provides a method for preventing reverse polymerization or depolymerization of polymer formed using single-molecule sequencing methods as set forth in U.S. Prov. Pat. Appln. Ser. No. 60/216,594, filed Jul. 7, 2000 and U.S. patent application Ser. No. 09/901,782, filed Jul. 9, 2001, incorporated herein by reference.

The present invention farther provides a method for improving incorporation fidelity by adding a modified $PP_i$ to a nucleoside polymerization medium in an amount sufficient to improve incorporation fidelity and/or to inhibit of pyrophosphorolysis of formed products. Preferred modified pyrophosphates include pyrophosphates bearing a group on one or both phosphate moieties that reduce, inhibit or prevent pyrophosphorolysis or pyrophosphates produced from NTPs or dNTPs having a group on the $\beta$ and/or $\gamma$ phosphate moiety.

The present invention provides a heterogeneous assay for detecting base incorporation and pyrophosphate cleavage. The assay utilizes labeled NTPs or dNTPs, a target nucleic acid, a primer nucleic acid and a polymerase. The assay includes the steps of flowing the labeled nucleotide triphosphate (NTP, dNTP, etc.) having a molecular and/or atomic tag bonded to or associated with the $\beta$- and/or $\gamma$-phosphate past an immobilized component selected from the group consisting of the polymerase, the primer and the target nucleic acid. Next, the appropriate labeled NTP or dNTP is incorporated on the primer strand hybridized to the target nucleic acid using the polymerase and results in the release of a tagged pyrophosphate from the dNTP. The incorporation event or the release event can be detected either by measuring a detectable property of the NTP or dNTP upon binding and/or during incorporation or by measuring a detectable property of the released pyrophosphate. The detectable property can be a property inherent in the molecular or atomic tags or produced as a result of the interaction between the molecular or atomic tag on the phosphates of the label NTP or released pyrophosphate and other tags bonded to or associated with the polymerase, the matrix or mobile or immobile components in the media.

The present invention also provides a polymerase immobilized on a solid support and a labeled nucleotide triphosphate selected from the group consisting of dTP, dCTP, dGTP, dTTP, dUTP, ATP, CTP, GTP, UTP and mixtures thereof, where the tags are molecular and the molecules are fluorophores and the detectable property is fluorescent light emission or quenching. The detection of the fluorescent light is preferably accomplished using single molecule detection such as a charge couple device (CCD) camera or intensified CCD camera systems or the like.

The present invention provides kits and integrated systems for practicing the assays described herein. In certain aspects, the present invention provides a kit for assaying pyrophosphate cleavage, comprising: (a) a plurality of nucleotides triphosphates each having a γ-phosphate with a distinguishing fluorophore moiety attached thereto and each having a quencher moiety sufficiently proximal to the distinguishing fluorophore moiety to prevent fluorescence of the distinguishing fluorophore moiety; wherein the distinguishing fluorophore moiety exists quenched with at least about a 5 fold quenching efficiency when the γ-phosphate is attached to each of the plurality of dNTP moieties and each is unquenched when the γ-phosphate is detached from each of the plurality of dNTP moieties; and (b) a polymerase. Preferably, the polymerase is immobilized on a solid support.

The present invention provides a primer extension method in which the extent of pyrophosphorolysis of a primer extension product is reduced, and solutions and kits useful for practicing the method.

The present invention provides a primer extension method wherein "peak drop-out" is reduced and the fidelity of template-sequence reproduction is maximized.

The present invention provides an improved method for performing a primer extension reaction including the steps of annealing an oligonucleotide primer to a portion of a template nucleic acid thereby forming a primer template hybrid; adding primer-extension reagents including a NTP or dNTP having a β- and/or γ-phosphate moiety having a molecular and/or atomic tag bonded to or associated with the β- and/or γ-phosphate moiety to the primer-template hybrid for extending the primer; and optionally adding a co-substrate-enzyme pair to the primer-template hybrid for conducting a pyrophosphate-utilizing reaction, where the tagged, released pyrophosphate reduces the amount of pyrophosphorolysis in the reaction. One should recognize that the release $PP_i$ is a modified $PP_i$ and acts to inhibit deleterious interference untagged $PP_i$ has on nucleotide polymerization.

The present invention provides a method of inhibiting or preventing pyrophosphorolysis during synthesis of a nucleic acid molecule, said method comprising: (a) combining one or more nucleotides having a molecular and/or atomic tag bonded to or associated with β- and/or γ-phosphate moiety of the nucleoside and a nucleic acid template; (b) incubating the one or more nucleotides and nucleic acid template, under conditions sufficient to form a second nucleic acid molecule complementary to all or a portion of the nucleic acid template.

The method of the invention more specifically relates to a method of inhibiting or preventing pyrophosphorolysis, said method comprising: (a) combining a primer with a nucleic acid template under conditions sufficient to form a hybridized product; and (b) incubating said hybridized product in the presence of (i) one or more nucleotides having a molecular and/or atomic tag bonded to or associated with a β- and/or γ-phosphate moiety of the nucleoside, and (ii) a polymerase, and (iii) optionally an enzyme selected from the group consisting of a pentosyltransferase, a phosphotransferase with alcohol group as acceptor, a nucleotidyltransferase, and a carboxy-lyase under conditions sufficient to synthesize a second nucleic acid molecule complementary to all or a portion of said nucleic acid template.

Specifically, the method of the present invention relates to inhibition of pyrophosphorolysis in the synthesis of DNA and RNA molecules using the appropriate nucleotides having a molecular and/or atomic tag bonded to or associated with a β- and/or γ-phosphate moiety of the nucleoside and polymerases (dNTPs/rNTPs and DNA polymerase/RNA polymerase).

The present invention provides a primer extension reaction to prevent the inhibition of nucleic acid synthesis during amplification and to prevent band drop out in sequencing reactions. Thus, the method to prevent inhibition of nucleic acid synthesis during amplification of a double stranded nucleic acid molecule comprises: (a) providing a first and second primer, wherein said first primer is complementary to a sequence at or near the 3' termini of the first strand of said nucleic acid molecule and said second primer is complementary to a sequence at or near the 3' termini of the second strand of said nucleic acid molecule; (b) hybridizing said first primer to said first strand and said second primer to said second strand in the presence of (i) a polymerase, and (ii) optionally an enzyme selected from the group consisting of a pentosyltransferase, a phosphotransferase with an alcohol group as an acceptor, a nucleotidyltransferase and a carboxy-lyase under conditions such that a third nucleic acid molecule complementary to said first strand and a fourth nucleic acid molecule complementary to said second strand are synthesized from nucleosides having a molecular and/or atomic tag bonded to or associated with a β- and/or γ-phosphate moiety of the nucleoside; (c) denaturing said first and third strand and said second and fourth strand; and (d) repeating steps (a) to (c) one or more times. Again, the $PP_i$ released in the nucleotide polymerization of this invention do not cause the deleterious effects that nascent $PP_i$ can cause, therefore, the need to enzymatically degrade $PP_i$ is only for optional protection.

The present invention also provides a method of sequencing a DNA molecule comprising: (a) combining a primer with a first DNA molecule under conditions sufficient to form a hybridized product; (b) contacting said hybridized product with nucleotides having a molecular and/or atomic tag bonded to or associated with a β- and/or γ-phosphate moiety of the nucleoside, a DNA polymerase, optionally an enzyme selected from the group consisting of a pentosyltransferase, a phosphotransferase with an alcohol group as acceptor, a nucleotidyltransferase and a carboxy-lyase; and a terminator nucleotide to give a reaction mixture; (c) incubating the reaction mixture under conditions sufficient to synthesize a population of DNA molecules complementary to said first DNA molecule, wherein said synthesized DNA molecules are shorter in length than said first DNA molecule and wherein said synthesized DNA molecules comprise a terminator nucleotide at their 3' termini; and (d)

separating said synthesized DNA molecules by size so that at least a part of the nucleotide sequence of said first DNA molecule can be determined.

In addition to reducing band drop out, which is believed to result from a ddNTP being added and then being release due to reattaching release pyrophosphate followed by standard extension, thereby, producing under representation of that position in the DNA sequence data, the use of β- and/or γ-phosphate modified nucleotides will result in improved sequencing using traditional fluorescent sequencing reaction due to a decrease in background and/or reduction in band spreading. The first improvement would result from using β- and/or γ-phosphate modified dideoxynucleotidesm which are incorporated at improved accuracy (less incorporation of incorrect ddNTP, reducing background signal). While the second improvement would result from using β- and/or γ-phosphate modified nucleotides to produce identical (or substantially identical) DNA polymers instead of the population of molecules that result from inaccurate incorporation of dNTPs. Thus, the traditional fluorescent sequencing reaction can undergo a two stage improvement by using β- and/or γ-phosphate modified nucleotides and β- and/or γ-phosphate modified dideoxy nucleotides.

The present invention provides a novel modified $PP_i$-based sequencing method for sequencing reactions, where the method can be performed without intermediate washing steps, enabling the procedure to be carried out simply and rapidly, for example in a single micro titre plate. Moreover, the method can be performed with immobilized DNA in solution or on a support or with mobile DNA and immobilized polymerase in solution or on a support. Furthermore, the method can be readily adapted to permit the sequencing reactions to be continuously monitored in real-time, with a signal being generated and detected, as each nucleotide is incorporated.

The present invention provides a method of identifying a base at a target position in a sample DNA sequence wherein an extension primer, which hybridizes to the sample DNA immediately adjacent to the target position is provided and the sample DNA and extension primer are subjected to a polymerase reaction in the presence of a deoxynucleotide having a molecular and/or atomic tag bonded to or associated with a β- and/or γ-phosphate moiety of the nucleoside or dideoxynucleotide having a molecular and/or atomic tag bonded to or associated with a β- and/or γ-phosphate moiety of the nucleoside whereby the tagged deoxynucleotide or tagged dideoxynucleotide will only become incorporated and release tagged pyrophosphate (tPPi) if it is complementary to the base in the target position, any incorporation and/or release of tPPi may be detected via any detection method capable of identifying a detectable property of the tagged deoxynucleotide, tagged dideoxynucleotide or tagged pyrophosphate, different tagged deoxynucleotides or tagged dideoxynucleotides being added either to separate aliquots of sample-primer mixture or successively to the same sample-primer mixture and subjected to the polymerase reaction to indicate which tagged deoxynucleotide or tagged dideoxynucleotide is incorporated, optionally characterised in that, a nucleotide-degrading enzyme is included during the polymerase reaction step, such that unincorporated nucleotides are eliminated.

The present invention is also ideally suited for single nucleotide extensions reactions because the tagged $PP_i$ released during incorporation does not cause the deleterious effects associated with the release of nascent $PP_i$, and where the fidelity of the tagged nucleotide incorporation in improved.

The invention also provides a kit for carrying out nucleic acid syntheses with improved fidelity comprising a container including a polymerizing compartment comprising a nucleic acid polymerizing agent, a monomer compartment comprising nucleotide monomers for the polymerizing agent and a fidelity enhancing agent compartment comprising a fidelity enhancing agent, where the fidelity enhancing agent comprises a tagged-phosphate, tagged-pyrophosphate or tagged-polyphosphate or derivatives thereof.

The invention also provides a kit for carrying out nucleic acid syntheses with improved fidelity comprising a container including a polymerizing compartment comprising a nucleic acid polymerizing agent and a monomer compartment comprising nucleotide monomers for the polymerizing agent, where the monomers comprise dNTPs, ddNTPs, β- and/or γ-phosphate modified nucleotides, β- and/or γ-phosphate modified dideoxy nucleotides or mixtures or combinations thereof.

The invention also provides a kit for carrying out nucleic acid syntheses with improved fidelity comprising a container including a polymerizing compartment comprising a nucleic acid polymerizing agent and monomer compartments, each compartment comprising a nucleotide monomer for the polymerizing agent, where the monomers comprise dNTPs, ddNTPs, β- and/or γ-phosphate tagged dNTPs, β- and/or γ-phosphate tagged ddNTPs or mixtures or combinations thereof.

DESCRIPTION OF THE DRAWINGS

The invention can be better understood with reference to the following detailed description together with the appended illustrative drawings in which like elements are numbered the same:

FIG. 5 depicts the use of γ-modified nucleotides with the Pfu DNA polymerase that shows this polymerase does not efficiently use γ-modified nucleotides;

FIG. 12 depicts a summary of extension results for various polymerase incorporating ANS-tagged dNTPs;

FIG. 14 TOP: Representative gels demonstrating the results obtained in single nucleotide extension assays using the Bot-C template. Incorporation of matched (dGTP & ANS-dGTP, above) and mismatched (dTTP & ANS-dTTP, below) nucleotides are shown. BOTTOM: Graphic presentation of the fidelity improvements afforded by ANS addition to the γ-phosphate of each dNTP. The increase in percent extension of the natural nucleotide relative to the ANS-tagged nucleotide is indicated above the natural nucleotide.

DEFINITIONS

Figure 1:
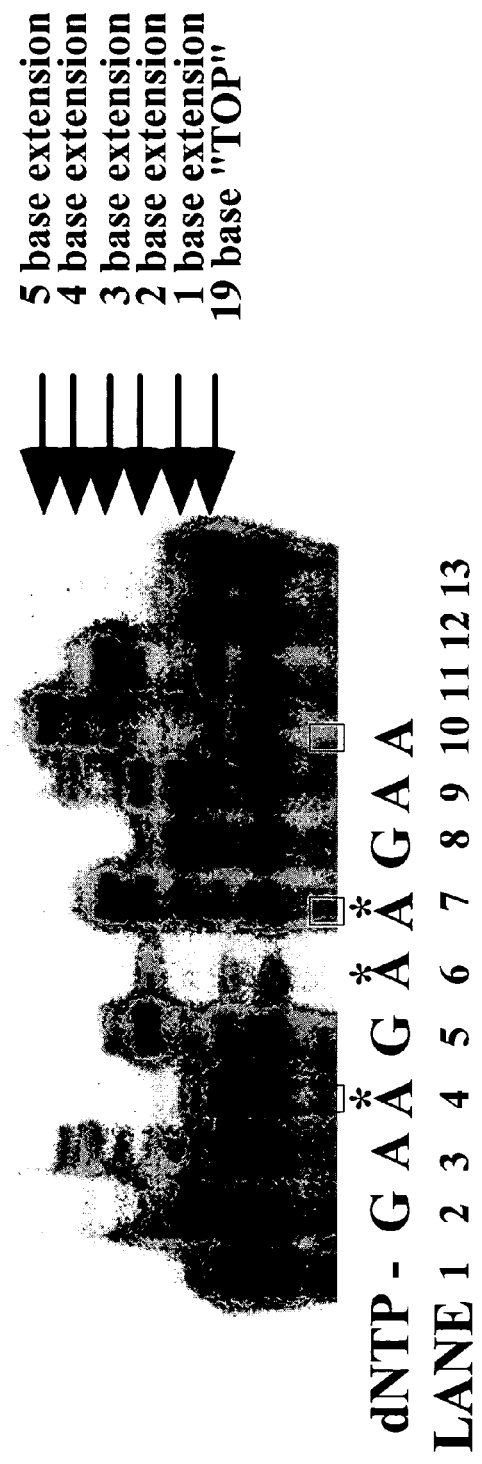
FIG. 1 depicts the incorporation of ANS-γ-phosphate dATP using Taq polymerase and a primer.

Unless stated otherwise, the following terms and phrases as used herein are intended to have the following meanings:

The term "heterogeneous" assay as used herein refers to an assay method wherein at least one of the reactants in the assay mixture is attached to a solid phase, such as a solid support.

The term "oligonucleotide" as used herein includes linear oligomers of nucleotides or analogs thereof, including deoxyribonucleosides, ribonucleosides, and the like. Usually, oligonucleotides range in size from a few monomeric units, e. g. 3–4, to several hundreds of monomeric units. Whenever an oligonucleotide is represented by a sequence of letters, such as "ATGCCTG", it will be understood that the nucleotides are in 5'-3' order from left to right and that "A" denotes deoxyadenosine, "C" denotes deoxycytidine, "G" denotes deoxyguanosine, and "T" denotes thymine, unless otherwise noted.

The term "nucleoside" as used herein refers to a compound consisting of a purine, deazapurine, or pyrimidine nucleoside base, e. g., adenine, guanine, cytosine, uracil, thymine, deazaadenine, deazaguanosine, and the like, linked to a pentose at the 1' position, including 2'-deoxy and 2'-hydroxyl forms, e. g., as described in Kornberg and Baker, DNA Replication, 2nd Ed. (Freeman, San Francisco, 1992) and further include, but are not limited to, synthetic nucleosides having modified base moieties and/or modified sugar moieties, e. g. described generally by Scheit, Nucleotide Analogs (John Wiley, N. Y., 1980). Suitable NTPs include both naturally occurring and synthetic nucleotide triphosphates, and are not limited to, ATP, dATP, CTP, dCTP, GTP, dGTP, TTP, dTTP, ITP, dITP, UTP and dUTP. Preferably, the nucleotide triphosphates used in the methods of the present invention are selected from the group of dATP, dCTP, dGTP, dTTP, dUTP and mixtures thereof.

The term "nucleotide" as used herein refers to a phosphate ester of a nucleoside, e.g., mono, di and triphosphate esters, wherein the most common site of esterification is the hydroxyl group attached to the C-5 position of the pentose and includes deoxyribonucleoside triphosphates such as dATP, dCTP, dITP, dUTP, dGTP, dTTP, or derivatives thereof such as their dideoxy derivatives: ddATP, ddCTP, ddITP, ddUTP, ddGTP, ddTTP. Such derivatives include, for example [aS]dATP, 7-deaza-dGTP and 7-deaza-dATP. The term "nucleotide" as used herein also refers to ribonucleoside triphosphates (NTPs) and their derivatives. Illustrated examples of ribonucleoside triphosphates include, but are not limited to, ATP, CTP, GTP, ITP and UTP.

The term "primer" refers to a linear oligonucleotide which specifically anneals to a unique polynucleotide sequence and allows for amplification of that unique polynucleotide sequence or to a nucleic acid, e.g., synthetic oligonucleotide, which is capable of annealing to a complementary template nucleic acid and serving as a point of initiation for template-directed nucleic acid synthesis. Typically, a primer will include a free hydroxyl group at the 3'-end.

The phrase "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, or oligonucleotide, as well as the express identification and ordering of nucleotides, usually each nucleotide, in a target polynucleotide. The term also includes the determination of the identification, ordering, and locations of one, two, or three of the four types of nucleotides within a target polynucleotide.

The term "solid-support" refers to a material in the solid-phase that interacts with reagents in the liquid phase by heterogeneous reactions. Solid-supports can be derivatized with proteins such as enzymes, peptides, oligonucleotides and polynucleotides by covalent or non-covalent bonding through one or more attachment sites, thereby "immobilizing" the protein or nucleic acid to the solid-support.

The phrase "target nucleic acid" or "target polynucleotide" refers to a nucleic acid or polynucleotide whose sequence identity or ordering or location of nucleosides is to be determined using methods described herein.

The term "primer-extension reagent" means a reagent including components necessary to effect the enzymatic template-mediated extension of a primer. Primer extension reagents include: (i) a polymerase enzyme, e.g., a thermostable polymerase enzyme such as Taq DNA polymerase, and the like; (ii) a buffer to stabilize pH; (iii) deoxynucleotide triphosphates, e.g., deoxyguanosine 5'-triphosphate, 7-deazadeoxyguanosine 5'-triphosphate, deoxyadenosine 5'-triphosphate, deoxythymidine 5'-triphosphate, deoxycytidine 5'-triphosphate; and, optionally in the case of a Sanger-type DNA sequencing reaction, (iv) dideoxynucleotide triphosphates, e.g., dideoxyguanosine 5'triphosphate, 7-deazadideoxyguanosine 5'-triphosphate, dideoxyadenosine 5'-triphosphate, dideoxythymidine 5'-triphosphate, dideoxycytidine 5'-triphosphate, and the like.

As used herein, the term "pyrophosphate" refers to two phosphate molecules bound together by an ester linkage, e.g., the structure $^{-2}O_3P-O-PO_3^{-2}$.

The term "nucleotide-degrading enzyme" as used herein includes all enzymes capable of non-specifically degrading nucleotides, including at least nucleoside triphosphates (NTPs), but optionally also di- and monophosphates, and any mixture or combination of such enzymes, provided that a nucleoside triphosphatase or other NTP degrading activity is present. Although nucleotide-degrading enzymes having a phosphatase activity may conveniently be used according to the invention, any enzyme having any nucleotide or nucleoside degrading activity may be used, e.g., enzymes which cleave nucleotides at positions other than at the phosphate group, for example at the base or sugar residues. Thus, a nucleoside triphosphate degrading enzyme is essential for the invention.

The term "atomic tag" means an atom or ion of an atom that when attached to a nucleotide increase the fidelity of a nucleotide polymerizing agent such as a polymerase at the atom tagged nucleotide is incorporated into a nucleotide sequence.

The term "molecular tag" means an atom or ion of an atom that when attached to a nucleotide increase the fidelity of a nucleotide polymerizing agent such as a polymerase at the atom tagged nucleotide is incorporated into a nucleotide sequence.

The term "polymerizing agent" means any naturally occurring or synthetic agent capable of polymerizing nucleotides to produce polynucleotide, including polymerases, reverse transcriptases, or the related naturally occurring nucleotide polymerizing systems. The term polymerizing agent also includes variants of naturally occurring polymerases or reverse transcriptases where one or more amino acids have been added to, removed from or replaced in the nature amino acid sequence. Thus, the term covers all known and to be constructed systems capable of forming oligomers or polymers of nucleotides.

DETAILED DESCRIPTION OF THE INVENTION

The inventors have found that nucleotide monomers or analogs thereof bearing an atomic and/or molecular tag on a site of the molecule can increase the fidelity of nucleotide polymerization for nucleotide polymerization agents that can incorporated the modified monomers. This increase in fidelity is useful for improving nucleic acid sequencing determinations using any of the standard sequencing reactions such as PCR, rolling circle or the like. Additionally, these modified monomers may allows the construction of drugs for animal or human use that would increase the fidelity of viral disease replication in vivo decreasing mutagensis allowing the immune system to recognize the virus. Such a medication may be of particular benefit for virus such as the HIV virus that causes AIDS.

Mutation of amino acids within the polymerase is the classic approach to understand enzyme action and/or modulate enzyme fidelity (Yang S and Chatterjee D K. (1999) PCT WO9910366; Wainberg M A, Drosopoulos W C, Salomon H, Hsu M, Borkow G, Parniak M, Gu Z, Song Q, Manne J, Islam S, Castriota G, Prasad V R. (1996) *Science* 271:1282–5; Drosopoulos W C, Rezende L F, Wainberg M A, Prasad V R. (1998) *J Mol Med* 76:604–12; Lewis D A, Bebenek K, Beard W A, Wilson S H, Kunkel T A. (1999) *J Biol Chem* 274:32924–30; Kim B, Ayran J C, Sagar S G, Adman E T, Fuller S M, Tran N H, Horrigan J. (1999) *J Biol Chem* 274:27666–73. In stark distinction to this classical approach, the inventors have found a novel approach in that fidelity is improved by manipulating the substrate.

Invention Scope

The present invention relates to a composition comprising a nucleotides including deoxyribonucleotide, dideoxynucleotide, or ribonucleotide including a molecular and/or atomic tag on β and/or γ phosphate group and/or a base moiety, where the tag alters fidelity of base incorporation.

The present invention relates to a method comprising the step of adding a composition comprising a nucleotides including deoxyribonucleotide, dideoxynucleotide, or ribonucleotide including a molecular and/or atomic tag on a β and/or γ phosphate group and/or a base moiety, where the tag alters fidelity of base incorporation to a nucleotide polymerization medium comprising a nucleotide polymerase.

The present invention relates to a composition comprising a nucleotides including deoxyribonucleotide, dideoxynucleotide, or ribonucleotide including a molecular and/or atomic tag on a β phosphate group and/or a base moiety, where the tag alters fidelity of base incorporation.

The present invention relates to a method comprising the step of adding a composition comprising a nucleotides including deoxyribonucleotide, dideoxynucleotide, or ribonucleotide including a molecular and/or atomic tag on a β phosphate group and/or a base moiety, where the tag alters fidelity of base incorporation to a nucleotide polymerization medium comprising a nucleotide polymerase.

The present invention relates to a composition comprising a nucleotides including deoxyribonucleotide, dideoxynucleotide, or ribonucleotide including a molecular and/or atomic tag on a γ phosphate group and/or a base moiety, where the tag alters fidelity of base incorporation.

The present invention relates to a method comprising the step of adding a composition comprising a nucleotides including deoxyribonucleotide, dideoxynucleotide, or ribonucleotide including a molecular and/or atomic tag on a γ phosphate group and/or a base moiety, where the tag alters fidelity of base incorporation to a nucleotide polymerization medium comprising a nucleotide polymerase.

The present invention relates to a method comprising the step of adding a nucleotides including deoxyribonucleotide, dideoxynucleotide, or ribonucleotide including a molecular and/or atomic tag on a β and/or γ phosphate group to an assay involving a polymerase and/or a base moiety, where the tag alters fidelity of base incorporation and the assay is selected from the group consisting of genotyping for in vitro reproductive methods (human and other organisms); single nucleotide polymorphism (SNP) detection; DNA sequencing; RNA sequencing; single nucleotide extension assays; amplified DNA product assays; rolling circle product assays; PCR product assays; allele-specific primer extension assays; single-molecule arrays (DNA, RNA, protein) assays; drug toxicity evaluation assays; or the like. The method can be used to extend a nucleic acid molecule by any number of bases depending on the polymerizing reaction selected. Thus, the molecule can be extended by a single nucleotide up to many thousands of nucleotide to or hundred of thousands of bases.

The present invention relates to a method for making blunt-ended fragments comprising the steps of amplifying a DNA fragment in the presence of a nucleotides including deoxyribonucleotide, dideoxynucleotide, or ribonucleotide including a molecular and/or atomic tag on a γ phosphate group and/or a base moiety, where the tag alters fidelity of base incorporation and decreases or eliminates non-templated addition of a base to the 3' end of the DNA fragment being amplified. Preferably, the amplifying step is a PCR amplification step.

The present invention relates to a composition comprising a pyrophosphorolysis inhibitors selected from the group consisting of compounds of the following general formulas or mixtures or combinations thereof:

| | |
|---|---|
| Z-OPO$_2$O-Z' | (a) |
| Z-PO$_2$O-Z' | (b) |
| Z-OPO$_2$-Z' | (c) |
| Z-PO$_2$-Z' | (d) |
| Z-OPO$_2$—(OP(EE')O)$_n$—PO$_2$O-Z' | (e) |
| Z-OPO$_2$—(OP(EE')O)$_n$PO$_2$-Z' | (f) |
| Z-PO$_2$—(OP(EE')O)$_n$PO$_2$O-Z' | (g) |
| Z-PO$_2$—(OP(EE')O)$_n$PO$_2$-Z' | (h) | where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5.

The present invention relates to a method comprising the step of polymerizing a nucleic acid sequence in the presence of a composition comprising a pyrophosphorolysis inhibitors selected from the group consisting of compounds of the following general formulas or mixtures or combinations thereof:

Z-OPO$_2$O-Z' (a)

Z-PO$_2$O-Z' (b)

Z-OPO$_2$-Z' (c)

Z-PO$_2$-Z' (d)

Z-OPO$_2$—(OP(EE')O)$_n$—PO$_2$O-Z' (e)

Z-OPO$_2$—(OP(EE')O)$_n$PO$_2$-Z' (f)

Z-PO$_2$—(OP(EE')O)$_n$PO$_2$O-Z' (g)

Z-PO$_2$—(OP(EE')O)$_n$PO$_2$-Z' (h)

where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5.

The present invention relates to a heterogeneous assay method for detecting pyrophosphate cleavage, the components of the assay comprising a labeled NTP, a target nucleic acid, a primer nucleic acid and a polymerase, said method comprising: (a) flowing said tagged nucleotide triphosphate (NTP), where β, and/or γ phosphate group and/or a base moiety of the NTP includes an atomic and/or molecular tag having a detectable property attached thereto or associated therewith; (b) incorporating said NTP on a primer strand hybridized to said target nucleic acid using said polymerase and releasing said γ-phosphate with said fluorophore moiety attached thereto; and (c) detecting said fluorescent moiety thereby detecting pyrophosphate cleavage. In one preferred assay, the nucleotide triphosphate (NTP) is a member selected from the group consisting of deoxyadenosine triphosphate, deoxycytosine triphosphate, deoxyguanosine triphosphate and deoxythymidine triphosphate. In another preferred assay, the nucleotide triphosphate (NTP) is a member selected from the group consisting of adenosine triphosphate, cytosine triphosphate, guanosine triphosphate and uridine triphosphate. In another preferred assay, the tags are a fluorescent species which is detected based upon a change in either intensity measurement or fluorescent lifetime measurement. In another preferred assay, the nucleotide triphosphate (NTP) is a plurality of nucleotide triphosphates (NTPs). In another preferred assay, each of said plurality of nucleotide triphosphates (NTPs) has an indicator of identity associated with the tag. In another preferred assay, the polymerase is a member selected from the group consisting of a DNA polymerase, a DNA dependent RNA polymerase and a reverse transcriptase, particularly, where the polymerase is a DNA polymerase, especially, where the polymerase is immobilized on a solid support. In another preferred assay, the polymerase is supported on a solid support that is a member selected from the group consisting of controlled pore glass, a glass plate, polystyrene, an avidin coated polystyrene bead, cellulose, nylon, acrylamide gel and activated dextran.

The present invention relates to a nucleotide triphosphate (NTP) probe comprising a NTP including an atomic and/or molecular tag having a detectable property attached thereto or associated therewith a β and/or γ phosphate group and/or a base moiety of the NTP. In another preferred probe, the NTP is a member selected from the group consisting of a deoxynucleotide triphosphate (dNTP), a nucleotide triphosphate (NTP) and analogs thereof, particularly, where ther NTP is a deoxynucleotide triphosphate (dNTP), especially, where the deoxynucleotide triphosphate (dNTP) is a member selected from the group consisting of deoxyadenosine triphosphate, deoxycytosine triphosphate, deoxyguanosine triphosphate and deoxythymidine triphosphate. In another preferred probe, the nucleotide triphosphate (NTP) is a member selected from the group consisting of adenosine triphosphate, cytosine triphosphate, guanosine triphosphate and uridine triphosphate. In another preferred probe, the tag is fluorophore, particularly, the fluorophore is a member selected from the group consisting of fluorescein, 5carboxyfluorescein (FAM), rhodamine, 5-(2'-aminoethyl) aminonapthalene-1-sulfonic acid (EDANS), anthranilamide, coumarin, terbium chelate derivatives, Reactive Red 4, BODIPY dyes and cyanine dyes. In another preferred probe, the tag is attached to said β and/or γ-phosphate via a linker. In another preferred probe, the fluorophore linker is an alkylene group having between about 5 to about 12 carbons, particularly, where the fluorophore moiety is a fluorescein or rhodamine dye.

The present invention relates to a kit for assaying pyrophosphate cleavage, said kit comprising: (a) a plurality of NTPs at least one NTP including an atomic and/or molecular tag or moiety having distinguishable/detectable property attached to and/or associated with a β and/or γ-phosphate and/or a base moiety of the NTP and (b) a polymerase. In another preferred kit, the tag is a fluorophore and the property is fluorescence. In another preferred kit, the NTP further includes a quencher attached to and/or associated with a β and/or γ-phosphate and/or a base moiety of the NTP, where each fluorophore interacts with said quencher moiety via a mechanism which is a member selected from the group consisting of fluorescence resonance energy transfer (FRET), electron transfer and ground-state complex mechanism.

The present invention relates to a method for performing a primer extension reaction comprising the steps of (a) annealing an oligonucleotide primer to a portion of a template nucleic acid thereby forming a primer-template hybrid; (b) adding primer-extension reagents including a tagged dNTP to afford increased or altered fidelity during incorporation to the primer-template hybrid for extending the primer, where the tagged dNTP includes an atomic and/or molecular tag or moiety having distinguishable/detectable property attached to and/or associated with a β and/or γ-phosphate and/or a base moiety of the dNTP. The method can also include the step of adding cosubstrate-enzyme pair to the primer-template hybrid for conducting a pyrophosphate-utilizing reaction in an amount sufficient to reduce peak dropout. In another preferred method, the cosubstrate-enzyme pair comprises pyrophosphate dependent phosphofructose kinase and fructose-6-phosphate. In another preferred method, the cosubstrate-enzyme pair comprises UDP Glucose Pyrophosphorylase and UDP Glucose.

The present invention relates to a kit for performing a primer extension reaction comprising: primer extension reagents and at least one dNTP including an atomic and/or molecular tag or moiety attached to and/or associated with a β and/or γ-phosphate and/or a base moiety of the dNTP to increase or alter extension fidelity. The kit can further comprise a compound present in an amount sufficient to reduce peak dropout.

The present invention relates to a primer extension solution for the extension of a primer member of a primer template hybrid comprising: primer extension reagents at least one dNTP including an atomic and/or molecular tag or moiety attached to and/or associated with a β and/or γ-phosphate and/or a base moiety of the dNTP to increase or alter extension fidelity. The solution can further comprise a compound present in an amount sufficient to reduce peak dropout. In another preferred solution, the cosubstrate-enzyme pair comprises pyrophosphate dependent phosphofructose kinase and fructose-6-phosphate. In another preferred solution, the cosubstrate-enzyme pair comprises UDP Glucose Pyrophosphorylase and UDP Glucose.

The present invention relates to a method of inhibiting or preventing pyrophosphorolysis during synthesis of a nucleic acid molecule, said method comprising (a) combining one or more tagged nucleotides and a nucleic acid template, where the tagged nucleotide comprises an atomic and/or molecular tag or moiety attached to and/or associated with a β and/or γ-phosphate and/or a base moiety of the nucleotide; and (b) incubating the one or more nucleotides and nucleic acid template together with a polymerase and an enzyme selected from the group consisting of a pentosyltransferase, a phosphotransferase with alcohol group as acceptor, a nucleotidyltransferase, and a carboxy-lyase, under conditions sufficient to form a second nucleic acid molecule complementary to all or a portion of the nucleic acid template.

The present invention relates to a method of inhibiting or preventing pyrophosphorolysis during synthesis of a nucleic acid molecule, said method comprising (a) combining a primer with a nucleic acid template under conditions sufficient to form a hybridized product; and (b) incubating said hybridized product in the presence of (i) one or more tagged nucleotides comprises an atomic and/or molecular tag or moiety attached to and/or associated with a β and/or γ-phosphate and/or a base moiety of the nucleotide (ii) a polymerase, and (iii) an enzyme selected from the group consisting of a pentosyltransferase, a phosphotransferase with an alcohol group as acceptor, a nucleotidyltransferase, and a carboxy-lyase under conditions sufficient to synthesize a second nucleic acid molecule complementary to all or a portion of said nucleic acid template.

The present invention relates to a method to prevent inhibition of nucleic acid synthesis during amplification of a double stranded nucleic acid molecule, comprising (a) providing a first and second primer, wherein said first primer is complementary to a sequence at or near the 3' termini of the first strand of said nucleic acid molecule and said second primer is complementary to a sequence at or near the 3' termini of the second strand of said nucleic acid molecule; (b) hybridizing said first primer to said first strand and said second primer to said second strand in the presence of (i) a polymerase, and (ii) one or more tagged nucleotides comprises an atomic and/or molecular tag or moiety attached to and/or associated with a β and/or γ-phosphate and/or a base moiety of the nucleotide under conditions such that a third nucleic acid molecule complementary to said first strand and a fourth nucleic acid molecule complementary to said second strand are synthesized; (c) denaturing said first and third strand and said second and fourth strand; and (d) repeating steps (a) to (c) one or more times.

The method of claim 47, wherein the hybridizing is in the presence of an enzyme selected from the group consisting of a pentosyltransferase, a phosphotransferase with an alcohol group as an acceptor, a nucleotidyltransferase and a carboxy-lyase.

The present invention relates to a method of identifying a base at a target position in a sample DNA sequence wherein an extension primer, which hybridises to the sample DNA either immediately adjacent to or very near (within about 10 bases) to the target position is provided and the sample DNA and extension primer are subjected to a polymerase reaction in the presence of a tagged deoxynucleotide or dideoxynucleotide, where the tagged deoxynucleotide or dideoxynucleotide an atomic and/or molecular tag or moiety having a detectable property attached to and/or associated with a β and/or γ-phosphate and/or a base moiety of the deoxynucleotide or dideoxynucleotide, whereby the tagged deoxynucleotide or dideoxynucleotide will only become incorporated and release pyrophosphate (PPi) if it is complementary to the base in the target position, any release of PPi being detected, different deoxynucleotides or dideoxynucleotides being added either to separate aliquots of sample-primer mixture or successively to the same sample-primer mixture and subjected to the polymerase reaction to indicate which deoxynucleotide or dideoxynucleotide is incorporated, characterised in that, a nucleotide-degrading enzyme is included during the polymerase reaction step, such that unincorporated nucleotides are degraded.

In another preferred method, the nucleotide-degrading enzyme is apyrase. In another preferred method, the mixture of nucleotide-degrading enzymes is used having nucleoside triphosphatase, nucleoside diphosphatase and nucleoside monophosphatase activity. In another preferred method, the nucleotide-degrading enzyme is immobilised on a solid support. In another preferred method, the immobilised nucleotide-degrading enzyme is added after nucleotide incorporation by the polymerase has taken place, and then removed prior to a subsequent nucleotide incorporation reaction step. In another preferred method, the PPi release is directly detected via the detectable property of the tag. In another preferred method, the polymerase reaction and PPi release detection steps are performed substantially simultaneously. In another preferred method, the sample DNA is immobilised or provided with means for attachment to a solid support. In another preferred method, the sample DNA is first amplified. In another preferred method, the extension primer contains a loop and anneals back on itself and the 3' end of the sample DNA. In another preferred method, a native polymerase, an exonuclease deficient (exo-) high fidelity polymerase or a genetically modified polymerase is used.

In another preferred method, the method can be used for identification of a base in a single target position in a DNA sequence wherein the sample DNA is subjected to amplification; the amplified DNA is immobilized and then subjected to strand separation, the non-immobilized strand being removed and an extension primer, which hybridizes to the immobilized DNA immediately adjacent to the target position, is provided; each of four aliquots of the immobilized single stranded DNA is then subjected to a polymerase reaction in the presence of a tagged deoxynucleotide, each aliquot using a different deoxynucleotide whereby only the tagged deoxynucleotide complementary to the base in the target position becomes incorporated.

The method can further comprising adding the identified dNTP to the three non-extended chambers and repeating the cyclic identification process.

The present invention relates to a kit for use in a method as defined in any one of claims 49 to 6.10, comprising: (a) a test specific primer which hybridizes to sample DNA so that the target position is directly adjacent to the 3' end of the primer; (b) a polymerase; and (c) at least one tagged dNTP an atomic and/or molecular tag or moiety having a detectable property attached to and/or associated with a β and/or γ-phosphate and/or a base moiety of the dNTP. The kit can be used for use with initial PCR amplification, further comprising: (i) a pair of primers for PCR, at least one primer having means permitting immobilization of said primer; (ii) a polymerase for PCR; (iii) a mixture of dNTPs including at least one tagged dNTP. The methods or kits can also be used with a multiplicity of sample DNA sequences, wherein said DNA sequences are arranged in array format on a solid surface.

The present invention relates to a composition comprising a deoxyribonucleoside or ribonucleoside including a molecular and/or atomic tag attached to or associated with a β and/or γ phosphate group, a base moiety, and/or a sugar moiety, where the tag alters fidelity of base incorporation.

The present invention relates to a method comprising the step of adding a composition comprising a deoxyribonucleoside or ribonucleoside including a molecular and/or atomic tag attached to or associated with a β phosphate group, a base moiety, and/or a sugar moiety, where the tag alters fidelity of base incorporation to a nucleotide polymerization medium comprising a nucleotide polymerase.

The present invention relates to a composition comprising a nucleotide or nucleotide analogs including a molecular and/or atomic tag on a β phosphate group and/or a base moiety adapted to increase the fidelity of viral replication. In another preferred composition, the virus is HIV.

The present invention relates to a method for increasing the fidelity of viral replication comprising administering an therapeutically effective amount of a nucleotide including a molecular and/or atomic tag on a β phosphate group and/or a base moiety to an animal including a human, where the nucleotide is designed to increase base incorporation fidelity during viral replication. In another preferred method, the virus is HIV.

The present invention relates to a composition comprising a viral replication fidelity enhancing agent selected from the group consisting of compounds of the following general formulas or mixtures or combinations thereof:

| | |
|---|---|
| Z-OPO$_2$O-Z' | (a) |
| Z-PO$_2$O-Z' | (b) |
| Z-OPO$_2$-Z' | (c) |
| Z-PO$_2$-Z' | (d) |
| Z-OPO$_2$—(OP(EE')O)$_n$—PO$_2$O-Z' | (e) |
| Z-OPO$_2$—(OP(EE')O)$_n$PO$_2$-Z' | (f) |
| Z-PO$_2$—(OP(EE')O)$_n$PO$_2$O-Z' | (g) |
| Z-PO$_2$—(OP(EE')O)$_n$PO$_2$-Z' | (h) | where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5, and where the agent is adapted to increase the fidelity of viral replication. In another preferred composition, the virus is HIV.

The present invention relates to a method for increasing the fidelity of viral replication comprising administering to an animal including a human a therapeutically effective amount of a viral replication fidelity enhancing agent selected from the group consisting of compounds of the following general formulas or mixtures or combinations thereof:

| | |
|---|---|
| Z-OPO$_2$O-Z' | (a) |
| Z-PO$_2$O-Z' | (b) |
| Z-OPO$_2$-Z' | (c) |
| Z-PO$_2$-Z' | (d) |
| Z-OPO$_2$—(OP(EE')O)$_n$—PO$_2$O-Z' | (e) |
| Z-OPO$_2$—(OP(EE')O)$_n$PO$_2$-Z' | (f) |
| Z-PO$_2$—(OP(EE')O)$_n$PO$_2$O-Z' | (g) |
| Z-PO$_2$—(OP(EE')O)$_n$PO$_2$-Z' | (h) | where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5, where the nucleotide is designed to increase base incorporation fidelity during viral replication. In another preferred method, the virus is HIV.

The present invention also relates to biological memory storage and retrieval systems where the fidelity of the storage and retrieve process is improved by using fidelity enhances described herein. The method would include the step of synthesizing a sequence of monomers corresponding to a given data sequence using the fidelity enhancing agent of this invention. Once the information is stored, the information can be retrieved by sequencing the sequence to retrieve the data sequence.

The present invention also relates to agents and methods for ameliorating symptoms of animals including humans infected with a retrovirus, including the step of administering to the animal a therapeutically effective amount of a composition including a dNTP having an atomic and/or molecular tag, preferably, an atomic or molecular tag on β and/or γ-tagged phosphate of the dNTP, to increase the fidelity of the viruses reverse transcriptase, decrease mutation, increase the immune response to the virus, increase the effectiveness of medications to the virus and ameliorate symptoms associated with the viral infection.

The present invention also relates to agents and methods for ameliorating symptoms of animals including humans suffering from cancer, including the step of administering to the animal a therapeutically effective amount of a composition including a dNTP having an atomic and/or molecular tag, preferably, an atomic or molecular tag on β and/or γ-tagged phosphate of the dNTP, to increase the fidelity of the patient's natural polymerases, decrease mutations, increase the immune response to the cancer, increase the effectiveness of medications to the cancer and ameliorate symptoms associated with the cancer.

The present invention also relates to agents and methods for ameliorating symptoms of aging in animals including humans, including the step of administering to the animal a therapeutically effective amount of a composition including a dNTP having an atomic and/or molecular tag, preferably, an atomic or molecular tag on β and/or γ-tagged phosphate of the dNTP, to increase the fidelity of the patient's natural polymerases, decrease mutations, increase cellular vitality, and ameliorate symptoms of aging.

The present invention also relates to agents and methods for reducing the evolutionary tendencies of retro virus such as HIV. HIV-1, the causative agent of AIDS, has evolved many ways to defeat its human host defenses. One of these ways involves evading the immune system by inaccurately replicating its genome (one mistake per 2,000–5,000 bases). The polymerase responsible for the inaccurate replication is HIV-1 reverse transcriptase (RT). RT converts the single stranded RNA genome into a complementary DNA strand, destroys the RNA template, and uses the nascent DNA strand to template synthesis of the double-stranded DNA version of the HIV-1 genome. Since the HIV genome is approximately 10,000 bases, this error-prone process produces a variant genome essential every time the virus replicates. The mis-incorporated bases can specify altered HIV protein sequences. Thus, the immune system in a patient infected with HIV is fighting a losing battle, since viral proteins (antigens) are constantly changing. Additionally, the activities of these protein variants may be modified and, if the patient is following a drug-treatment therapy, drug-resistant variants may emerge due to selective pressures. Thus, virus evolution mediated through inaccurate genome replication is a significant problem, both with HIV-1 and with any virus whose replication is mediated by an error-prone polymerase.

The fidelity of HIV-1 RT is improved in vitro by providing the enzyme with nucleotides containing a molecular tag on the γ-phosphate. This unexpected discovery may lead to a novel therapeutic that will neutralize the genetic mutability of this deadly virus. Understanding the mechanism by which RT selects nucleotides for incorporation will produce insights into enzymatic DNA synthesis and evolution of viral diversity. Ultimately, a novel therapeutic that increases enzyme fidelity may minimize antigen evolution, enabling the immune system to eliminate virus and virus infected cells, and minimize the emergence of drug resistance. Understanding why improved accuracy is observed in the context of the modified nucleotide may enable design a small molecule that has this same effect, but that would be more easily delivered into cells.

Fidelity

The inventors have found that novel nucleotides can be prepared that improve fidelity of incorporations where the nucleotides include a covalently attached substituent on β and/or γ phosphate of a NTP, dNTP or ddNTP where the substituent includes a aminonaphthalene-1-sulfonate (ANS) group. The tagged nucleotide and preferably the tagged γ-phosphate of the nucleotide improves the fidelity at which this nucleotide analog is incorporated by commercially available Taq DNA polymerase.

Pyrophosphorolysis Inhibition

Addition of pyrophosphatase to a polymerase chain reaction greatly enhances the progress of that reaction, and provides superior results compared to use of the method without a pyrophosphatase (Tabor and Richardson, 1996). Similarly addition of a pyrophosphatase to a DNA sequencing reaction provides more uniformity in intensities of bands formed in a polyacrylamide gel used to identify products of the sequencing reaction pyrophosphatase (Tabor and Richardson, 1996). This uniformity is thought to be due to prevention of degradation of specific DNA products via pyrophosphorolysis. Any modification to the nucleotide that is capable of inhibiting the pyrophosphorolysis reaction is useful in this invention. One way to inhibit pyrophosphorolysis is to break down any pyrophosphate that is generated during a polymerase reaction, by adding the enzyme pyrophosphatase. Even trace addition of a pyrophosphatase (one thousandth the molar ratio of DNA polymerase molecules in a solution) to a primer extension reaction completely stabilizes oligonucleotide fragments produced in a polymerase reaction, by preventing pyrophosphorolysis. The agent should be added at a concentration sufficient to either catalyze the hydrolysis of pyrophosphate in the reaction mixture at a rate that will prevent accumulation of pyrophosphate to a level that will lead to pyrophosphorolysis, or prevent accumulation of pyrophosphate in any other manner. The amount of agent needed is readily determined by standard techniques. However, the inventors have discovered that pyrophosphorolysis can also be reduced or eliminated by using nucleotides containing molecular and/or atomic substituents on the β and/or γ phosphate moieties.

Nucleic Acid Sequencing Using Tagged $PP_i$ Detection

In certain embodiments, the present invention provides a heterogeneous assay for the detection of released tagged pyrophosphate. The detection of tagged pyrophosphate is advantageous in a number of biological reactions. For example, in a DNA polymerase reaction, single molecule or bulk, wherein the polymerase selects a single DNA molecule from solution and thereafter incorporates the nucleotide at the 3'-end of a primer strand, the natural consequence of such incorporation is the release of pyrophosphate. If the assay solution comprises the four deoxynucleotide triphosphates, each dNTP labeled with a different molecular and/or atomic tag such as a fluorescent dye having a different color attached to the β- and/or γ-phosphate, it is then possible to sequentially record the activity of the polymerase operating on a target DNA. The nucleotide sequence of the target DNA can thereafter be directly read from the order of released dyes attached to the pyrophosphate. If the assay solution comprises the four deoxynucleotide triphosphates, each dNTP labeled with a different molecular and/or atomic tag such as a fluorescent dye having a different color attached to the β- and/or γ-phosphate and activating tags bonded to or associated with the polymerase or other species in the medium, it is then possible also to sequentially record the activity of the polymerase operating on a target DNA. The nucleotide sequence of the target DNA can thereafter be read directly from the order of released dyes attached to the pyrophosphate.

As such, the present invention provides a heterogeneous assay method for detecting pyrophosphate release, the components of the assay comprising a labeled NTP, a target nucleic acid, a primer nucleic acid and a polymerase, the method comprising: (a) flowing the labeled nucleotide triphosphate (NTP) having a molecular and/or atomic tag bonded to or associated with β- and/or γ-phosphate moiety of the NTP, past an immobilized component selected from the group consisting of the polymerase, the primer and the target nucleic acid; (b) incorporating the tagged dNTP on a primer strand hybridized to the target nucleic acid using an enzyme and releasing the γ-phosphate with the fluorophore moiety attached thereto; and (c) detecting the fluorescent moiety thereby detecting NTP binding, incorporation and/or pyrophosphate cleavage. In the heterogeneous assay of the present invention, either the polymerase, the primer or the target nucleic acid is attached to a solid phase, such as a solid support. Preferably, in the methods of the present invention, the polymerase is immobilized on a solid support.

In certain aspects, the polymerase is a DNA polymerase such as DNA polymerase I, II or III. In other aspects, suitable polymerases include, but are not limited to, a DNA dependent RNA polymerase and reverse transcriptase such as an HIV reverse transcriptase. Specific examples include, but are not limited to, T7 DNA polymerase, T5 DNA polymerase, E. coli DNA polymerase I, T4 DNA polymerase, T7 RNA polymerase and Taq DNA polymerase. Those of skill in the art will know of other enzymes or polymerases suitable for use in the present invention. In certain aspects, the polymerase is bathed in a flowing solution comprising: unlabeled, single-stranded DNA fragments hybridized to an oligonucleotide primer and a mixture of NTPs.

In certain aspects of the present invention, a labeled nucleotide triphosphate (NTP) having a molecular and/or atomic tag bonded to or associated with a β- and/or γ-phosphate moiety of the NTP is incorporated into a polynucleotide chain. The dNTP incorporation into a growing oligonucleotide by a DNA polymerase results in pyrophosphate release. In this reaction, the phosphate ester bond between the α and β phosphates of the incorporated nucleotide is cleaved by the DNA polymerase, and the β- and/or γ-phosphate moieties of the resulting pyrophosphate are released in solution. As used herein, the term pyrophosphate also includes substitution of any of the oxygen atoms of the pyrophosphate group with an atom that enables attachment of the molecular moiety that will be detected and provide information about the identity of the incorporated nucleotide, a nitrogen or a sulfur atom or combinations thereof to generate azapyrophosphate, diazapyrophosphte, thiopyrophosphate, dithiopyrophosphate, etc.

If the tag is a fluorophore, then the fluorophore can be detected either upon nucleotide binding, during incorporation or after the nucleotide and the pyrophosphate are released. In certain aspects, release of the pyrophosphate caused by cleavage of the α-β bond can switch the fluorophore moiety into a fluorescent state either by fluorophore dequenching or fluorophore activation. This event can then be detected using an ultrasensitive fluorescence detector. Using single molecule detection for example, fluorescent signals appear at the locations of the individual molecules being observed. In certain aspects, each type of nucleotide is labeled with a different fluorophore so that the incorporated nucleobases can be sequentially identified by the fluorophores during binding, incorporation or release. Preferably, the deoxy nucleotide triphosphates (dNTPs) of the present methods include, but are not limited to, deoxyadenosine triphosphate, deoxycytosine triphosphate, deoxyguanosine triphosphate, deoxythymidine triphosphate, deoxyuridine triphosphate or mixtures thereof, each with a unique molecular and/or atomic tag attached to the β- and/or γ-phosphate moiety of the NTP.

As is described in detail hereinbelow, the nucleotides of the present invention, both purine and pyrimidine varieties, are modified at various sites with a molecular and/or atomic tag such as a fluorophore or chromophore. In certain aspects, the fluorophore or chromophore are designed to interact with other tags situated on specific sites of the polymerase or associated with other agents in the medium. Once the tagged dNTPs are produced, they can be used to sequence DNA strands by direct single molecule detection. The tags can be detected when the labeled dNTP binds to the polymerase, during incorporation or upon release by measuring a detectable property of the tag alone or as a result of an interaction with another tag associated with other agent in the medium including the polymerase itself. The detectable property can of course be fluorescence or induced fluorescence. The ultrasensitivity of the present methods provide unprecedented economy and represent substantial improvements over the methods of the prior art.

The tagged dNTPs and formed tagged pyrophosphates can be used in single molecule detection formats. In certain embodiments, an unlabeled, single-stranded target nucleic acid with a primer hybridized thereto is tethered to the surface of a solid support such as a glass slide. An aqueous solution comprising an enzyme, such as a DNA polymerase, and tagged dNTPs flows across the surface. In another embodiment, an individual polymerase molecule is immobilized on a glass slide and the polymerase is bathed in a flowing solution comprising: 1) unlabeled, single-stranded DNA fragments hybridized to an oligonucleotide primer and 2) a mixture of tagged deoxynucleotide triphosphates. In yet another embodiment, a library of oligonucleotides can be immobilized on a solid support such as glass and the glass is bathed in a solution comprising: 1) a polymerizing agent such as a polymerase, 2) unlabeled, single-stranded DNA fragments hybridized to an oligonucleotide primer and 3) a mixture of tagged deoxynucleotide triphosphates. In a further embodiment, an individual polymerase molecule is immobilized on a glass slide and the polymerase is bathed in a solution comprising: 1) nicked double strained DNA, where the nicking is either affected via chemical means such as Fe-EDTA or via enzymatic means such as DNase, and 2) a mixture of tagged deoxynucleotide triphosphates.

If the tags are capable of fluoresceing or luminesceing, then an evanescent light field is set up by total internal refection (TIR) of a laser beam at the glass-aqueous solution interface. In certain aspects, the TIR illumination field is continuously imaged at video-rate with a CCD camera or an intensified charge couple device (ICCD) camera.

Solid Phase

The present invention relates to a heterogenous assay wherein a material in the solid-phase interacts with reagents in the liquid phase. In certain aspects, the nucleic acid is attached to the solid phase. The nucleic acid can be in the solid phase such as immobilized on a solid support, through any one of a variety of well-known covalent linkages or non-covalent interactions. The support is comprised of insoluble materials, such as controlled pore glass, a glass plate or slide, polystyrene, acrylamide gel and activated dextran. In other aspects, the support has a rigid or semi-rigid character, and can be any shape, e.g., spherical, as in beads, rectangular, irregular particles, gels, microspheres, or substantially flat, so long as the support permits single molecule detection. In some embodiments, it can be desirable to create an array of physically separate sequencing regions on the support with, for example, wells, microtubes or nanotubes derivatived to capture part of the DNA sequencing complex/enzyme, primer or template such as histidine 5' derivation, or other random modification so that the complex can stick to the tubes, raised regions, dimples, trenches, rods, pins, inner or outer walls of cylinders, and the like. Other suitable support materials include, but are not limited to, agarose, polyacrylamide, polystyrene, polyacrylate, hydroxyethylmethacrylate, polyamide, polyethylene, polyethyleneoxy, or copolymers and grafts of such. Other embodiments of solid-supports include small particles, non-porous surfaces, addressable arrays, vectors, plasmids, or polynucleotide-immobilizing media.

As used in the methods of the present invention, nucleic acid can be attached to the solid support by covalent bonds, or other affinity interactions, to chemically reactive functionality on the solid-supports. The nucleic acid can be attached to solid-supports at their 3', 5', sugar, or nucleobase sites. In certain embodiments, the 3' site for attachment via a linker to the support is preferred due to the many options available for stable or selectively cleavable linkers. Immobilization is preferably accomplished by a covalent linkage between the support and the nucleic acid. The linkage unit, or linker, is designed to be stable and facilitate accessibility of the immobilized nucleic acid to its sequence complement. Alternatively, non-covalent linkages such as between biotin and avidin or stepavidin are useful. Examples of other functional group linkers include ester, amide, carbamate, urea, sulfonate, ether, and thioester. A 5' or 3' biotinylated nucleotide can be immobilized on avidin or strepavidin bound to a support such as glass.

In other aspects of the heterogenous assay of the present invention, the polymerase is immobilized on a solid support. Suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

In other aspects, polymerase immobilization is accomplished using solid chromatography resins, that have been modified or activated to include functional groups that permit the covalent coupling of resin to enzyme. Typically, aliphatic linker arms are employed. The enzymes of the present invention can also be noncovalently attached to a solid support surface through, for example, ionic or hydrophobic mechanisms.

Covalent attachment of a protein or nucleic acid to a glass or metal oxide surface can be accomplished by first activating the surface with an amino silane. DNA or protein derivatized with amine-reactive functional groups can then attach to the surface (see, K. Narasimhan et al., Enzyme Microb. Technol. 7,283 (1985); M. J. Heller et al., U.S. Pat. No. 5,605,662; and A. N. Asanov et al., Anal. Chem. 70, 1156 (1998)).

The ordinarily skilled artisan will know numerous other schemes for linking nucleic acid and proteins to support surfaces. Moreover, the choice of support surface and the method of immobilizing the enzyme is largely a matter of convenience and depends on the practitioner's familiarity with, and preference for, various supports surfaces, as well as preference for various immobilizing schemes, and knowledge of the substrate.

In assay operation, the enzyme, such as a DNA polymerase, selects a single DNA molecule from solution. The polymerase incorporates a first nucleotide at the 3'-end of the primer strand and releases the respective $PP_i$. The polymerase then translocates to the next position on the target DNA, incorporates a complementary tagged nucleotide, and releases the respective pyrophophate. The tagged nucleotide can be detected upon binding to tagged polymerase, upon incorporation by tagged polymerase, and/or upon release of the tagged pyrophosphate either directly or as a result of interaction with another tag on an agent in the medium. These events can then be recorded sequentially using a detection system capable of detecting a detectable property of the tag such as by video-rate imaging using for example, a CCD or ICCD camera, capable of detecting fluorescence from a single tag where the tag is fluorophore or a chromophore. The resulting movie shows the activity of a single polymerase molecule operating on a single molecule of DNA. The nucleotide sequence of the DNA target is read directly from the order of base incorporation by detecting the tag during base binding, base incorporation and/or pyrophosphate release. Each of those events or steps during incorporation provides information about the process and a unique pattern is associated with each nucleotide. The match of each base incorporation pattern is used to increase confidence of each base call. Time, intensity and wavelength or frequency are each monitored to provide maximal confirmatory information.

When the first nucleic acid molecule has been sequenced, the polymerase releases it and selects another template from solution. Many DNA molecules are thereby sequenced by a single polymerase. The process continues for the life of the enzyme or more specifically, the life of the interacting tag within the enzyme.

To minimize signals that are not optimally positioned, assays using immobilized polymerase are preferred because once the detector system such as a CCD or ICCD camera is focused on the plane containing the polymerase, the focus will not have to be changed during a sequencing run. Otherwise, the plane of focus may need to be changed due to translocation of the polymerase through the medium as polymerization proceeded. Not only is changing the focal plane more difficult, the translocation of the polymerizing sites could result in a change in the number of polymerizing sites within a given viewing field over time and adversely affect data integrity. Moreover, the lengths of the DNA templates should preferably be significantly uniform (±10%), substantially uniform (±5%) or essentially uniform (±1%) in length to further maximize signal detection from the replication complexes.

Since there are approximately 3.4 angstroms between base pairs, a 1000 bases synthesis would involve approximately 3400 angstroms movement of either DNA through the polymerase or polymerase along the DNA. Thus, if the polymerase is immobilized and DNA is passed through the polymerase, signal remains localized at the position of the polymerase. If, however, the template or primer is immobilized, the signal produced during incorporation may move by the distance of the sequence read length. Therefore, if the DNA primer or template is immobilized, in order to minimize or eliminate overlap between the sequencing complexes it is preferred that the immobilized molecules are separated by a distance of 10 times, 5 times, or approximately the distance of the desired sequence read. By so doing, the essentially random motion of the extending strands that results from their presence in the polymerizing solution will not interfere with neighboring sequencing complexes.

Of course, computer programs could be written to analyze the data over time and correct for most of the adverse affects of polymerase translocation. Moreover, for sparsely populated sequencing reactions, the likelihood of changes in the number of active polymerizing sites per view field can be reduced.

Preparation of Target Nucleic Acid

The target nucleic acid can be prepared by various conventional methods. For example, target nucleic acid can be prepared as inserts of any of the conventional cloning vectors, including those used in conventional DNA sequencing. Extensive guidance for selecting and using appropriate cloning vectors is found in Sambrook et al., Molecular Cloning: A Laboratory Manual, Second Edition (Cold Spring Harbor Laboratory, N.Y., 1989), and like references. Sambrook et al. and Innis et al, editors, PCR Protocols (Academic Press, New York, 1990) also provide guidance for using polymerase chain reactions to prepare target polynucleotides. Cloned or PCR amplified target nucleic acid is prepared which permit attachment to solid supports.

Preferably, the target nucleic acid sequences are from sheared DNA fragments from a subject organism, preferably human, and are treated to provide blunt ends, then ligated to two oligodeoxynucleotides. For example, one oligonucleotide can be derivatized with biotin at its 5' or 3' end but the 5' end is preferred since that will cause fewer steric problems. Further, the first primer may be 5' biotinylated and the second is complementary to the biotinylated primer and contains a 5' phosphate. The ligated DNA is denatured, it is brought into contact with a streptavidin-activated slide, and it attaches through the 5' biotin to the slide. A primer is hybridized to the tethered fragments prior to sequencing. This sequencing primer is the same sequence as the biotinylated primer. Only DNA fragments having each type of ODN can both attach and be sequenced; fragments having two phosphorylated primers will not attach.

DNA attachment could also be accomplished by direct covalent coupling as practiced on DNA chips (see, U.S. Pat. No. 5,605,662). Unlike DNA chips that require a dense lawn of probes, preferably, a few DNA molecules are bound per unit surface area. Binding density is easily controlled by adding a carrier to the DNA sample (e. g., free biotin to a biotinylated DNA sample).

Detection

The tagged NTP can be detected by a variety of analytical techniques. If the tags are atomic or molecular tags with characteristic NMR, MS and/or other physical or chemical tag response signals, then the reaction can be monitored in real time using pulsed NMR techniques, MS techniques or techniques associated with other physical and/or chemical tag responses. The tags can even be shift reagents. If the tags are molecules that interact with other molecules in the presence of light to produce a fluorescent signature, then the reaction can be monitored using fluorescent spectroscopy on a continuous or discrete format. It should be recognized that tags can be prepared that have any desired detectable property.

In certain embodiments, the enzymatic reaction is monitored using single molecule detection. The single-molecule fluorescence detection of the present invention can be practiced using optical setups including near-field scanning microscopy, far-field confocal microscopy, wide-field epi-illumination, and total internal reflection fluorescence (TIRF) microscopy. Suitable photon detectors include, but are not limited to, photodiodes and intensified CCD cameras. In a preferred embodiment, an intensified charge couple device (ICCD) camera is used. The use of a ICCD camera to image individual fluorescent dye molecules in a fluid near the surface of the glass slide is advantageous for several reasons. With an ICCD optical setup, it is possible to acquire a sequence of images (movies) of fluorophores. In certain aspects, each of the NTPs of the present invention has a unique fluorophore associated with it, as such, a four-color instrument can be used having four cameras and four excitation lasers or beam-splitters may be used to monitor fluorescent intensity changes at a number of desire frequencies. Thus, it is possible to use this optical setup to sequence DNA. In addition, many different DNA molecules spread on a microscope slide can be imaged and sequenced simultaneously. Moreover, with the use of image analysis algorithms, it is possible to track the path of single dyes and distinguish them from fixed background fluorescence and from "accidentally dequenched" dyes moving into the field of view from an origin upstream.

In certain other embodiments, the sequencing works by directly detecting the release tagged pyrophosphate, where a single dNTP is feed each time and the polymerase is washed between before the next incorporation.

In certain aspects, the preferred geometry for ICCD detection of single molecules is total internal reflectance fluorescence (TIRF) microscopy. In TIRF, a laser beam totally reflects at a glass-water interface. The field does not end abruptly at the reflective interface, but its intensity falls off exponentially with distance. The thin "evanescent" optical field at the interface provides low background and enables the detection of single molecules with signal-to-noise ratios of 12:1 at visible wavelengths (see, M. Tokunaga et al., Biochem. and Biophys. Res. Comm. 235,47 (1997) and P. Ambrose, Cytometry, 36,244 (1999)).

The penetration of the field beyond the glass depends on the wavelength and the laser beam angle of incidence. Deeper penetrance is obtained for longer wavelengths and for smaller angles to the surface normal within the limit of a critical angle. In typical assays, fluorophores are detected within about 200 nm from the surface which corresponds to the contour length of about 600 base pairs of DNA. Preferably, a prism-type TIRF geometry for single-molecule imaging as described by Xu and Yeung is used (see, X-H. N. Xu et al., Science, 281,1650 (1998)).

DNA, proteins and lipids have all been detected in complex samples with single-molecule sensitivity using labeled probes (see, L. Edman et al., Proc. Natl. Acad. Sci. USA, 93,6710 (1996); M. Kinjo et al., Nucleic Acids Res. 23,1795 (1995); A. Castro and J. G. K. Williams, Anal. Chem. 69,3915 (1997); S. Nie, et al., Science 266, 1018 (1994); S. Nie, et al., Anal. Chem. 67,2849 (1995); and T. Schmidt et al., Proc. Natl. Acad. Sci. USA 9,2926 (1996)). In addition to simple detection, single fluorophores are also characterized with respect to fluorescence lifetime, spectral shifts and rotational orientation. In a preferred aspect of the present invention, an aqueous solution comprising an enzyme, such as a DNA polymerase, and distinguishable fluorogenic dNTPs, i. e., a characteristic dye for each nucleobase, flows across the surface. An evanescent light field is set up by total internal refection (TIR) of a laser beam at the glass-aqueous solution interface. In certain aspects, the TIR illumination field is continuously imaged at video-rate with an intensified charge couple device (ICCD) camera. It is thus possible to image the pyrophosphate as it is hydrolyzed by the enzyme.

Upon incorporation by polymerase, the tagged dNTP is hydrolyzed as usual and the liberated tagged pyrophosphate diffuses into the surrounding medium. The tagged dNTP can be detected upon binding, incorporation or release or the free tagged pyrophosphate can be detected by detecting the detectable property of the tag such as fluorescent and its appearance is imaged at video-rate under a microscope. A flowing stream sweeps the dye away from the parent DNA molecule. As the DNA molecule continues to move through the polymerase due to the immobilized polymerase, the nucleotide sequence is read from the order of released dyes. Sequencing proceeds quickly, as fast as the polymerase progresses along the DNA template.

In another embodiment, the present invention includes sensors as disclosed in U.S. Pat. No. 5,814,524 which issued to Walt et al., on Sep. 29, 1998, incorporated herein by reference. An optical detection and identification system is disclosed therein that includes an optic sensor, an optic sensing apparatus and methodology for detecting and evaluating one or more analytes or ligands of interest, either alone or in mixtures. The system is comprised of a supporting member and an array formed of heterogeneous, semi-selective polymer films which function as sensing receptor units and are able to detect a variety of different analytes and ligands using spectral recognition patterns. Using this system, it is possible to combine viewing and chemical sensing with imaging fiber chemical sensors.

High Throughput Screening

The present invention also provides integrated systems for high-throughput screening of DNA sequencing and pyrophosphate detection. The systems typically include robotic armature which transfers fluid from a source to a destination, a controller which controls the robotic armature, an ICCD camera, a data storage unit which records the detection, and an assay component such as a microtiter dish or a substrate comprising a fixed reactant. A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96, 384 or more welled microtiter plates to set up several parallel simultaneous polymerase reactions.

Optical images viewed (and, optionally, recorded) by a camera or other recording device (e.g., a photodiode and data storage device) are optionally further processed in any of the embodiments herein, e. g., by digitizing the image and storing and analyzing the image on a computer. A variety of commercially available peripheral equipment and software is available for digitizing, storing and analyzing a digitized video or digitized optical image. In certain aspects, the integrated system of the present invention carries light from the specimen field to the charge-coupled device (CCD) camera, which includes an array of picture elements (pixels). The light from the specimen is imaged on the CCD camera. Particular pixels corresponding to regions of the specimen (e. g., individual polymerase sites on a glass surface) are sampled to obtain light intensity readings for each position. Multiple pixels are processed in parallel to increase speed. The apparatus and methods of the invention are easily used for viewing any sample, e.g., by fluorescent or dark field microscopic techniques.

There is a great deal of practical guidance available in the literature for providing an exhaustive list of fluorescent and chromogenic molecules and their relevant optical properties (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing fluorophore and quencher molecules for covalent attachment via common reactive groups that can be added to a nucleotide, as exemplified by the following references: Haugland (supra); Ullman et al., U.S. Pat. No.3,996,345; Khanna et al., U.S. Pat. No. 4,351,760, incorporated herein by reference.

Suitable donors and acceptors operating on the principle of fluorescence energy transfer (FRET) include, but are not limited to, 4-acetamido-4'isothiocyanatostilbene-2,2'disulfonic acid; acridine and derivatives: acridine, acridine isothiocyanate; 5- (2'-aminoethyl) aminonaphthalene-1-sulfonic acid (EDANS); 4-amino-3-vinylsulfonyl)phenyl] naphthalimide-3,5 disulfonate; -(4-anilino-lnaphthyl)maleimide; anthranilamide; BODIPY; Brilliant Yellow; coumarin and derivatives: coumarin, 7-amino-4-methylcoumarin (AMC, Coumarin 120), 7-amino-4trifluoromethylcouluarin (Coumaran 151); cyanine dyes; cyanosine; 4', 6-diaminidino-2phenylindole (DAPI); 5', 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'diisothiocyanatostilbene-2,2'-disulfonic acid; 5-dimethylamino naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5carboxyfluorescein (FAM), 5-(4, 6-dichlorotriazin-2-yl) aminofluorescein (DTAF), 2', 7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (CibacronTM Brilliant Red 3B-A) rhodamine and derivatives: 6-carboxy-X-rhodamine (ROX), 6carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N, N, N', N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

In certain embodiments, certain visible and near IR dyes are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and can be used to practice the present invention.

There are many linking moieties and methodologies for attaching fluorophore or quencher moieties to nucleotides, as exemplified by the following references: Eckstein, editor, Oligonucleotides and Analogues: A Practical Approach (IRL Press, Oxford, 1991); Zuckerman et al., Nucleic Acids Research, 15: 5305–5321 (1987) (3'thiol group on oligonucleotide); Sharma et al., Nucleic Acids Research, 19: 3019 (1991) (3'sulfhydryl); Giusti et al., PCR Methods and Applications, 2: 223–227 (1993) and Fungetal., U.S. Pat. No. 4,757,141 (5'phosphoamino group via AminolinkTM II available from Applied Biosystems, Foster City, Calif.) Stabinsky, U.S. Pat. No. 4,739,044 (3'aminoalkylphosphoryl group); AP3 Labeling Technology (U.S. Pat. Nos. 5,047,519 and 5,151,507, assigned to E. I. DuPont de Nemours & Co); Agrawal et al., Tetrahedron Letters, 31:1543–1546 (1990) (attachment via phosphoramidate linkages); Sproat et al., Nucleic Acids Research, 15: 4837 (1987) (5'mercapto group); Nelson et al., Nucleic Acids Research, 17: 7187–7194 (1989) (3'amino group); and the like.

Primer Extension Reaction

Generally, the primer extension reaction of the present invention comprises the following steps: (i) providing a template nucleic acid; (ii) annealing an oligonucleotide primer to a portion of the template nucleic acid thereby forming a primer-template hybrid; (iii) adding primer-extension reagents to the primer-template hybrid for extending the primer; and (iv) optionally adding a cosubstrate-enzyme pair to the primer-template hybrid for conducting a pyrophosphate-utilizing reaction.

Any source of nucleic acid can be used as a template nucleic acid provided it can be presented in a single stranded form and is capable of annealing with a primer oligonucleotide. Exemplary template nucleic acids include DNA, RNA, which DNA or RNA may be single stranded or double stranded. More particularly, template nucleic acid may be genomic DNA, messenger RNA, cDNA, DNA amplification products from a PCR reaction, and the like. Methods for preparation of template DNA may be found elsewhere (ABI PRISM Dye Primer Cycle Sequencing Core Kit). Standard protocols for primer-template annealing and primer extension in the context of PCR or Sanger-type sequencing may be found elsewhere (Innis; Deiffenbach; ABI PRISM Dye Primer Protocol; ABI PRISM Dye Terminator Protocol). Generally, to perform a primer extension reaction in the context of PCR, template nucleic acid is mixed with a pair of PCR primers and primer-extension reagents comprising a buffer, $MgCl_2$, deoxynucleotide triphosphates or preferably for increase accuracy of the amplification products, $\beta$ and/or $\gamma$ tagged dNPTs, and a DNA polymerase. For example, a typical PCR reaction includes 20 pmol of each primer, 20 mM buffer at pH 8, 1.5 mM $MgCl_2$, 10 to 500 $\mu$M, preferably 200 $\mu$m, of each deoxynucleotide triphosphate (dNTP), and 2 units of Taq polymerase or other suitable thermostable polymerase.

The reaction mixture is then thermocycled, a typical thermocycle profile comprising a denaturation step (e.g. 96° C., 15 s), a primer annealing step (e.g., 55° C., 30 s), and a primer extension step (e.g., 72° C., 90 s). Typically, the thermocycle is repeated from about 10 to about 100 cycles or more.

Kits and Solutions of the Invention

In another aspect, the present invention includes kits and solutions for performing the primer extension methods of the invention. The kits and solutions of the invention include primer extension reagents with the modified (tagged) dNTPs and/or modified $PP_i$ and optionally a cosubstrate-enzyme pair. Optionally, the kits may also include primers. The elements of the kits may be packaged in a single container or multiple containers. In one preferred configuration, a polymerase enzyme and modified (tagged) dNTPs and/or modified $PP_i$ are packaged in the same container.

This invention may also be used in methods where improvement of the accuracy of the synthesis of nucleic acids by a polymerase is desired and where pyrophosphorolysis is deemed counter-productive. Uses include: polymerase chain reaction, especially 'Long PCR,' and cDNA synthesis. Examples of patents describing these methods include U.S. Pat. Nos. 4,965,188, US 5,079,352, US 5,091,310, US 5,142,033, US 4,683,195, US 4,683,202, US 4,800,159, US 5,512,462 and US 5,405,776, incorporated by reference. In the case of cDNA synthesis, a reverse transcriptase polymerase is incubated with the mRNA template and the tagged deoxynucleoside triphosphates.

The invention also relates to a kit comprising a container means, such as a box, having in close confinement therein two or more containers such as vials, ampules, tubes, jars or the like, each of which contains the materials necessary to carry out the invention. For example, a container may contain a polymerizing agent such as a DNA or RNA polymerase. Another container may contain a tagged phosphate, pyrophosphate or polyphosphate in an amount sufficient to reduce, inhibit or prevent pyrophosphorolysis. And other containers may contain tagged and/or untagged dNTPs. Alternatively, the kit can include a container containing a polymerizing agent such as a DNA or RNA polymerase and other containers containing tagged and/or untagged dNTPs.

Preferably, the contents of the containers are present at working concentrations or requiring a to fold dilution to achieve working concentrations. Other containers may contain other reagents that are necessary for carrying out dideoxy sequencing or amplification (PCR).

Thus, the solution of the present invention is an aqueous and/or buffered liquid containing the components described above. These components are present in the solution at concentrations sufficient to perform their desired function. If the reaction mixture is intended to amplify a target nucleic acid molecule, the reaction mixture will contain the tagged dNTPs which reduce the level of pyrophosphate and increase polymerase fidelity, a polymerizing agent such as a DNA polymerase, all four dNTPs, and one or more oligonucleotide primers having a single stranded region which are capable of annealing to the target nucleic acid molecule, being extended and thereby amplified. The primer extension reaction may also comprise a chain terminator as described herein, e.g., a dideoxynucleoside triphosphate and the ddNTP may be modified at the $\beta$ and/or $\gamma$ phosphate to reduce background and/or reduce band spreading, which allows for sequencing of the target DNA molecule by the well known Sanger dideoxy sequencing method.

The present invention uses tagged NTPs that having molecular and/or atomic tags bonded to or associated with the $\beta$ and $\gamma$ phosphates so as not to alter the chemistry of the growing polymer chain, allow for detection of the NTPs (including dNTPs and ddNTPs) upon binding, during incorporation and after incorporation via the released tagged pyrophosphate. Optionally, the present invention can include phosphatases that degrade NTPs (including dNTPs and ddNTPs) or that degrade pyrophosphate. However, when the labeled pyrophosphates act to inhibit pyrophosphorolysis, then such degradation enzymes should be tailored to attach the NTPs and not the tagged pyrophosphate.

Detailed nucleoside di- and/or mono-phosphate degrading enzymes are optional and may be used in combination with a nucleoside tri-phosphate degrading enzyme. Suitable such enzymes include most notably apyrase which is both a nucleoside diphosphatase and triphosphatase, catalyzing the reactions NTP→NMP+2Pi and NTP→NDP+Pi (where NTP is a nucleoside triphosphate, NDP is a nucleoside diphospate, NMP is a nucleotide monophosphate and Pi is phosphate). Apyrase may be obtained from Sigma Chemical Company.

Other suitable nucleotide triphosphate degrading enzymes include Pig Pancreas nucleoside triphosphate diphosphohydrolase (Le Bel et al., 1980, J. Biol. Chem., 255, 1227–1233). Further enzymes are described in the literature.

Different combinations of nucleoside tri-, di- or monophosphatases may be used. Such enzymes are described in the literature and different enzymes may have different characteristics for deoxynucleotide degradation, e.g., different Km, different efficiencies for a different nucleotides etc. Thus, different combinations of nucleotide degrading enzymes may be used, to increase the efficiency of the nucleotide degradation step in any given system. For example, in some cases, there may be a problem with contamination with kinases which may convert any nucleoside diphosphates remaining to nucleoside triphosphates, when a further nucleoside triphosphate is added. In such a case, it may be advantageous to include a nucleoside disphosphatase to degrade the nucleoside diphosphates. Advantageously all nucleotides may be degraded to nucleosides by the combined action of nucleoside tri-, di- and monophosphatases.

Generally speaking, the nucleotide-degrading enzyme is selected to have kinetic characteristics relative to the polymerase such that nucleotides are first efficiently incorporated by the polymerase, and then any non-incorporated nucleotides are degraded. Thus, for example, if desired, the $K_m$ of the nucleotide-degrading enzyme may be higher than that of the polymerase such that nucleotides which are not incorporated by the polymerase are degraded. This allows the sequencing procedure to proceed without washing the template between successive nucleotide additions. A further advantage is that since washing steps are avoided, it is not necessary to add new enzymes eg. polymerase with each new nucleotide addition, thus improving the economy of the procedure. Thus, the nucleotide-degrading enzyme or enzymes are simply included in the polymerase reaction mix, and a sufficient time is allowed between each successive nucleotide addition for degradation of substantially most of the unincorporated nucleotides.

The amount of nucleotide-degrading enzyme to be used, and the length of time between nucleotide additions may readily be determined for each particular system, depending on the reactants selected, reaction conditions etc.

As mentioned above, the nucleotide-degrading enzyme(s) may be included during the polymerase reaction step. This may be achieved simply by adding the enzyme(s) to the polymerase reaction mixture prior to, simultaneously with or after the polymerase reaction (ie. the chain extension or nucleotide incorporation) has taken place, e.g. prior to, simultaneously with, or after, the polymerase and/or nucleotides are added to the sample/primer.

In one embodiment, the nucleotide-degrading enzyme(s) may simply be included in solution in a reaction mix for the polymerase reaction, which may be initiated by addition of the polymerase or nucleotide(s). Alternatively, the nucleotide-degrading enzyme(s) may be immobilized on a solid support, e.g. a particulate solid support (e.g. magnetic beads) or a filter, or dipstick etc. and it may be added to the polymerase reaction mixture at a convenient time. For example, such immobilized enzyme(s) may be added after nucleotide incorporation (i.e., chain extension) has taken place, and then, when the incorporated nucleotides are hydrolyzed, the immobilized enzyme may be removed from the reaction mixture (e.g. it may be withdrawn or captured, e.g., magnetically in the case of magnetic beads), before the next nucleotide is added. The procedure may then be repeated to sequence more bases.

Such an arrangement has the advantage that more efficient nucleotide degradation may be achieved as it permits more nucleotide degrading enzyme to be added for a shorter period. This arrangement may also facilitate optimization of the balance between the two competing reactions of DNA polymerization and nucleotide degradation.

In a further embodiment, the immobilization of the nucleotide-degrading enzyme may be combined with the use of the enzyme(s) in solution. For example, a lower amount may be included in the polymerase reaction mixture and, when necessary, nucleotide-degrading activity may be boosted by adding immobilized enzyme as described above. The term dideoxynucleotide as used herein includes all 2'-deoxynucleotides in which the 3'-hydroxyl group is absent or modified and thus, while able to be added to the primer in the presence of the polymerase, is unable to enter into a subsequent polymerization reaction.

The method of the invention may readily be modified to enable the sequencing (ie. base incorporation) reactions to be continuously monitored in real time. This may simply be achieved by performing the chain extension and detection, or signal-generation, reactions substantially simultaneously by monitoring a detectable property of the tags on the NTPs during binding, incorporation, and/or pyrophosphate release.

The sample DNA (i.e., DNA template) may conveniently be single-stranded, and may either by immobilized on a solid support or in solution. The use of a nucleotide degrading enzyme according to the present invention means that it is not necessary to immobilize the template DNA to facilitate washing, since a washing step is no longer required. By using thermostable enzymes, double-stranded DNA templates might also be used. The sample DNA may be provided by any desired source of DNA, including for example PCR or other amplified fragments, inserts in vectors such as M13 or plasmids.

In order to repeat the method cyclically and thereby sequence the sample DNA and, also to aid separation of a single stranded sample DNA from its complementary strand, the sample DNA may optionally be immobilized or provided with means for attachment to a solid support. Moreover, the amount of sample DNA available may be small and it may therefore be desirable to amplify the sample DNA before carrying out the method according to the invention.

The sample DNA may be amplified, and any method of amplification may be used, for example in vitro by PCR, rolling circle, or Self Sustained Sequence Replication (3SR) or in vivo using a vector and, if desired, in vitro and in vivo amplification may be used in combination. Whichever method of amplification is used the procedure may be modified that the amplified DNA becomes immobilized or is provided with means for attachment to a solid support. For example, a PCR primer may be immobilized or be provided with means for attachment to a solid support. Also, a vector may comprise means for attachment to a solid support adjacent the site of insertion of the sample DNA such that the amplified sample DNA and the means for attachment may be excised together.

Immobilization of the amplified DNA may take place as part of PCR amplification itself, as where one or more primers are attached to a support, or alternatively one or more of the PCR primers may carry a functional group permitting subsequent immobilization, eg. a biotin or thiol group. Immobilization by the 5' end of a primer allows the strand of DNA emanating from that primer to be attached to a solid support and have its 3' end remote from the support and available for subsequent hybridization with the extension primer and chain extension by polymerase.

The solid support may conveniently take the form of microtitre wells, which are advantageously in the conventional 8×12 format, or dipsticks which may be made of polystyrene activated to bind the primer DNA (K Almer, Doctoral Theses, Royal Institute of Technology, Stockholm, Sweden, 1988). However, any solid support may conveniently be used, including any of the vast number described in the art, e.g., for separation/immobilization reactions or solid phase assays. Thus, the support may also comprise particles, fibers or capillaries made, for example, of agarose, cellulose, alginate, Teflon or polystyrene. Magnetic particles eg the superparamagnetic beads produced by Dynal AS (Oslo, Norway) also may be used as a support.

The solid support may carry functional groups such as hydroxyl, carboxyl, aldehyde or amino groups, or other moieties such as avidin or streptavidin, for the attachment of primers. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

Another aspect of this invention is the use of tagged nucleotides to directly sequence populations of DNA molecules in synchrony. The synchrony is achieved by applying a population of single tagged dNTP to the reaction chamber, monitoring $PP_i$ release (as per tag detection), and removing unincoporated dNTPs prior to applying the next tagged dNTP until the sequence of interest in determined.

The tagged NTPs and/or pyrophosphate detection method of the present invention thus opens up the possibility for an automated approach for large-scale, non-elecrophoretic sequencing procedures, which allow for continuous measurement of the progress of the polymerization reaction with time. The method of the invention also has the advantage that multiple samples may be handled in parallel. The target DNA may be cDNA synthesized from RNA in the sample and the method of the invention is thus applicable to diagnosis on the basis of characteristic RNA. Such preliminary synthesis can be carried out by a preliminary treatment with a reverse transcriptase, conveniently in the same system of buffers and bases of subsequent PCR steps if used. Since the PCR procedure requires heating to effect strand separation, the reverse transcriptase will be inactivated in the first PCR cycle. When mRNA is the sample nucleic acid, it may be advantageous to submit the initial sample, e.g. a serum sample, to treatment with an immobilized polydT oligonucleotide in order to retrieve all mRNA via the terminal polyA sequences thereof. Alternatively, a specific oligonucleotide sequence may be used to retrieve the RNA via a specific RNA sequence. The oligonucleotide can then serve as a primer for cDNA synthesis, as described in WO 89/0982. Of course, the methods of the present invention can be used with any source of purified cDNA and RNA.

The present invention also relates to using a modified nucleotide to increase fidelity either alone (in a reaction with Taq DNA polymerase or any enzyme that joins nucleic acid monomers) or in combination with a naturally occurring, high-fidelity polymerase or one that is genetically modified for high-fidelity synthesis. Additionally, the inventors have designed a complementary system using tagged nucleotides, either alone or in combination, with a naturally occurring low-fidelity polymerase or one that is genetically modified for low-fidelity synthesis. The purpose of this embodiment is to enable either random mutagenesis of a particular nucleic acid or targeted mutagenesis of a particular base type alone the length of the nucleic acid polymer. At times, it is desirable to synthesize a nucleic acid polymer at reduced accuracy (essentially a random mutagenesis). In this system, a single or a subset of natural nucleotides (that produced reduced fidelity synthesis), or ratio thereof, can be used to more precisely target mutagenesis of desired nucleotide type along the length of the nucleic acid polymer.

Advantageously, the extension primer is sufficiently large to provide appropriate hybridization with the sequence immediately 5' of the target position, yet still reasonably short in order to avoid unnecessary chemical synthesis. It will be clear to persons skilled in the art that the size of the extension primer and the stability of hybridization will be dependent to some degree on the ratio of A-T to C-G base pairings, since more hydrogen bonding is available in a C-G pairing.

The present invention also relates to improving polymerase base incorporation fidelity acting on a target nucleic acid sequence to which a primer library (pre-existing primer set), where the library comprises an optimized subset of base permutations and combinations of the four bases for a base length between about 6 and about 35 bases. The inventors have developed a robust "classic" sequencing strategy using octamer primers to initiate the DNA synthesizing reaction (Hardin et al. U.S. Pat. No. 6,083,695, incorporated herein by reference) The primers comprising an octamer library are also appropriate to initiate single molecule DNA sequencing and related techniques with the modified nucleotides. As an example, by contacting a target nucleic acid sequence with such a library, complementary library primers will bind to the sequence forming a site for polymerase binding and polymerization. If more than one primer binds, then the polymerase will randomly select and bind to a given primer complemented to a local on the sequence and polymerization will commence. Although it is possible to have two primer molecules bound on a single template, only one primer will be the site of polymerase activity. The increased fidelity will ensure superior library differentiation. Alternatively, the library members can contain a 5' extension to enable their immobilization to a surface, while still retaining the ability to form at least an 8 base duplex with the template, the unknown nucleic acid sequence (template) added to the surface and then the polymerase and polymerizing components are added to initiate polymerization with improved fidelity through the tagged dNTPs or by the addition of a phosphorolysis inhibitors of this invention.

Also, the skilled person will consider the degree of homology between the extension primer to other parts of the amplified sequence and choose the degree of stringency accordingly. Guidance for such routine experimentation can be found in the literature, for example, Molecular Cloning: a laboratory manual by Sambrook, J., Fritsch E. F. and Maniatis, T. (1989). It may be advantageous to ensure that the sequencing primer hybridizes at least one base inside from the 3' end of the template to eliminate blunt-ended DNA polymerase activity. If separate aliquots are used (i.e., 4 aliquots, one for each base), the extension primer is preferably added before the sample is divided into four aliquots although it may be added separately to each aliquot. It should be noted that the extension primer may be identical with the PCR primer but preferably it is different, to introduce a further element of specificity into the system.

Alternatively, can have multiple (individual oligonucleotides such as octamers) on surface where polymerization starts when a polymerizing agent such as a polymerase and the reaction components are added.

Additionally, primase may be used to synthesize an RNA primer that can subsequently be used by a DNA polymerase to begin DNA synthesis. The site of initiation of the RNA chain is not critical and many reactions can be processed in parallel to obtain the complete DNA sequence.

The polymerase reaction in the presence of the extension primer and a deoxynucleotide is carried out using a polymerase which will incorporate dideoxynucleotides, e.g. T7 polymerase, Klenow or Sequenase Ver. 2.0 (USB U.S.A.). Any suitable chain extension sometimes are digested by an exonuclease activity. If such reverse polymerization occurs in the method according to the invention the level of background noise increases. In order to avoid this problem, a nonproofreading polymerase, eg. exonuclease deficient (exo-) Klenow polymerase may be used. Otherwise it is desirable to add fluoride ions or nucleotide monophosphates which suppress 3' digestion by polymerase. The precise reaction conditions, concentrations of reactants etc. may readily be determined for each system according to choice. However, it may be advantageous to use an excess of polymerase over primer/template to ensure that all free 3' ends are extended.

In the method of the invention there is a need for a DNA polymerase with high efficiency in each extension step due to the rapid increase of background signal which may take place if templates which are not fully extended accumulate. An induced-fit binding mechanism in the polymerization step selects very efficiently for binding of the correct dNTP with a net contribution towards fidelity of $10$–$10^6$. Exonuclease deficient polymerases, such as (exo-) Klenow or Sequenase 2.0, catalyze incorporation of a nucleotide only when the complementary dNTP was present, confirming a high fidelity of these enzymes even in the absence of proof-reading exonuclease activity.

In certain circumstances, e.g. with longer sample templates, it may be advantageous to use a polymerase which has a lower Km for incorporation of the correct (matched) nucleotide, than for the incorrect (mismatched) nucleotide. This may improve the accuracy and efficiency of the method.

In many diagnostic applications, for example genetic testing for carriers of inherited disease, the sample will contain heterozygous material, that is half the DNA will have one nucleotide at the target position and the other half will have another nucleotide. Thus if four aliquots are used in an embodiment according to the invention, two will show a negative signal and two will show half the positive signal. It will be seen therefore that it is desirable to quantitatively determine the amount of signal detected in each sample.

Also, it will be appreciated that if two or more of the same base are adjacent the 3'-end of the primer a larger signal will be produced. In the case of a homozygous sample it will be clear that there will be three negative and one positive signal when the sample is in four aliquots.

Further to enhance accuracy of the method, bidirectional sequencing ie. sequencing of both strands of a double-stranded template may be performed. This may be advantageous e.g. in the sequencing of heterozygous material. Conveniently, this may be achieved by immobilizing the double-stranded sample template by one strand, e.g. on particles or in a microtitre well, eluting the second strand and subjecting both strands separately to a sequencing reaction by the method of the invention.

Reaction efficiency may be improved by including $Mg^{2+}$ ions in the reagent (NTP and/or polymerase) solutions. It will be appreciated that when the target base immediately 3'- of the primer has an identical base 3'- thereto, and the polymerization is effected with a deoxynucleotide (rather than a dideoxynucleotide) the extension reaction will add two bases at the same time and indeed any sequence of successive identical bases in the sample will lead to simultaneous incorporation of corresponding bases into the primer. However, the amount of pyrophosphate liberated will clearly be proportional to the number of incorporated bases so that there is no difficulty in detecting such repetitions. Since the primer is extended by a single base by the procedure described above (or a sequence of identical bases), the extended primer can serve in exactly the same way in a repeated procedure to determine the next base in the sequence, thus permitting the whole sample to be sequenced.

As mentioned above, in the method of the invention, different tagged deoxy- or dideoxynucleotides may be added to separate aliquots of sample-primer mixture or successively to the same sample-primer mixture. This covers the situations where both individual and multiple target DNA samples are used in a given reaction, which sample DNAs may be the same or different. Thus, for example, as will be discussed in more detail below, in certain embodiments of the invention, there may be one reaction in one container, (in the sense of one sample DNA, ie. one target DNA sequence, being extended) whereas in other embodiments different primer-sample combinations may be present in the same reaction chamber, but kept separate by e.g. area-selective immobilization.

The present invention provides two principal methods of sequencing immobilized DNA.

The invention provides a first method of sequencing sample DNA wherein the sample DNA is subjected to amplification; the amplified DNA is optionally immobilized and then subjected to strand separation, one strand eg. the optionally non-immobilized or immobilized strand being removed (i.e., either strand may be sequenced), and an extension primer is provided, which primer hybridizes to the sample DNA immediately adjacent that portion of the DNA to be sequenced; each of four aliquots of the single stranded DNA is then subjected to a polymerase reaction in the presence of a tagged deoxynucleotide, each aliquot using a different tagged deoxynucleotide whereby only the tagged deoxynucleotide complementary to the base in the target position becomes incorporated; the tagged pyrophosphate released by base incorporation being identified. After identification of the incorporated nucleotide a nucleotide degrading enzyme is added, e.g., a phosphatase such as snake venom phosphatase, calf intestinal phosphatase, shrimp alkaline phosphatase, or bacterial alkaline phosphatase. Upon separating the nucleotide degrading enzyme from the different aliquots, for example if it is immobilized on magnetic beads, the four aliquots can be used in a new cycle of nucleotide additions, only if the other three are also extended by addition of the correct dNTP (after which, only one could be extended). This procedure can then be continuously repeated.

The invention also provides a second method of sequencing sample DNA wherein the sample DNA is subjected to amplification; the amplified DNA is optionally immobilized and then subjected to strand separation, one strand, e.g., the optionally non immobilized or immobilized strand being removed, and an extension primer is provided, which primer hybridizes to the sample DNA immediately adjacent to that portion of the DNA to be sequenced; the single stranded DNA is then subjected to a polymerase reaction in the presence of a first tagged deoxynucleotide, and the extent of tagged pyrophosphate release is determined, non-incorporated nucleotides being degraded by the nucleotide-degrading enzyme, and the reaction being repeated by successive addition of a second, third and fourth tagged deoxynucleotide until a positive release of pyrophosphate indicates incorporation of a particular tagged deoxynucleotide into the primer, whereupon the procedure is repeated to extend the primer one base (or one base-type) at a time and to determine the base which is immediately 3'- of the extended primer at each stage.

The present invention also provides a step by step polymerization apparatus and method. The apparatus and method includes a tubular member including a zone containing an immobilized polymerizing agent such as a polymerase. The zone is pre-treated by a nucleotide sequence. A plug of solution containing a polymerization reaction mixture containing tagged dNTPs, where each dNTP has a different tag having a different value for a specific detectable property such as absorption coefficient or fluresceing frequency and where the tag are bonded to or associated with the β and/or γ phosphate of the triphosphate moiety. After a specified period of time, a plug of inert buffer is moved into the tubular member to displace the reactive solution. As the reactive solution is moved out of the reaction zone, the solution is exposed to a detection procedure that detects the specific detectable property to determine the incorporated dNTP. The wash plug should generally be several multiples of the volume of solution necessary to cover the reaction zone. Another reactive medium plug then follows, followed by a wash plug which allows detection of the next incorporation and so on and so on. Alternatively, the reaction media can include only a single dNTP and the detector looks for free tagged pyrophosphate. Each of these step-by-step polymerization methods is amenable of microarray configuration. Additionally, for the single dNTP apparatus and method, combinatorial mathematics can be used to determine the best choice for the next dNTP plug to use.

An alternative format for the analysis is to use an array format wherein samples are distributed over a surface, for example a micro-fabricated chip, and thereby an ordered set of samples may be immobilized in a 2dimensional (2D) format. Many samples can thereby be analyzed in parallel. Using the method of the invention, many immobilized templates may be analyzed in this way by allowing the solution containing the enzymes and one nucleotide to flow over the surface and then detecting the signal produced for each sample. This procedure can then be repeated. Alternatively, several different oligonucleotides complementary to the template may be distributed over the surface followed by hybridization of the template. Incorporation of tagged deoxynucleotides or tagged dideoxynucleotides may be monitored for each oligonucleotide by the signal produced using the various oligonucleotides as primer. By combining the signals from different areas of the surface, sequence-based analyses may be performed by four cycles of polymerase reactions using the various tagged dideoxynucleotides.

Two-stage PCR (using nested primers), as described in application WO90/11369, may be used to enhance the signal to noise ratio and thereby increase the sensitivity of the method according to the invention. By such preliminary amplification, the concentration of target DNA is greatly increased with respect to other DNA which may be present in the sample and a second-stage amplification with at least one primer specific to a different sequence of the target DNA significantly enhances the signal due to the target DNA relative to the 'background noise'.

Any suitable polymerase may be used, although it is preferred to use a thermophilic enzyme such as Taq polymerase to permit the repeated temperature cycling without having to add further polymerase, e.g. Klenow fragment, in each cycle of PCR. PCR has been discussed above as a preferred method of initially amplifying target DNA although the skilled person will appreciate that other methods may be used instead of in combination with PCR. A recent development in amplification techniques which does not require temperature cycling or use of a thermostable polymerase is Self Sustained Sequence Replication (3SR) or rolling circle amplification. 3SR is modelled on retroviral replication and may be used for amplification (see for example Gingeras, T. R. et al PNAS (USA) 87:1874–1878 and Gingeras, T. R. et al PCR Methods and Applications Vol. 1, pp 25–33). Rolling circle amplification is described in more detail in U.S. Pat. No. ***, incorporated herein by reference.

As indicated above, the method can be applied to identifying the release of tagged pyrophosphate when dideoxynucleotide residues are incorporated into the end of a DNA chain. The present invention also relates to a method of identification of the base in a single target position in a DNA sequence (mini-sequencing) wherein sample DNA is subjected to amplification; the amplified DNA is immobilized and then subjected to strand separation, the non-immobilized strand being removed and an extension primer, which hybridizes to the immobilized DNA immediately adjacent to the target position, is provided; each of four aliquots of the immobilized single stranded DNA is then subjected to a polymerase reaction in the presence of a dideoxynucleotide, each aliquot using a different dideoxynucleotide whereby only the dideoxynucleotide complementary to the base in the target position becomes incorporated and, because the tagged nucleotides improve the fidelity of incorporation, the signals from the other nucleotides are at background; the four aliquots are then subjected to extension in the presence of all four deoxynucleotides, whereby in each aliquot the DNA which has not reacted with the dideoxynucleotide is extended to form double stranded DNA while the dideoxy-blocked DNA remains as single stranded DNA; followed by identification of the double stranded and/or single stranded DNA to indicate which dideoxynucleotide was incorporated and hence which base was present in the target position. Clearly, the release of tagged pyrophosphate in the chain terminating dideoxynucleotide reaction will indicate which base was incorporated but the relatively large amount of tagged pyrophosphate released in the subsequent deoxynucleotide primer extension reactions (so-called chase reactions) gives a much larger signal and is thus more sensitive.

It will usually be desirable to run a control with no dideoxynucleotides and a 'zero control' containing a mixture of all four dideoxynucleotides. WO93/23562 defines the term 'dideoxynucleotide' as including 3'-protected 2'-deoxynucleotides which act in the same way by preventing further chain extension. However, if the 3' protecting group is removable, for example by hydrolysis, then chain extension (by a single base) may be followed by unblocking at the 3' position, leaving the extended chain ready for a further extension reaction. In this way, chain extension can proceed one position at a time without the complication which arises with a sequence of identical bases, as discussed above.

Thus, the methods A and B referred to above can be modified whereby the base added at each stage is a 3'protected 2'-deoxynucleotide and after the base has been added (and the tag signal or detectable property such as light emission is detected), the 3'-blocking group is removed to permit a further 3'-protected - 2'deoxynucleotide to be added. Suitable protecting groups include acyl groups such as alkanol groups e.g. acetyl or indeed any hydroxyl protecting groups known in the art, for example as described in Protective Groups in Organic Chemistry, J F W McOnie, Plenum Press, 1973.

The invention, in the above embodiment, provides a simple and rapid method for detection of single base changes. In one format it successfully combines two techniques: solid-phase technology (DNA bound to magnetic beads) and detection of a detectable property associated with the tags on the dNTPs or released $PP_i$. The method can be used to both identify and quantitate selectively amplified DNA fragments. It can also be used for detection of single base substitutions and for estimation of the heterozygosity index for an amplified polymorphic gene fragment. This means that the method can be used to screen for rare point mutations responsible for both acquired and inherited diseases, identify DNA polymorphisms, and even differentiate between drug-resistant and drug-sensitive strains of viruses or bacteria without the need for centrifugations, filtrations, extractions or electrophoresis. The simplicity of the method renders it suitable for many medical (routine analysis in a wide range of inherited disorders) and commercial applications.

The positive experimental results presented below clearly show the method of the invention is applicable to an on-line automatic non-electrophoretic DNA sequencing approach, with step-wise incorporation of single deoxynucleotides. After amplification to yield single-stranded DNA and annealing of the primer, the template/primer-fragment is used in a repeated cycle of dNTP incubations. Samples are continuously monitored for a detectable property of the tagged PPi such as fluorescence. As the synthesis of DNA is accompanied by release of tagged pyrophosphate (PPi) in an amount equal to the amount of nucleotide incorporated, signals derived from the detectable property of the tag are observed only when complementary bases are incorporated. Due to the ability of the method to determine PPi quantitatively, it is possible to distinguish incorporation of a single base from two or several simultaneous incorporations. Since the DNA template is preferably obtained by PCR, it is relatively straight forward to increase the amount of DNA needed for such an assay.

As mentioned above our results open the possibility for a novel approach for large-scale non-electrophoretic DNA sequencing, which allows for continuous determination of the progress of the polymerization reaction with time. For the success of such an approach there is a need for high efficiency of the DNA polymerase due to the rapid increase of background signal if templates accumulate which are not "in phase".

The new approach has several advantages as compared to standard sequencing methods. Firstly, the method is suitable for handling of multiple samples in parallel. Secondly, relatively cost-effective instruments are envisioned. In addition, the method avoids the use of electrophoresis and thereby the loading of samples and casting of gels. A further advantage of the method of the present invention is that it may be used to resolve sequences which cause compressions in the gel-electrophoretic step in standard Sanger sequencing protocols.

The method of the invention may also find applicability in other methods of sequencing. For example, a number of iterative sequencing methods, advantageously permitting sequencing of double-stranded targets, based on ligation of probes or adaptors and subsequent cleavage have been described (see e.g. U.S. Pat. No. 5,599,675 and Jones, BioTechniques 22: 938–946, 1997).

Such methods generally involve ligating a double stranded probe (or adaptor) containing a Class IIS nuclease recognition site to a double stranded target (sample) DNA and cleaving the probe/adaptor-target complex at a site within the target DNA, one or more nucleotides from the ligation site, leaving a shortened target DNA. The ligation and cleavage cycle is then repeated. Sequence information is obtained by identifying one or more nucleotides at the terminus of the target DNA. The identification of the terminal nucleotide(s) may be achieved by chain extension using the method of the present invention.

Further to permit sequencing of a double stranded DNA, the method of the invention may be used in a sequencing protocol based on strand displacement, e.g. by the introduction of nicks, for example as described by Fu et al., in Nucleic Acids Research 1997, 25(3): 677–679. In such a method the sample DNA may be modified by ligating a double-stranded probe or adaptor sequence which serves to introduce a nick e.g. by containing a non- or mono-phosphorylated or dideoxy nucleotide. Use of a strand-displacing polymerase permits a sequencing reaction to take place by extending the 3' end of probe/adaptor at the nick, nucleotide incorporation being detected according to the method of the present invention.

The method of the invention may also be used for real-time detection of known single-base changes. This concept relies on the measurement of the difference in primer extension efficiency by a DNA polymerase of a matched over a mismatched 3' terminal. The rate of the DNA polymerase catalyzed primer extension is measured by detection of the detectable property associated with the tag such as fluorescence as described previously. In the single-base detection assay, single-stranded DNA fragments are used as template. Two detection primers differing with one base at the 3'-end are designed; one precisely complementary to the non-mutated DNA-sequence and the other precisely complementary to the mutated DNA sequence. The primers are hybridized with the 3'-termini over the base of interest and the primer extension rates are, after incubation with DNA polymerase and deoxynucleotides, measured by detecting the characteristics of the detectable property such as fluorescence of the tag. If the detection primer exactly matches to the template a high extension rate will be observed. In contrast, if the 3'-end of the detection primer does not exactly match to the template (mismatch) the primer extension rate will be much lower or eliminated by the use of tagged dNTPs which increase fidelity via the addition of tagged PPi. The difference in primer extension efficiency by the DNA polymerase of a matched over a mismatched 3'-terminal can then be used for single-base discrimination. Thus, the presence of the mutated DNA sequence can be distinguished over the non-mutated sequence. By performing the assay in the presence of a nucleotide degrading enzyme, it is easier to distinguish between a match and a mismatch of the type that are relatively easy to extend, such as T:G and C:T.

The invention also comprises kits for use in methods of the invention which will normally include at least the following components: (a) a test specific primer which hybridizes to sample DNA so that the target position is directly adjacent to the 3' end of the primer; (b) a polymerase; (c) an optional detection enzyme means for identifying pyrophosphate release; (d) a nucleotide-degrading enzyme; (e) deoxynucleotides, or optionally deoxynucleotide analogues having a molecular and/or atomic tag bonded to or associated with a β- and/or γ-phosphate of the dNTP, optionally including, in place of dATP, a dATP analogue which is capable of acting as a substrate for a polymerase but incapable of acting as a substrate for a said PPi-detection enzyme; and (f) optionally dideoxynucleotides, or optionally dideoxynucleotide analogues, optionally γ-tagged ddATP being replaced by a ddATP analogue which is capable of acting as a substrate for a polymerase but incapable of acting as a substrate for a said PPi-detection enzyme.

If the kit is for use with initial PCR amplification then it will also normally include at least the following components: (i) a pair of primers for PCR, at least one primer having a means permitting immobilization of said primer; (ii) a polymerase which is preferably heat stable, for example Taq DNA polymerase; (iii) buffers for the PCR reaction; and (iv) tagged deoxynucleotides and/or tagged PPi (for increased fidelity).

Single-Molecule DNA Sequencing System

Engineering a polymerase to function as a direct molecular sensor of DNA base identity during base incorporation will significantly increase the speed and utility of an enzymatic DNA sequencing system possible. At this point, direct readout from a polymerase to determine base sequence has been described in U.S. Provisional Patent Application No. 60/216,594 filed: Jul. 7, 2000. This sequencing system combines several cutting-edge technologies, including single-molecule detection, fluorescent molecule chemistry, computational biochemistry, and genetic engineering of biomolecules.

The inventors have tested whether γ-phosphate modified dATP could be incorporated by DNA polymerase. Importantly, both biological activity and, unexpectedly, increased fidelity are associated with polymerization of this γ-phosphate modified nucleotide. Since γ-phosphate modified dNTPs are not commercially available, they are designed and synthesized in Dr. Gao's lab. In the following section, the reaction route used to produce the ANS-dATP is provided. This route is also provided as an example for the synthesis of additional γ-tagged dNTPs.

Synthesis of γ-Phosphate Modified dNTPs

Yarbrough and co-workers reported the use of fluorescent nucleotides (A and U) by DNA-dependent RNA polymerase (Yarbrough et al., 1979). Following these examples, the inventors synthesized a DNA version of aminonaphthalene-1-sulfonate (ANS) γ-phosphoamide ATP. Specifically, ANS γ-phosphoamide dATP was synthesized as shown below:

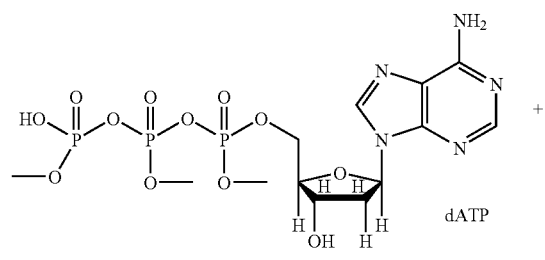

-continued

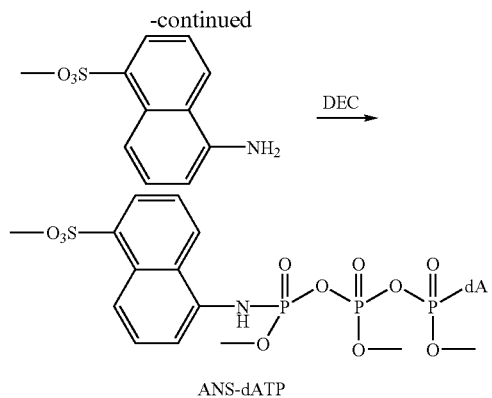

ANS-dATP

Using diode array UV detection HPLC, the fraction containing the desired product was easily identified by the distinct absorption of the ANS group at 366 nm. Additionally, $^{31}P$ NMR spectra were recorded for the γ-phosphate tagged dATP and non-modified dATP in an aqueous solution. For each compound, three characteristic resonances were observed, confirming the triphosphate moiety in the γ-tagged dATP. The combined analyses—1H NMR, HPLC and UV spectra—provide supporting evidence for the formation of the correct compound.

Although ANS was used in this example, the tag can be any tag that alters the fidelity of the polymerizing agent, exemplary examples of such tags include alkyl groups having between 1 and 30 carbon atoms, aryl groups having between about 6 and about 40 carbon atoms, or alkaryl and aralkyl groups having between about 7 and about 40 carbon atoms, or mixture or combinations thereof. The substituents can have any number of hetero atoms in the structure provided the structure represents a stable molecular system, where the hetero atoms including P, S, Si, N, O, or any other hetero atom that does not render the nucleotide toxic to the polymerase. Exemplary examples include 4-aminophenol, 6-aminonaphthol, 4-nitrophenol, 6-nitronaphthol, 4-methylphenol, 6-chloronaphthol, 4-methoxyphenol, 6-bromonaphthol, 4-chlorophenol, 6-iodonaphthol, 4-bromophenol, 4, 4'-dihydroxybiphenyl, 4-iodophenol, 8-hydroxyquinoline, 4-nitronaphthol, 3-hydroxypyridine, 4-aminonaphthol, umbelliferone, 4-methylnaphthol, resorufin, 4-methoxynaphthol, 8-hydroxypyrene, 4-chloronaphthol, 9-hydroxyanthracene, 4-bromonaphthol, 6-nitro-9-hydroxyanthracene, 4-iodonaphthol, 3-hydroxyflavone, 6-methylnaphthol, fluorescein, 6-methoxynaphthol, 3-hydroxybenzoflavone, 1-hydroxy-2-propyne, 1-hydroxy-4-pentyne, 1-hydroxy-3-butyne, 1-hydroxy-5-hexyne, Methanol, Ethanol, Propanol, Isopropanol, Butanol, Tert-butanol, Hexanol, Cyclohexanol, Heptanol, Octanol, Decanol, Undecanol, Dodecanol, 1-acetoxymethanol (CH3OOCCH2-O—NTP), 2-acetoxyethanol, 3-acetoxypropanol, 4-acetoxybutanol, 5-acetoxypentanol, 6-acetoxyhexanol, 2-nitroethanol, 3-nitropropanol, 4-nitrobutanol, 5-nitropentanol, 5-nitrohexanol, 1-hydroxy-3-propene, 1-hydroxy-2-cyclohexene, 1-hydroxy-4-butene, 1-hydroxy-3-propaldehyde, 1-hydroxy-5-pentene, 1-hydroxy-4-butanaldehyde, 1-hydroxy-6-hexene, 1-hydroxy-3-Butanone, Phenol, 4-methyl-3-hydroxypyridine, 4-Carboxyphenol, 5-methoxy-3-hydroxypyridine, 4-Acetoxymethylphenol, 5-nitro-3-hydroxypyridine, 4-nitrophenol, 5-acetoxymethyl-3-hydroxypyridine, 4-methylphenol, 6-methyl-8-hydroxyquinoline, 4-methoxyphenol 6-methoxy-8- hydroxyquinoline, 4-ethylphenol, 4-methyl-8-hydroxyquinoline, 4-butylphenol, 6-nitro-8-hydroxyquinoline, naphthol, 4-acetoxymethyl-8-hydroxyquinoline, 4 or 6 or 8 methylnaphthol pyrene, 4 or 6 or 8 methoxynaphthol, 6-methyl-8-hydroxypyrene, 4 or 6 or 8 nitronaphthol, 6-ethyl-8-hydroxypyrene, 4 or 6 or 8 ethylnaphthol, 6-nitro-8-hydroxypyrene, 4 or 6 or 8 butylnaphthol 6-(carboxysuccinimidylester) fluorescein, 4 or 6 or 8 acetoxymethylnaphthol, 6-carboxymethyl-2, 7-dichlorofluorescein, Methanol Cyclohexanol, 2-carboxy ethanol, 3-carboxypropanol, 4-carboxybutanol, 2-hydroxyethanol, 3-hydroxypropanol, 4-hydroxybutanol, 2-aminoethanol, 2-nitroethanol, 3-aminopropanol, 3-nitropropanol, 4-aminobutanol, 4-nitrobutanol, or any other similar substituent. Exemplary modified nucleotide include ANS modified nucleotide and Adenosine-5'-(γ-4-nitrophenyl)triphosphate, Adenosine-5'-(γ-4-iodonaphthyl), Guanosine-5'-(γ-4-nitrophenyl)triphosphate, triphosphate Adenosine-5'-(γ-6-methylnaphthyl) triphosphate, Cytosine-5'-(γ-4-nitrophenyl) triphosphate, Thymidine-5'-(γ-4-nitrophenyl) triphosphate, Adenosine-5'-(γ-6-methoxynaphthyl)triphosphate, Uracil-5'-(γ-4-nitrophenyl) triphosphate, 3'-azido-3'-deoxythymidine-5'-(γ-4-nitrophenyl)triphosphate, Adenosine-5'-(γ-6-aminonaphthyl)triphosphate, 3'-azido-2', 3'-dideoxythymidine-5'-(γ-4-nitrophenyl)triphosphate, Adenosine-5'-(γ-6-nitronaphthyl)triphosphate, 2', 3'-didehydro-2', 3'-dideoxythymidine-5'-(γ-4-nitrophenyl)triphosphate, Adenosine-5'-(γ-6-chloronaphthyl)triphosphate, Adenosine-5'-(γ-4-aminophenyl)triphosphate, Adenosine-5'-(γ-6-bromonaphthyl)triphosphate, Adenosine-5'-(γ-4-methylphenyl)triphosphate, Adenosine-5'-(γ-6-iodonaphthyl) triphosphate, Adenosine-5'-(γ-4-methoxyphenyl) triphosphate, Adenosine-5'-(γ-4'-hydroxybiphenyl) triphosphate, Adenosine-5'-(γ-4-chlorophenyl)triphosphate, Adenosine-5'-(γ-8-quinolyl)triphosphate, Adenosine-5'-(γ-4-bromophenyl)triphosphate, Adenosine-5'-(γ-3-pyridyl) triphosphate, Adenosine-5'-(γ-umbelliferone), Adenosine-5'-(γ-4-iodophenyl)triphosphate, Adenosine-5'-(γ-4-nitronaphthyl)triphosphate, Adenosine-5'-(γ-resorufin) triphosphate, Adenosine-5'-(γ-pyrene)triphosphate, Adenosine-5'-(γ-4-aminonaphthyl)triphosphate, Adenosine-5'-(γ-anthracene)triphosphate, Adenosine-5'-(Γ-6-nitroanthracene)triphosphate, Adenosine-5'-(γ-4-methylnaphthyl) triphosphate, Adenosine-5'-(γ-flavonyl)triphosphate, Adenosine-5'-(γ-4-methoxynaphthyl)triphosphate, Adenosine-5'-(γ-fluorescein)triphosphate, Adenosine-5'-(γ-benzoflavone)triphosphate, Adenosine-5'-(γ-4-chloronaphthyl) triphosphate, Adenosine-5'-(γ-(4-nitrophenyl)-γ'-(4-aminophenyl)triphosphate, Adenosine-5'-(γ-4-bromonaphthyl)triphosphate, Adenosine-5'-(γ-(4-nitrophenyl)-γ'-(4-nitronaphthyl)triphosphate, Adenosine-5'-(γ-methyl)triphosphate, Adenosine-5'-(γ-acetoxypropyl) triphosphate, Guanosine-5'-(γ-methyl)triphosphate, Cytosine-5'-(γ-methyl)triphosphate, Adenosine-5'-(γ-acetoxymethyl)triphosphate (CH3OCCH,—O—NTP), Thymidine-5'-(γ-methyl)triphosphate, Uracil-5'-(γ-methyl)triphosphate, Adenosine-5'-(γ-acetoxyethyl)triphosphate, 3'-azido-3'-deoxythymidine-5-(γ-methyl)triphosphate, Adenosine-5'-(γ-acetoxybutyl)triphosphate, 3'-azido-2', 3'-dideoxythymidine-5'-(γ-methyl)triphosphate, Adenosine-5'-(γ, acetoxypentyl)triphosphate,2', 3'-didehydro-2', 3'-dideoxythymidine-5'-(γ-methyl)triphosphate, Adenosine-5'-(γ-acetoxyhexyl)triphosphate, Adenosine-5'-(γ-ethyl) triphosphate, Adenosine-5'-(γ-2-nitroethyl)triphosphate, Adenosine-5'-(γ-propyl)triphosphate, Adenosine-5'-(γ-4-butyl)triphosphate, Adenosine-5'-(γ-3-nitropropyl)triphosphate, Adenosine-5'-(γ-hexyl)triphosphate, Adenosine-5'-(γ-octyl)triphosphate, Adenosine-5'-(γ-4-nitrobutyl) triphosphate, Adenosine-5'-(γ-decyl)triphosphate, Adenosine-5'-(γ-dodecyl)triphosphate, Adenosine-5'-(γ-5-nitropentyl)triphosphate, Adenosine-5'-(γ-isopropyl)triphosphate, Adenosine-5'-(γ-tert-butyl)triphosphate, Adenosine-5'-(γ-methyl)-(γ'-ethyl)triphosphate, Adenosine-5'-(γ-cyclohexyl)triphosphate, Adenosine-5'-(γ-methyl)-(γ'-propyl)triphosphate, Adenosine-5'-(γ-2-propenyl) triphosphate, Adenosine-5'-(γ-3-butenyl)triphosphate, Guanosine-5'-(γ-2-propenyl)triphosphate, Adenosine-5'-(γ-4-pentenyl)triphosphate, Cytosine-5'-(γ-2-propenyl)triphosphate, Adenosine-5'-(γ-5-hexenyl)triphosphate, Thymidine-5'-(γ-2-propenyl)triphosphate, Adenosine-5'-(γ-cyclohexenyl)triphosphate, Uracil-5'-(7–2-propenyl) triphosphate, Adenosine-5'-(γ-3-propanaldehyde) triphosphate, 3'-azido-3'-deoxythymidine-5'-(γ-2-propenyl) triphosphate, Adenosine-5'-(γ-4-butanaldehyde) triphosphate, 3'-azido-2',3'-dideoxythymidine-5'-(γ-2-propenyl)triphosphate Adenosine-5'-(γ-3-butanone) triphosphate, 2', 3'-didehydro-2',3'-dideoxythymidine-5'-(γ-2-propenyl)triphosphate, Adenosine-5'-(γ-2-propynyl) triphosphate, 3'-azido-2',3'-dideoxythymidine-5'-(γ-2-propynyl)triphosphate, Guanosine-5'-(γ-2-propynyl) triphosphate, Cytosine-5'-(γ-2-propynyl)triphosphate, 2', 3'-didehydro-2', 3'-dideoxythymidine-5'-(γ-2-propynyl) triphosphate Thymidine 5'-(γ-2-propynyl)triphosphate, Uracil-5'-(γ-2-propynyl)triphosphate, Adenosine-5'-(γ-3-butynyl)triphosphate, 3'-azido-3'-deoxythymidine-5'-(γ-2-propynyl)triphosphate, Adenosine-5'-(γ-4-pentynyl)triphosphate, Adenosine-5'-(γ-5-pentynyl)triphosphate, Adenosine-5'-(γ-4-phenyl)triphosphate, Adenosine-5'-(γ-(4 or 6 or 8 acetoxymethyl naphthyl)triphosphate, Guanosine-5'-(γ-4-phenyl)triphosphate, Cytosine-5'-(γ-4-phenyl)triphosphate, Adenosine-5'-(γ-(4-methylpyridyl)triphosphate, Thymidine-5'-(γ-4-phenyl)triphosphate, Uracil-5'-(γ-4-phenyl)triphosphate, Adenosine-5'-(γ-(5-methoxypyridyl)triphosphate, 3'-azido-3'-deoxythymidine-5'-(γ-4-phenyl)triphosphate, Adenosine-5'-(γ-(5-nitropyridyl)triphosphate, 3'-azido-2',3'-dideoxythymidine-5'-(γ-4-phenyl)triphosphate, Adenosine-5'-(γ-(5-acetoxymethylpyridyl)triphosphate, 2', 3'-didehydro-2', 3'-dideoxythymidine-5'-(γ-4-phenyl)triphosphate, Adenosine-5'-(γ-(6-methyl-1-quinolyl)triphosphate, Adenosine-5'-(γ-4-carboxyphenyl)triphosphate, Adenosine-5'-(γ-(6-methoxy-1-quinolyl)triphosphate, Adenosine-5'-(γ-(4-acetoxymethyl) phenyl)triphosphate, Adenosine-5'-(γ-(4-methyl-1-quinolyl)triphosphate, Adenosine-5'-(γ-4-nitrophenyl)triphosphate, Adenosine-5'-(γ-4-methylphenyl) triphosphate, Adenosine-5'-(γ-(6-nitro-1-quinolyl) triphosphate, Adenosine-5'-(γ-4-methoxyphenyl) triphosphate, Adenosine-5'-(γ-(4-acetoxymethylpyrenyl) triphosphate, Adenosine-5'-(γ-4-ethylphenyl)triphosphate, Adenosine-5'-(γ-(6-methylpyrenyl)triphosphate, Adenosine-5'-(γ-4-butylphenyl)triphosphate, Adenosine 5'-(γ-naphthyl) triphosphate, Adenosine-5'-(γ-(6-ethylpyrenyl)triphosphate, Adenosine-5'-(γ-(4 or 6 or 8 methyl naphthyl)triphosphate, Adenosine-5'-(γ-(6-nitropyrenyl)triphosphate, Adenosine-5'-(γ-(4 or 6 or 8 methoxynaphthyl)triphosphate, Adenosine-5'-(γ-6-(carboxysuccinimidyl fluorescein)triphosphate, Adenosine-5'-(γ-(4 or 6 or 8 nitro naphthyl)triphosphate. Adenosine-5'-(γ-6-carboxymethyl-2, 7-dichlorofluorescein) triphosphate, Adenosine-5'-(γ-(4 or 6 or 8 ethyl naphthyl) triphosphate, Adenosine-5'-(γ-4-phenyl)-(γ'-4 nitrophenyl)-triphosphate, Adenosine-5'-(γ-(4 or 6 or 8 butyl naphthyl) triphosphate, Adenosine-5'-(γ-4-phenyl)-(γ'-4 aminophenyl) triphosphate, Adenosine-5'-(γ-methyl)triphosphate, Adenosine-5'-(γ-3-aminopropyl)triphosphate, Guanosine-5'-(γ-methyl)triphosphate, Adenosine-5'-(γ-4-aminobutyl)

triphosphate, Cytosine-5'-(γ-methyl)triphosphate Adenosine-5'-(γ-cyclohexyl)triphosphate, Thymidine-5'-(γ-methyl)triphosphate Adenosine-5'-(γ-2-carboxyethyl)triphosphate, Uracil-5'-(γ-methyl)triphosphate, Adenosine-5'-(γ-3-carboxypropyl)triphosphate, 3'-azido-3'-deoxythymidine-5'-(7-methyl)triphosphate, Adenosine-5'-(γ-4-carboxybutyl)triphosphate, 3'-azido-2',3'-dideoxythymidine-5'-(γ-methyl)triphosphate, Adenosine-5'-(γ-2-hydroxyethyl)triphosphate, 2', 3'-didehydro-2', 3'-dideoxythymidine-5'-(γ-methyl)triphosphate, Adenosine-5'-(γ-3-hydroxypropyl)triphosphate, Adenosine-5'-(γ-ethyl)triphosphate, Adenosine-5'-(γ-propyl)triphosphate, Adenosine-5'-(γ-4-hydroxybutyl)triphosphate, Adenosine-5'-(γ-4-butyl)triphosphate, Adenosine-5'-(γ-2-nitroethyl)triphosphate, Adenosine-5'-(γ-hexyl)triphosphate, Adenosine-5'-(γ-3-nitropropyl)triphosphate, Adenosine-5'-(γ-isopropyl)triphosphate, Adenosine-5'-(γ-4-nitrobutyl)triphosphate, Adenosine-5'-(γ-tert-butyl)triphosphate, Adenosine-5'-(γ-methyl)-(γ'-ethyl)triphosphate, Adenosine-5'-(γ-cyclohexyl)triphosphate, Adenosine-5'-(γ-2-aminoethyl)triphosphate, Adenosine-5'-(γ-methyl)-(γ'-propyl)triphosphate, or any other similar substituted nucleotide.

Polymerase Activity Assays Using Tagged dNTP(s)

The ability of a commercially available polymerase to incorporate the novel dNTPs synthesized was monitored using primer extension assays.

TABLE 1

Primer Strand Definitions Used in Examples

Primer Strand:

| | |
|---|---|
| TOP 5' | GGT ACT AAG CGG CCG CAT G 3' |

Template Strands:

| | |
|---|---|
| BOT-T 3' | CCA TGA TTC GCC GGC GTA CT 5' |
| BOT-C 3' | CCA TGA TTC GCC GGC GTA CC 5' |
| BOT-G 3' | CCA TGA TTC GCC GGC GTA CG 5' |
| BOT-A 3' | CCA TGA TTC GCC GGC GTA CA 5' |
| BOT-Sau 3' | CCA TGA TTC GCC GGC GTA CCT AG 5' |
| BOT-TC 3' | CCA TGA TTC GCC GGC GTA CTC 5' |
| BOT-3TC 3' | CCA TGA TTC GCC GGC GTA CTT TC 5' |

'TOP' represents the primer strand of the DNA duplex molecules used in the primer extension assays. Variants of the template strand are represented by 'BOT'. The relevant feature of the DNA template is indicated after the hyphen. For example, BOT-T, BOT-C, BOT-G, BOT-A are used to monitor polymerase incorporation efficiency and fidelity for either nucleotides or nucleotide variants of dATP, dGTP, dCTP, and dTTP, respectively.

γ-Phosphate-Tagged dNTP Incorporation By Taq Polymerase

The following example illustrates that commercially available Taq DNA polymerase efficiently incorporates the ANS-γ-phosphate dNTPs, the syntheses and characterization of which are described above.

This first example illustrates the incorporation of ANS-γ-phosphate dATP to produce extended DNA products from primer/template duplexes. The reactions were carried out in extension buffer and the resulting radiolabeled products were size separated on a 20% denaturing polyacrylamide gel. Data were collected using a phosphorimaging system. Referring now FIG. 1, Lane 1 contained 5' radiolabeled 'TOP' probe in extension buffer. Lane 2 contained Taq DNA polymerase, 50 μM dGTP incubated with a DNA duplex (radiolabeled TOP with excess 'BOT-Sau'). Lane 3 contained Taq DNA polymerase, 50 μM dATP incubated with a DNA duplex (radiolabeled TOP with excess 'BOT-Sau'). Lane 4 contained Taq DNA polymerase, 50 μM ANS-γ-dATP incubated with a DNA duplex (radiolabeled TOP with excess 'BOT-Sau'). Lane 5 contained Taq DNA polymerase, 50 μM dGTP incubated with a DNA duplex (radiolabeled TOP with excess 'BOT-TC'). Lane 6 contained spill-over from lane 5. Lane 7 contained Taq DNA polymerase, 50 μM dATP incubated with a DNA duplex (radiolabeled TOP with excess 'BOT-TC'). Lane 8 contained Taq DNA polymerase, 50 μM ANS-γ-dATP incubated with a DNA duplex (radiolabeled TOP with excess 'BOT-TC'). Lane 9 contained Taq DNA polymerase, 50 μM dGTP incubated with a DNA duplex (radiolabeled TOP with excess 'BOT-3TC'). Lane 10 contained Taq DNA polymerase, 50 μM dATP incubated with a DNA duplex (radiolabeled TOP with excess 'BOT-3TC'). Lane 11 contained Taq DNA polymerase, ANS-γ-dATP incubated with a DNA duplex (radiolabeled TOP with excess 'BOT-3TC'). Lane 12 contained 5' radiolabeled 'TOP' probe in extension buffer. Lane 13 contained 5' radiolabeled 'TOP' probe and Taq DNA polymerase in extension buffer. Oligonucleotide sequences are shown in Table 1.

Quantitative comparison of lane 1 with lane 4 demonstrates that very little non-specific, single-base extension was detected when ANS-γ-dATP was included in the reaction, and the first incorporated base should be dGTP (which was not added to the reaction). Quantitative analysis of lanes 1 and 8 demonstrates that approximately 71% of the TOP primer are extended by a template-directed single base when ANS-γ-dATP was included in the reaction and the first incorporated base should be dATP. Thus, Taq DNA polymerase incorporates γ-tagged nucleotides. Equally important to the polymerase's ability to incorporate a γ-tagged nucleotide is its ability to extend the DNA polymer after the modified dATP was incorporated. Comparison of lane 1 with lane 11 demonstrated that a DNA strand was extended after a γ-tagged nucleotide was incorporated. Thus, incorporation of a modified nucleotide was not detrimental to polymerase activity. Note, too, that extension of the primer strand by incorporation of an ANS-γ-nucleotide depended upon Watson-Crick base-pairing rules. In fact, the fidelity of nucleotide incorporation was increased at least 15-fold by the addition of this tag to the γ-phosphate.

Analyzing the data from FIG. 1, the percentages for correct versus incorrect extension can be determined. Table II tabulates these result.

TABLE II

Percent of Correct Extension versus Percent Incorrect Extension

| Lane | Descriptor | Expected Result | Percent Correct | Percent Mis-Extended | Total Percent Extended |
|---|---|---|---|---|---|
| 1 | Background | No Extension | 89.91 | 10.09 | 10.9 |
| 2 | dGTP | 1 base Extension | 52.99 | 19.97 | 72.97 |
| 3 | dATP | No Extension | 61.99 | 38.01 | 38.01 |
| 4 | g-dATP | No Extension | 87.43 | 12.57 | 12.57 |
| 5 | dGTP | No Extension | 24.99 | 75.01 | 75.01 |
| 6 | Spill | | | | |
| 7 | dATP | 1 base Extension | 15.24 | 69.01 | 84.25 |
| 8 | g-dATP | 1 base Extension | 71.14 | 6.51 | 77.64 |

TABLE II-continued

Percent of Correct Extension versus Percent Incorrect Extension

| Lane | Descriptor | Expected Result | Percent Correct | Percent Mis-Extended | Total Percent Extended |
|---|---|---|---|---|---|
| 9 | dGTP | No Extension | 32.20 | 67.80 | 67.80 |
| 10 | dATP | 3 base Extension | 27.11 | 54.92 | 82.03 |
| 11 | g-dATP | 3 base Extension | 73.43 | 3.87 | 77.31 |
| 12 | Background | No Extension | 95.19 | 4.81 | 4.81 |
| 13 | Background | No Extension | 95.92 | 4.08 | 4.08 |

From the data, the relative percent fidelity improvement can be determined of dATP and ANS-γ-phosphate tagged dATP. When G is to be incorporated and dATP is the only nucleotide in the reaction medium, then the tagged nucleotide provides about a 3 fold decrease in misextensions. When a single A is to be incorporated and dATP is only nucleotide in the reaction medium, then the tagged nucleotide provides about an 11 fold decrease in misextensions. When three A's are to be incorporated and dATP is only nucleotide in the reaction medium, then the tagged nucleotide provides about a 14 fold decrease in misextensions.

Figure 2:
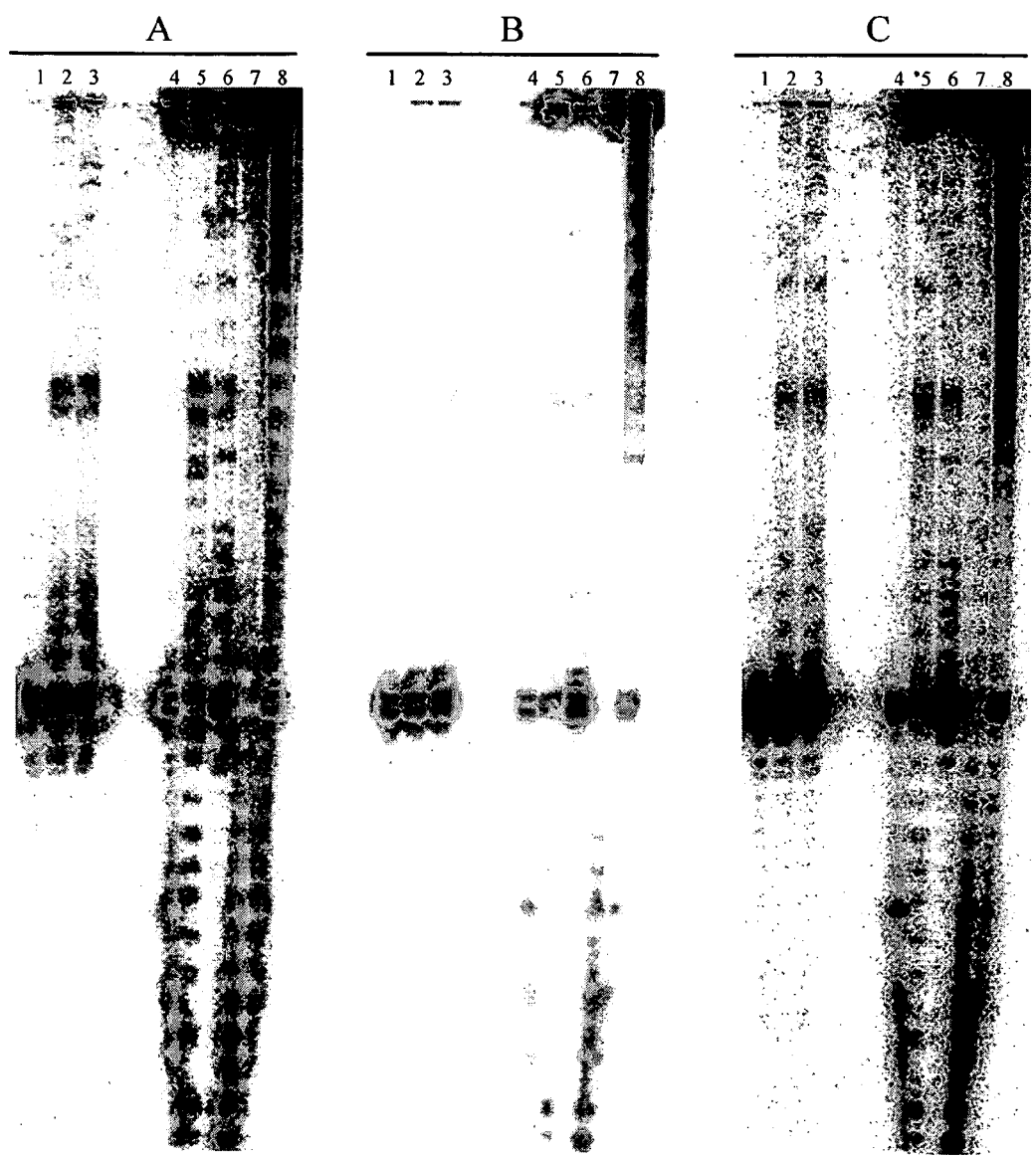
FIG. 2 depicts the synthesis of extended DNA polymers using all four ANS-γ-phosphated tagged dNTPs and the Taq polymerase.

This next example illustrates the synthesis of extended DNA polymers using all four ANS tagged γ-phosphate dNTPs. Products generated in these reactions were separated on a 20% denaturing polyacrylamide gel, the gel was dried and imaged following overnight exposure to a Fuji BAS1000 imaging plate. Referring now to FIG. 2, an image of (A) the actual gel image, (B) a lightened phosphorimage and (C) an enhanced phosphorimage. Lane descriptions for A, B, and C follow: Lane 1 is the control containing purified 10-base primer extended to 11 and 12 bases by template-mediated addition of α-$^{32}$P dCTP. Lane 2 includes the same primer that was incubated with double-stranded plasmid DNA at 96° C. for 3 minutes (to denature template). The reaction was brought to 37° C. (to anneal the primer to the template), Taq DNA polymerase and all four natural dNTPs (100 μM, each) were added and the reaction was incubated at 37° C. for 60 minutes. Lane 3 includes the same labeled primer that was incubated with double-stranded DNA plasmid at 96° C. for 3 minutes; Taq DNA Polymerase and all four γ-modified dNTPs (100 M, each) were added and the reaction was incubated at 37° C. for 60 minutes. Lane 4 includes the control, purified 10-base primer that was extended to 11 and 12 bases by the addition of α-$^{32}$P dCTP and was cycled in parallel with the reactions in lanes 5–8. Lane 5 includes the same $^{32}$P-labeled primer that was incubated with double-stranded plasmid DNA at 96° C. for 3 minutes, the reaction was brought to 37° C. for 10 minutes, during which time Taq DNA polymerase and all four natural dNTPs (100 μM, each) were added. The reaction was cycled 25 times at 96° C. for 10 seconds, 37° C. for 1 minute, and 70° C. for 5 minutes Lane 6 includes the same $^{32}$P-labeled primer that was incubated with double-stranded plasmid DNA at 96° C. for 3 minutes, the reaction was brought to 37° C. for 10 minutes, during which time Taq DNA polymerase and all four γ-modified dNTPs (100 μM, each) were added. The reaction was cycled 25 times at 96° C. for 10 seconds, 37° C. for 1 minute, and 70° C. for 5 minutes. Lane 7 includes nonpurified, 10-base, γ$^{32}$P-labeled primer that was incubated with double-stranded DNA plasmid at 96° C. for 3 minutes, the reaction was brought to 37° C. for 10 minutes, during which time Taq DNA polymerase and all four natural dNTPs (100 μM, each) were added. The reaction was cycled 25 times at 96° C. for 10 seconds, 37° C. for 1 minute, and 70° C. for 5 minutes. Lane 8 includes nonpurified, 10-base, γ$^{32}$P-labeled primer that was incubated with double-stranded DNA plasmid at 96° C. for 3 minutes, the reaction was brought to 37° C. for 10 minutes, during which time Taq DNA polymerase and all four γ-modified dNTPs (100 μM, each) were added. The reaction was cycled 25 times at 96° C. for 10 seconds, 37° C. for 1 minute, and 70° C. for 5 minutes. Evident in the reactions involving tagged dNTPs is a substantial decrease in pyrophosphorolysis as compared to reactions involving natural nucleotides.

Figure 3:
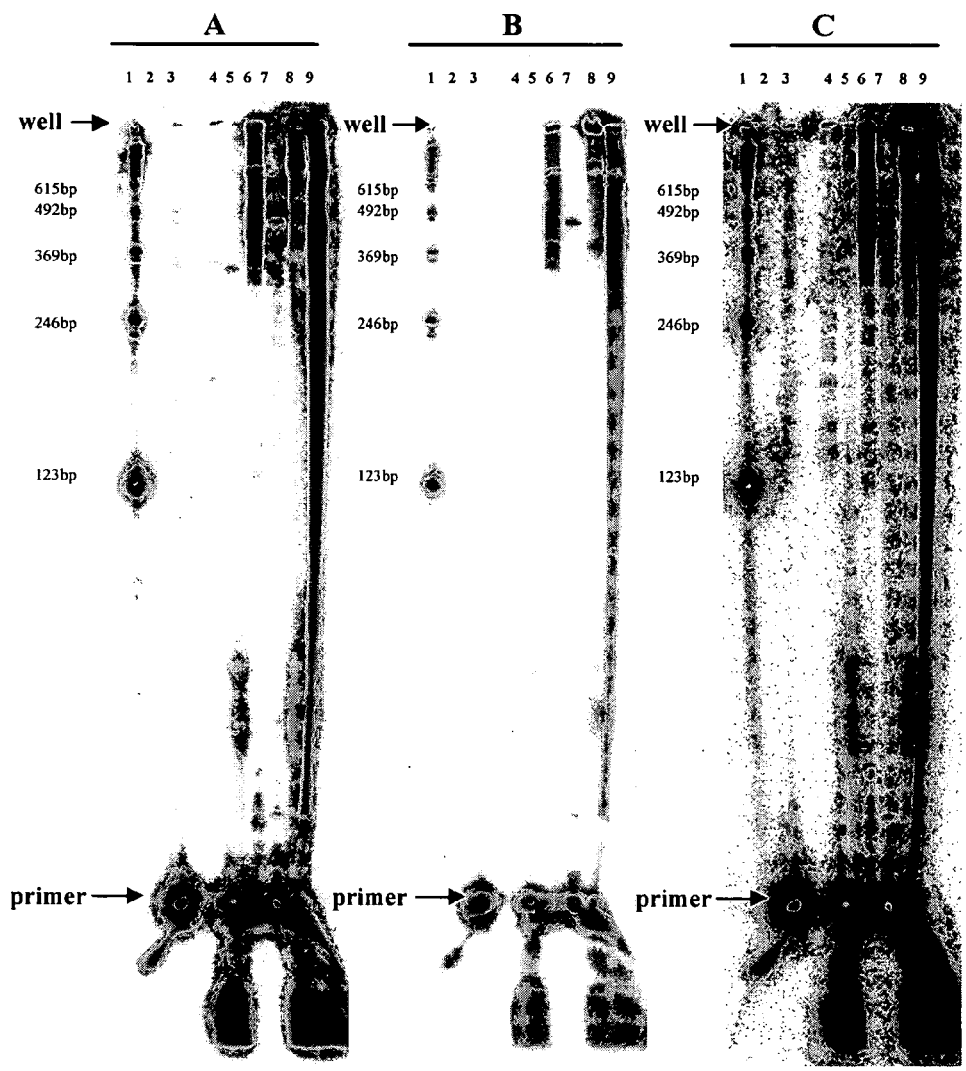
FIG. 3 depicts the synthesis of long DNA polymers using all four ANS-γ-phosphated tagged dNTPs and the Taq polymerase.

This next example illustrates the synthesis of long DNA polymers using all four ANS tagged γ-phosphate dNTPs. Each primer extension reaction was split into two fractions, and one fraction was electrophoresed through a 20% denaturing gel (as described above), while the other was electrophoresed through a 6% denaturing gel to better estimate product lengths. The gel was dried and imaged (overnight) to a Fuji BAS1000 imaging plate. Referring now to FIG. 3, an image of (A) the actual gel, (B) a lightened phosphorimage of the actual gel, and (C) an enhanced phosphorimage of the actual gel. Lane descriptions for A, B, and C follow: Lane 1 includes 123 Marker with size standards indicated at the left of each panel. Lane 2 contained the control, purified 10-base primer extended to 11 and 12 bases by template-mediated addition of α-$^{32}$P dCTP. Lane 3 contained the same $^{32}$P-labeled primer that was incubated with double-stranded plasmid DNA at 96° C. for 3 minutes (to denature template), the reaction was brought to 37° C. (to anneal the primer to the template), Taq DNA polymerase and all four natural dNTPs (100 μM, each) were added and the reaction was incubated at 37° C. for 60 minutes. Lane 4 includes the same $^{32}$P-labeled primer that was incubated with double-stranded DNA plasmid at 96° C. for 3 minutes, the reaction was brought to 37° C., Taq DNA polymerase and all four γ-modified dNTPs (100 μM, each) were added and the reaction was incubated at 37° C. for 60 minutes. Lane 5 includes the control, purified 10-base primer that was extended to 11 and 12 bases by the addition of α-$^{32}$P-dCTP was cycled in parallel with the reactions in lanes 5–8. Lane 6 includes the same $^{32}$P-labeled primer that was incubated with double-stranded plasmid DNA at 96° C. for 3 minutes, the reaction was brought to 37° C. for 10 minutes, during which time Taq DNA polymerase and all four natural dNTPs (100 μM, each) were added. The reaction was cycled 25 times at 96° C. for 10 seconds, 37° C. for 1 minute, and 70° C. for 5 minutes. Lane 7 includes the same $^{32}$P-labeled primer that was incubated with double-stranded plasmid DNA at 96° C. for 3 minutes, the reaction was brought to 37° C. for 10 minutes, during which time Taq DNA polymerase and all four γ-modified dNTPs (100 μM, each) were added. The reaction was cycled 25 times at 96° C. for 10 seconds, 37° C. for 1 minute, and 70° C. for 5 minutes. Lane 8 includes nonpurified, 10-base, γ$^{32}$P-labeled primer that was incubated with double-stranded DNA plasmid at 96° C. for 3 minutes, the reaction was brought to 37° C. for 10 minutes, during which time Taq DNA polymerase and all four natural dNTPs (100 μM, each) were added. The reaction was cycled 25 times at 96° C. for 10 seconds, 37° C. for 1 minute, and 70° C. for 5 minutes. Lane 9 includes nonpurified, 10-base, γ-$^{32}$P-labeled primer that was incubated with double-stranded DNA plasmid at 96° C. for 3 minutes, the reaction was brought to 37° C. for 10 minutes, during which time Taq DNA polymerase and all four γ-modified dNTPs (100 μM, each) were added. The reaction was cycled 25 times at 96° C. for 10 seconds, 37° C. for 1 minute, and 70° C. for 5 minutes.

The majority of extension products in this reaction are several hundred bases long for both natural and γ-modified dNTPs, and a significant percentage of these products are too large to enter the gel. Thus, demonstrating that the γ-phosphate tagged dNTPs are used by Taq polymerase to generate long DNA polymers that are non-tagged or native DNA polymer chains.

Different Polymerases React Differently to the Modified Nucleotides

The indicated enzymes (Taq DNA Polymerase, DNA polymerase I—Klenow Fragment, Pfu DNA Polymerase, HIV-1 Reverse Transcriptase, T7 DNA Polymerase Sequenase Version 2) were incubated in the manufacturers suggested reaction buffer, 50 M of the indicated nucleotide were added and the reactions, containing aDNA duplex (5' radiolabeled TOP and the specified template) were incubated at 37° C. for 30–60 minutes. The reaction products were analyzed by size separation through a 20% denaturing gel.

Taq DNA polymerase efficiently uses the modified nucleotides to synthesize extended DNA polymers at increased accuracy as shown in FIGS. 1–6.

Figure 4:
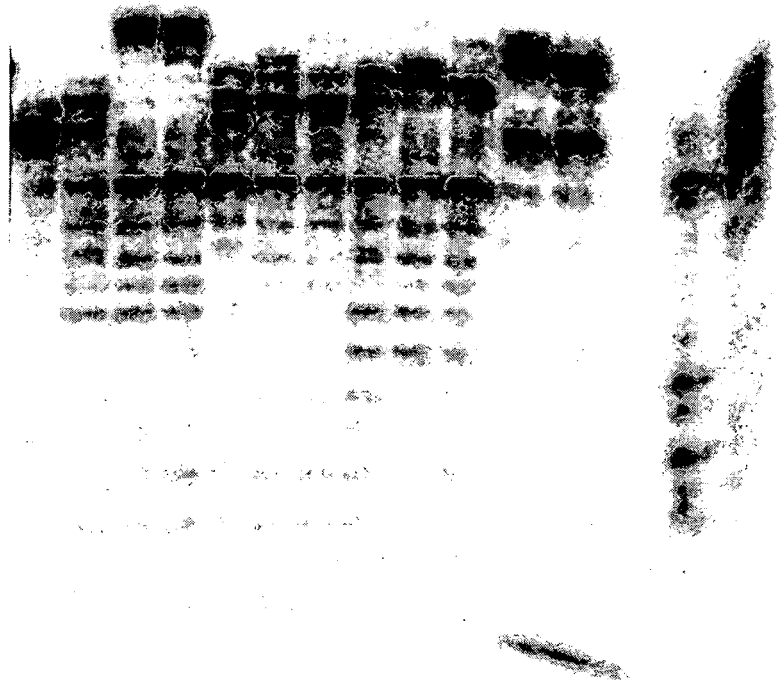
FIG. 4 depicts the use of γ-modified nucleotides with the Klenow fragment from E. coli DNA polymerase to form DNA polymer.

The Klenow fragment from *E. coli* DNA polymerase I efficiently uses γ-modified nucleotides, but does not exhibit the extreme fidelity improvements observed with other enzymes as shown in FIG. 4.

Pfu DNA polymerase does not efficiently use γ-modified nucleotides and is, thus, not a preferred enzyme for the single-molecule sequencing system as shown in FIG. 5.

Figure 6:
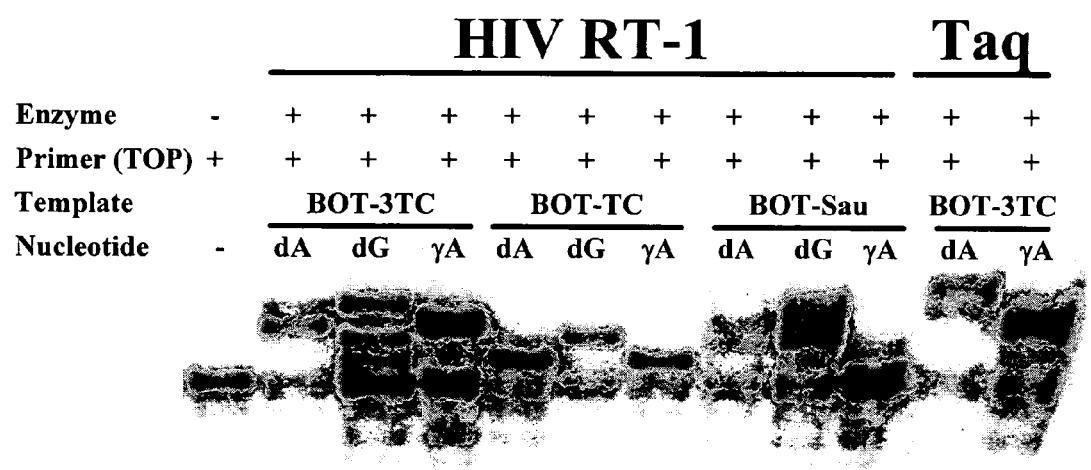
FIG. 6 depicts the use of γ-modified nucleotides using HIV-1 reverse transcriptase to efficiently form DNA polymers.

HIV-1 reverse transcriptase efficiently uses the γ-modified nucleotides, and significant fidelity improvement results as shown in FIG. 6.

Figure 7:
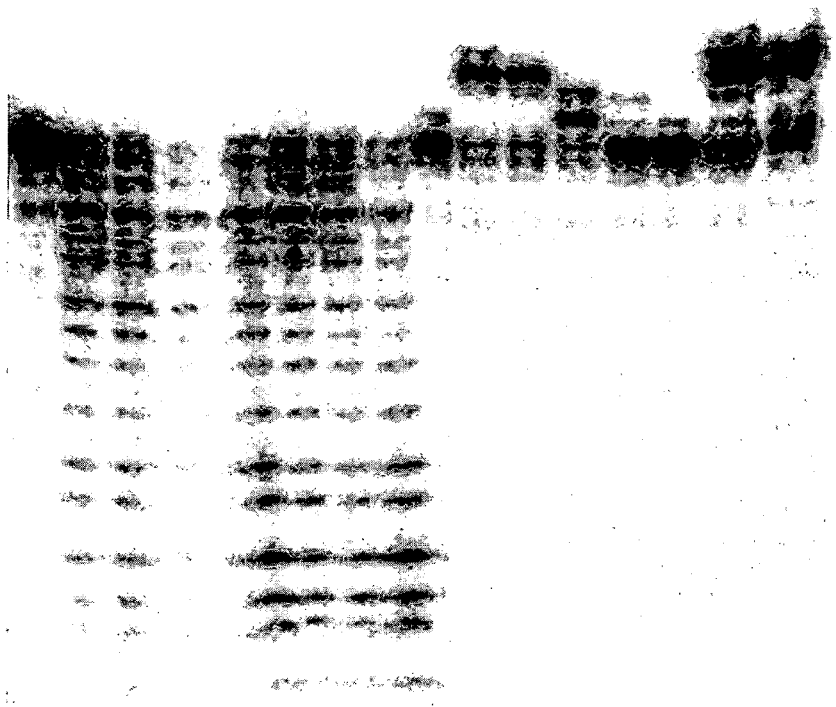
FIG. 7 depicts the experimental results for native T7 DNA polymerase and Sequenase.

Polymerization activity is difficult to detect in the reaction products generated by native T7 DNA polymerase (due to the presence of the enzyme's exonuclease activity). However, its genetically modified derivative, Sequenase, shows that the γ-modified nucleotides are efficiently incorporated, and that incorporation fidelity is improved, relative to non-modified nucleotides. The experimental results for native T7 DNA polymerase and Sequenase are shown in FIG. 7.

Thus, for Taq polymerase or HIV-1 reverse transcriptase, improved fidelity, due to the use of the γ-modified dNTPs of this invention, enables single-molecule DNA sequencing. However, not all polymerases equally utilize the γ-modified nucleotides of this invention, specifically, Klenow, Sequenase, HIV-1 reverse transcriptase and Taq polymerases incorporate the modified nucleotides of this invention, while the Pfu DNA polymerase does not appear to incorporate (or incorporates very inefficiently) the modified nucleotides of this invention.

Elevated Temperature Affects the Stability of ANS-γ-Phosphate-tagged dNTPs

This experiment illustrates the effect of elevated temperature on ANS-tagged dNTPs. Specifically, γ-tagged dNTPs were heated for 7 minutes at 96° C. Primer extension reactions containing heat-treated or untreated natural or ANS-tagged dNTPs were compared to determine the effect of high temperature. The reactions were carried out in extension buffer and the resulting radiolabeled products were size separated on a 20% denaturing polyacrylamide gel. Data were collected using a phosphorimaging system.

Figure 8:
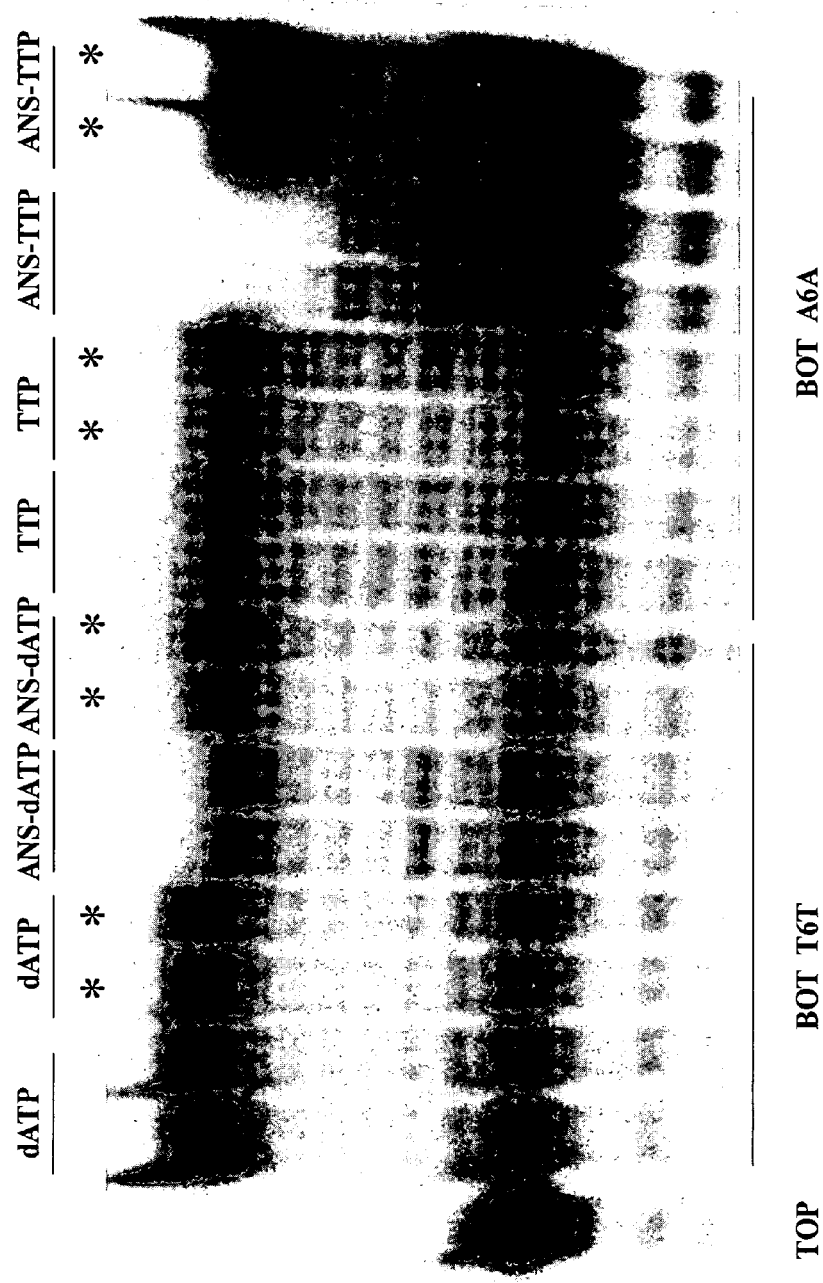
FIG. 8 depicts the effect of elevated temperature on ANS-tagged dATPs and ANS-tagged dATPs.

Referring to FIG. 8. Lane 1 contained free γ-$^{32}$P-labeled primer ('TOP'). Lanes 2–9 are extension reactions containing the γ-$^{32}$P-labeled TOP that was annealed to a single-stranded template ('BOT T6T') at 96° C. for 3 minutes (to form primer-template duplex). Taq DNA polymerase and the specified dNTPs (10 μM) were added and the reactions were carried out at 37° C. for 30 minutes. Each lane contained as follows: untreated natural dATP (Lanes 2–3), heat-treated natural dATP (Lanes 4–5), untreated ANS-γ-tagged dATP (Lanes 6–7), heat-treated ANS-γ-tagged dATP (Lanes 8–9). Lanes 10–17 are extension reactions containing the γ-$^{32}$P-labeled TOP that was annealed to a single-stranded template ('BOT A6A') at 96° C. for 3 minutes (to form primer-template duplex). Taq DNA polymerase and the specified dNTPs (10 μM) were added and the reactions were carried out at 37° C. for 30 minutes. Each lane contained as follows: untreated natural TTP (Lanes 10–11), heat-treated natural TTP (Lanes 12–13), untreated ANS-γ-tagged TTP (Lanes 14–15), heat-treated ANS-γ-tagged TTP (Lanes 16–17).

Figure 9:
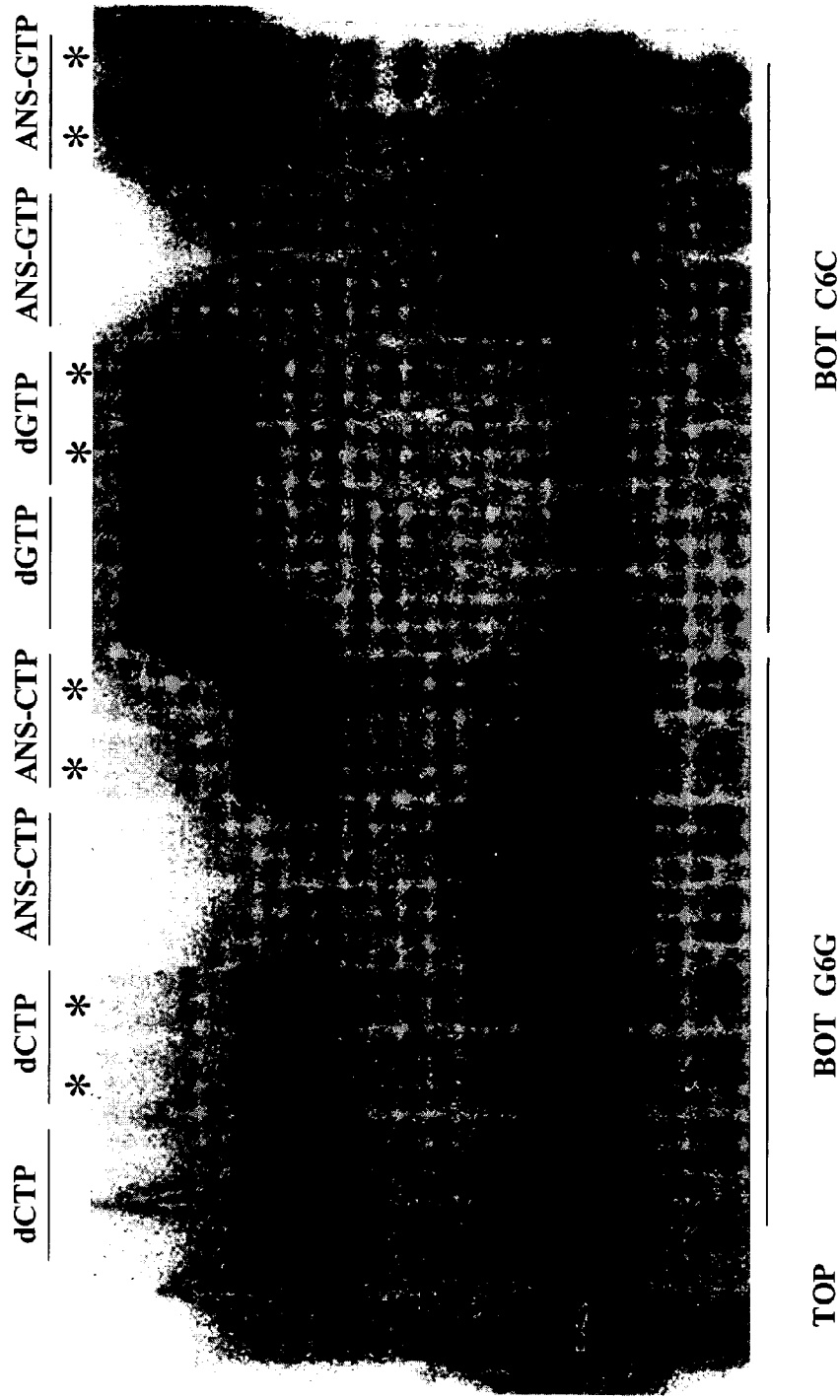
FIG. 9 depicts the effect of elevated temperature on ANS-tagged dCTPs and ANS-tagged dGTPs.

Referring to FIG. 9. Lane 1 contained free γ-$^{32}$P-labeled primer ('TOP'). Lanes 2–9 are extension reactions containing the γ-$^{32}$P-labeled TOP that was annealed to a single-stranded template ('BOT G6G') at 96° C. for 3 minutes (to form primer-template duplex). Taq DNA polymerase and the specified dNTPs (10 μM) were added and the reactions were carried out at 37° C. for 30 minutes. Each lane contained as follows: untreated natural dCTP (Lanes 2–3), heat-treated natural dCTP (Lanes 4–5), untreated ANS-γ-tagged dCTP (Lanes 6–7), heat-treated ANS-γ-tagged dCTP (Lanes 8–9). Lanes 10–17 are extension reactions containing the γ-$^{32}$P-labeled TOP that was annealed to a single-stranded template ('BOT C6C') at 96° C. for 3 minutes (to form primer-template duplex). Taq DNA polymerase and the specified dNTPs (10 μM) were added and the reactions were carried out at 37° C. for 30 minutes. Each lane contained as follows: untreated natural dGTP (Lanes 10–11), heat-treated natural dGTP (Lanes 12–13), untreated ANS-γ-tagged dGTP (Lanes 14–15), heat-treated ANS-γ-tagged dGTP (Lanes 16–17).

Comparison between the lanes containing untreated and heat-treated natural dNTPs does not show significant, if any, change in terms of extension patterns and amount of completely extended products. In contrast, after heat-treatment the ANS-γ-tagged dNTPs behave more like their natural counterparts, indicating that the ANS-tag is heat-labile, which results in a possible loss thereof.

Figure 10:
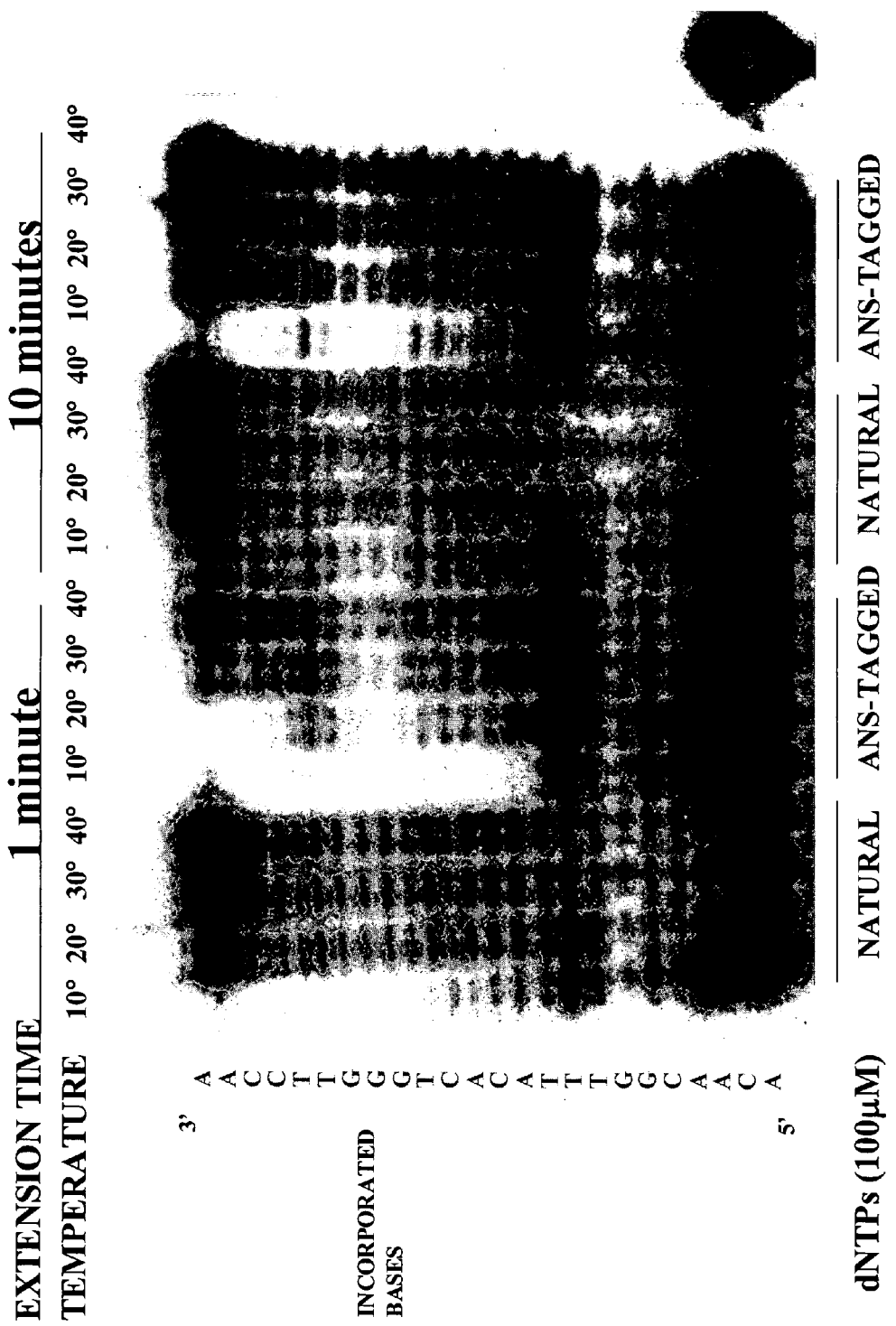
FIG. 10 depicts the effect of temperature and time on the ability of Taq DNA Polymerase to produce extended DNA products from primer/template duplexes.

Temperature and Time of Extension Can be Used to Modulate the Rate of dNTP Incorporation by Taq Polymerase This following example illustrates the effect of temperature and time on the ability of Taq DNA Polymerase to produce extended DNA products from primer/template duplexes. The reactions were carried out in extension buffer and the resulting radiolabeled products were size separated on a 10% denaturing polyacrylamide gel. Data were collected using a phosphorimaging system. Referring now to FIG. 10.

The reactions contain γ-$^{32}$P-labeled primer ('TOP') duplexed to a single-stranded template ('BOT-24') [primer/template ratio-1:9], the appropriate buffer, Taq DNA polymerase and the specified nucleotides. Lanes 1–4 contain all four natural dNTPs (100 μM, each). The reactions were carried out for 1 minute at temperatures ranging from 10 to 40° C. Lanes 5–8 contain all four ANS-γ-modified dNTPs (100 μM, each). The reactions were carried out for 1 minute at temperatures ranging from 10 to 40° C. Lanes 9–12 contain all four natural dNTPs (100 μM, each). The reactions were carried out for 10 minutes at temperatures ranging from 10 to 40° C. Lanes 13–16 contain all four ANS-γ-modified dNTPs (100 μM, each). The reactions were carried out for 10 minutes at temperatures ranging from 10 to 40° C. Lane 18 is a control containing 5' radiolabeled primer ('TOP') in extension buffer.

Quantitative comparison of lanes 1 through 4 and 5 through 8 demonstrates that temperature affects the amount of completely extended product when the reaction is carried out for 1 minute, regardless of the type of dNTPs used (natural vs γ-modified dNTPs). The same is true for lanes 9 through 12 and 13 through 16 when the reaction duration is 10 minutes. It is evident that time also affects the rate of polymerization with either types of nucleotides. Thus temperature and/or time can be used to modify polymerization rate of Taq DNA polymerase.

Figure 11:
FIG. 11 depicts the addition of an ANS-γ-tag to natural dNTPs affects the terminal transferase activity of commercially available Taq DNA Polymerase.

ANS γ-Phosphate-modification of dNTPs Affects the Terminal Transferase Activity of Taq DNA Polymerase This example demonstrates that the addition of an ANS-γ-tag to natural dNTPs affects the terminal transferase activity of commercially available Taq DNA Polymerase. The extension reactions were carried out in extension buffer at 37° C. for 30 minutes and the resulting radiolabeled products were size separated on a 10% denaturing polyacrylamide gel. Data were collected using a phosphorimaging system. Referring now to FIG. 11. Lane 1 is a control reaction and contained Taq DNA Polymerase and DNA duplex (radiolabeled 'TOP' probe and single-stranded 'BOT-24' template at equal molar concentrations). No nucleotides are added. Lane 2 contained Taq polymerase, DNA duplex and all four natural dNTPs (100 μM, each). Lane 3 contained Taq polymerase, DNA duplex and all four γ-modified dNTPs (100 μM, each).

Quantitative comparison of Lanes 2 and 3 demonstrates that in the reactions involving γ-modified dNTPs there is a substantial decrease in the terminal transferase activity of Taq DNA polymerase. The major extension product in Lane 2 is a result of this activity, while the major extension product in Lane 3 is due to a template-directed addition of nucleotides. If, however, the presence of a non-templated base is desirable or necessary for cloning or other purposes, it can be added by elevating the reaction temperature as shown in FIGS. 8 and 9 and allowing the heat treated nucleotides to act as substrates for the enzymes terminal transferase activity.

Summary of Polymerase Incorporation Results

Different Polymerases React Differently to the ANS-γ-modified Nucleotides: primer extension reactions were performed to determine the ability of various polymerases to incorporate γ-tagged dNTPs during DNA polymerization-.Control reactions contained natural dNTPs to monitor for template-directed nucleotide incorporation as well as for misincorporation as shown in FIG. 12. The reactions were performed in the appropriate buffer and contained the specified polymerase, primer/template duplex (radiolabeled 'TOP' primer annealed to 'BOT-3TC' template), and only the indicated dNTP. The reactions were carried out at room temperature or at 37° C. for 30 minutes and were stopped by the addition of 0.5 mM EDTA. The volume of the reaction was then reduced to approximately 2–4 μL, loading dye was added and the polymerization products were electrophoresed through a 20% denaturing polyacrylamide gel.Arrows indicate the position of the free labeled 'TOP'. Asterisks indicate 3-base extension.

From the data, the inventors have found that the ANS tag is thermally labile. The fact can be used to allow the construction of DNA sequences with high fidelity and low fidelity regions. Thus, a DNA polymerization can be started at low temperature using ANS γ phosphate tagged nucleotides until a give sequence length is attained (from a statistical basis) and then the temperature can be raised to liberate the ANS tag resulting in the extension of the sequence with lowered fidelity. The reverse can be done by starting with lower fidelity (untagged) nucleotides, running the polymerization for a set time, destroying any remaining untagged dNTPs with a phosphatase, and then adding the ANS tagged dNTPs and polymerizing for a second set period. Optionally, the medium can then be heated to allow a second lower fidelity region to be prepared. Thus, the present invention can be used to prepare DNA, RNA or mixed sequences having high fidelity and low fidelity regions. Such DNA, RNA or mixed sequences can be used to investigate evolutionary trends, analyzing the mutagenecity of different regions of DNA sequences, producing nucleic acid polymers that contain both highly accurate and reduced accuracy regions (in any combination or order) for mutagenesis studies (essentially targeted, random mutagenesis), or determine sites prone to mutations that result in disease states, carcinogenic states or change in cell phenotypes. The present invention also relates to method for preparing DNA, RNA or mixed sequences with regions of different fidelity indices.

The present invention also relates to the following pyrophosphorolysis inhibitors selected from the group consisting of compounds of the following general formulas or mixtures or combinations thereof:

$Z\text{-}OPO_2O\text{-}Z'$ (a)

$Z\text{-}PO_2O\text{-}Z'$ (b)

$Z\text{-}OPO_2\text{-}Z'$ (c)

$Z\text{-}PO_2\text{-}Z'$ (d)

$Z\text{-}OPO_2\text{---}(OP(EE')O)_n\text{---}PO_2O\text{-}Z'$ (e)

$Z\text{-}OPO_2\text{---}(OP(EE')O)_nPO_2\text{-}Z'$ (f)

$Z\text{-}PO_2\text{---}(OP(EE')O)_nPO_2O\text{-}Z'$ (g)

$Z\text{-}PO_2\text{---}(OP(EE')O)_nPO_2\text{-}Z'$ (h)

where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5. The term primarily means that other atoms can be present, but in very small amounts.

The present invention relates to any nucleotide or nucleotide analog bearing a tag anywhere on the nucleotide (phosphate groups, base or sugar) that improves the fidelity of nucleotide incorporation.

Different DNA Polymerases React Differently to the γ-Phosphate Modified Nucleotides Primer extension experiments were performed with several different DNA polymerases to determine whether any of them could incorporate the ANS-γ-phosphate modified nucleotides (FIG. 12). These experiments were performed by incubating the indicated polymerase in appropriate extension buffer, 100 μM ANS-γ-modified dATP, and a $5'\text{-}^{32}P$ end-labeled primer annealed to a template that directed sequential incorporation of dATP, dATP, dATP dGTP. Positive and negative control reactions containing natural dATP or dGTP, respectively, were run in parallel to monitor template-directed nucleotide incorporation or mis-incorporation. Reactions containing dATP should produce 3-base extension products, whereas those containing dGTP should not produce extended products (due to the absence of dATP). No products longer than 3-bases should result, since no reaction contained more than one nucleotide type. The reactions were allowed to proceed for 30 minutes, at which time they were stopped by EDTA addition, lyophilized and resuspended in 3.5 µl of sequencing loading buffer. Reaction products were heat denatured, loaded onto a 20% denaturing polyacrylamide gel, size-separated (2400 V; 1 hour), and detected via phosphorimaging.

The inventors observed that Taq DNA polymerase I, HIV-1 Reverse Transcriptase (RT), Klenow fragment of E. coli DNA polymerase I, and a modified version of T7 DNA polymerase (Sequenase, Version 2) each incorporate the modified nucleotides. Interestingly, the high-fidelity enzyme Pfu DNA polymerase appears least able to incorporate these nucleotides. The inventors discovered that each polymerase responded differently to the modified nucleotides. The fact that several different DNA polymerases incorporate the ANS-γ-phosphate modified nucleotides provides critical feasibility data for the VisiGen Sequencing System. Note that the expected 3-base extension products accumulate in reactions containing ANS-γ-dATP, whereas the lanes containing natural dATP or dGTP produce increased amounts of mis-extended products. Thus, the presence of the ANS-modification on the γ-phosphate appears to increase the accuracy of the reaction, and this may improve the accuracy of the VisiGen Sequencing System.

DNA Polymerase Efficiently Incorporates γ-Phosphate Modified Nucleotides

Figure 13:
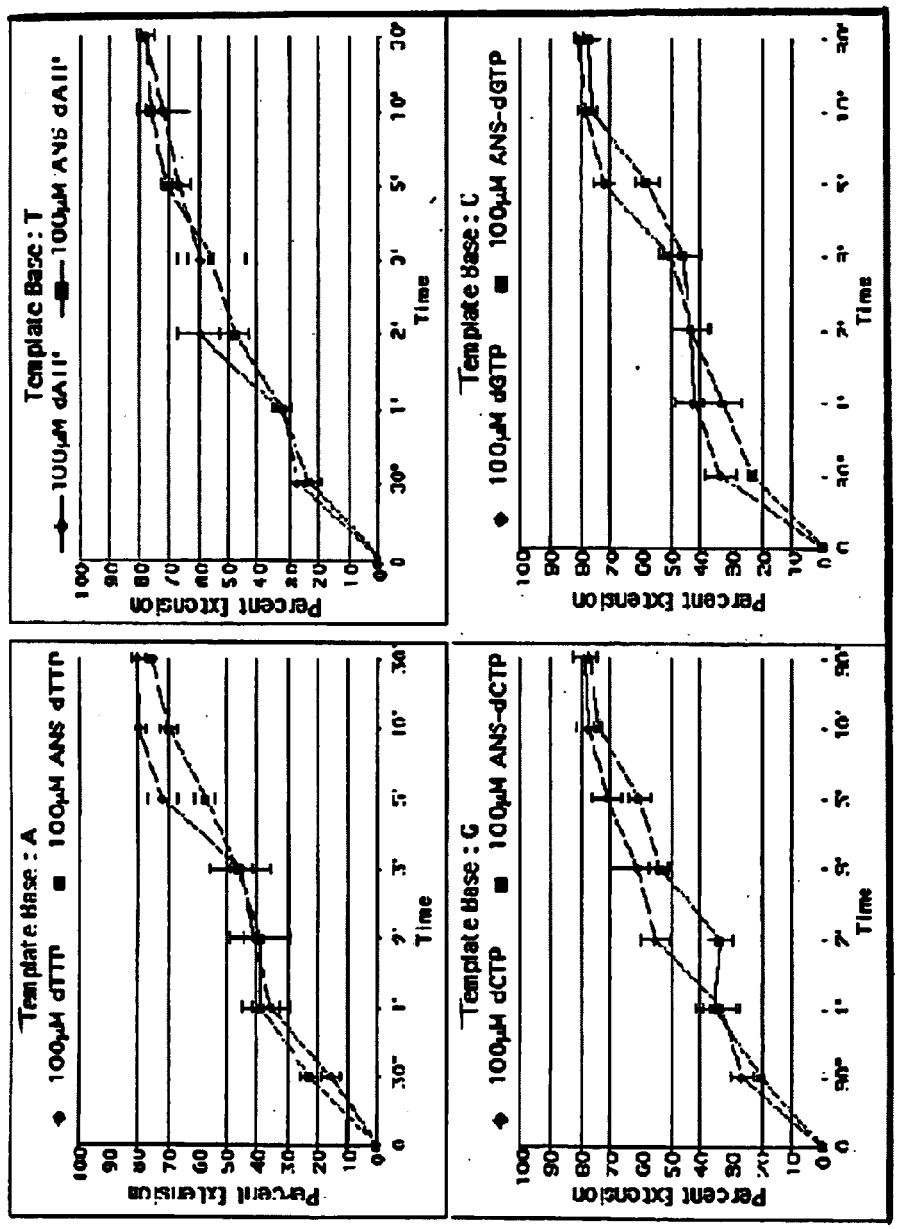
FIG. 13 depicts data from time course experiments demonstrating similar incorporation of natural and γ-phosphate modified nucleotide using HIV reverse transcriptase.

To begin to understand the unexpected observation that γ-modified dNTPs improve the accuracy at which polymerases synthesize DNA strands, the inventors investigated the incorporation efficiency of ANS-γ-modified dNTPs relative to their natural counterparts. These experiments were performed by incubating polymerase in extension buffer, 100 µM of the indicated natural or ANS-γ-modified dNTP, and a 5'-$^{32}$P end-labeled primer (TOP)/single-stranded template (BOT-'X') duplex for 0.5, 1, 2, 3, 5, 10 or 30 minutes. The sequences of the oligonucleotide templates are shown (Table 1). Intensities of non-extended primer band ($I_0$) versus extended primer band ($I_1$) were quantified with a Fuji MacBas1000 Image software version 3.0. To calculate the relative percent extension, background was first subtracted from each band value and the following calculation was applied to each reaction: Relative Percent Extension=(($I_1$)/($I_0$+$I_1$))×100. The percent extensions observed in the time course experiments are plotted and demonstrate that DNA polymerase incorporates each ANS-γ-phosphate modified nucleotide at a similar efficiency as the corresponding natural nucleotide, thus providing additional feasibility data for the VisiGen Sequencing System (FIG. 13).

γ-Phosphate Modified Nucleotides Improve Reaction Fidelity

Experiments demonstrating that commercially available Taq DNA polymerase efficiently incorporates the modified nucleotides provides feasibility data for the VisiGen Sequencing System and, unexpectedly, data demonstrating that this modification increases the fidelity of nucleotide incorporation (patent pending). In these experiments, Taq DNA polymerase (2.5 units/reaction; Promega Corporation) was incubated in polymerase reaction buffer with 10,000 cpm of 5'-$^{32}$P end-labeled 'TOP' primer, 10 ng of the indicated single-stranded template, and the specified dNTP. The sequences of the oligonucleotides are shown (Table 1). Extension reactions were incubated for 30 minutes, and terminated by the addition of 1 µl of 0.5 M EDTA. The reactions were lyophilized and resuspended in 3.5 µl of sequencing loading buffer. Reaction products were heat denatured, loaded onto a 20% denaturing polyacrylamide gel, size-separated, and quantified using a phosphorimaging system (Fuji Medical Systems, Inc.).

A representative primer extension analysis that demonstrates the fidelity improvement is shown (FIG. 3). This is an important experiment because it illustrates the following:

1) Taq DNA polymerase does not randomly incorporate γ-tagged nucleotides. Quantitative comparison of lane 1 with lane 4 demonstrates that very little non-specific, single-base extension is detected when ANS-γ-dATP is included in the reaction, but the first incorporated base should be dGTP (which was not added to the reaction). The 'BOT-Sau' template was designed to monitor sequential incorporation of dGTP, dATP, dTTP and dCTP.

2) Taq DNA polymerase accurately incorporates γ-tagged nucleotides. Quantitative analysis of lanes 1 and 8 demonstrates that approximately 70% of the TOP primer strands are extended by a template-directed single base when ANS-γ-dATP is included in the reaction and the first incorporated base should be dATP. This percentage is very similar to the percent extension observed with natural dATP (75%; lane 7). However, 60% of the extension products resulting from natural dATP incorporation were misextended opposite a template C, and 34% of these products were further extended by the enzyme's terminal transferase activity.

3) DNA strand extension continues following γ-tagged nucleotide incorporation. It was important to demonstrate that the polymerase could continue extension following incorporation of a γ-modified dNTP. This was first accomplished by preparing reactions containing the same end-labeled 'TOP' primer hybridized with the 'BOT-3TC' template, and ANS-modified dATP. Multiple occurrences of a single-base type in the extension template were used to simplify analysis of the extension products. A single nucleotide is added to the reaction and, thus, only that nucleotide can be incorporated into the growing DNA strand. Comparison of lane 1 with lane 11 demonstrates that multiple modified nucleotides are incorporated and are, therefore, not detrimental to chain extension. Natural dATP (lane 10) is efficiently incorporated opposite Ts in the template, but is also frequently misincorporated opposite a template C. Further, these blunt-ended molecules stimulate the enzyme's terminal transferase activity and account for the formation of the 5 base extension products.

4) Extension of the primer strand by incorporation of an ANS-γ-nucleotide is dependent upon Watson-Crick base pairing rules. In fact, the fidelity of nucleotide incorporation is increased by γ-phosphate modification (patent pending).

Comparison of Relative Fidelity Improvement: Single Nucleotide Extension Assays

The inventors discovered that the fidelities of several commercially relevant DNA polymerases are improved by providing the enzyme with nucleotides containing a molecular moiety at the γ-phosphate. This was further investigated by assaying the percent extension of natural and γ-phosphate modified dNTP in complementary (matched) and non-complementary (mismatched) nucleotide combinations (FIG. 14). In these experiments, TOP was 5' end-labeled, gel purified and quantified with regard to both radioactivity and absorbance at 260 nm. Primer/template hybrids were formed by heat denaturing and slow cooling primer and template strands (1:1.2 ratio). Extension reactions were prepared by combining the duplex with reaction buffer, dNTP or ANS-dNTP at 100 µM, and a DNA polymerase. To increase detection of mismatch incorporation, reactions were incubated for 30 minutes and terminated by adding STOP solution. Terminated reactions were heated, placed on ice, loaded onto a 20% denaturing polyacrylamide gel and electrophoresed for ~2 hours at 30 W. Gels were dried and imaged with a phosphorimaging system (Fuji Medical Systems, Inc.). Each reaction was repeated at least three times, and the average extension and average deviation were calculated.

Interestingly, the magnitude of the fidelity improvement is influenced by the identity of the templating base versus the incoming nucleotide. As an example, C:T provides a different magnitude of improvement (15.98 fold) when compared to T:C (2.93 fold), where the first base is the template base and the second base is the incoming nucleotide. Comparing the percent extension of a natural dNTP with that of an ANS-modified dNTP, it is striking that the modified nucleotide is consistently incorporated at an improved accuracy. Additionally, the time course studies show that the incorporation of the complementary nucleotide (natural or ANS-modified) exhibit similar incorporation profiles, indicating that the fidelity improvements are not due to generally slowed reaction kinetics resulting from nucleotide modification.

Kinetic analysis of the ANS-γ-phosphate fidelity affect is warranted in Phase II of the project since similar nucleotides will be used in the VisiGen Single-Molecule Sequencing System. It is likely that these nucleotides will exhibit altered incorporation fidelities, similar to the ANS-modified nucleotides. If increased fidelity is associated with incorporation of the fluorescently-modified nucleotides designed for the VisiGen Sequencing System, the accuracy of the single molecule sequence will increase and the number of reactions that need to be performed in parallel to obtain highly accurate information will decrease.

The fidelity improving nucleotides—"Designer Nucleotides"—are being pursued as a VisiGen intermediate product. We anticipate a shorter route to this product. VisiGen's designer nucleotides will improve the accuracy at which a DNA strand is synthesized and should be quite useful in any enzymatic extension assay (patent pending). Perhaps derivatives of these nucleotides will enable highly accurate in vitro DNA synthesis that rivals, or possibly exceeds, the accuracy at which a DNA strand is replicated in vivo. Thus, Phase II of our project, "Real-time DNA Sequencing: Nucleotide Synthesis and Use", will support kinetic analysis and M13 forward mutation assays of ANS-modified nucleotides. Data from these studies will define the 'fidelity factor' for each modified nucleotide, and enable us to better understand the importance of the modification relative to the natural nucleotide. It is unlikely that the first molecular moiety chosen, ANS, is the one that produces the optimal designer nucleotide. Future studies (not supported by this award), will define the parameters that affect replication fidelity by examining the contribution of specific tag modifications on matched versus mismatched nucleotide selection. However, the kinetic and forward mutation studies supported by a Phase II award will provide feasibility data that will enable us to begin discussions with larger companies and/or private investors interested in either a short- or long-term technology—designer nucleotides that improve reaction fidelity and single-molecule DNA sequencing, respectively.

Chemically Engineer Nucleotides (NIH Phase II)

Synthesis of γ- and/or β-modified and 3'-modified dNTP

Potential candidate compounds for use in our FRET or quenching detection of polymerase reactions are summarized in the following synthetic scheme:

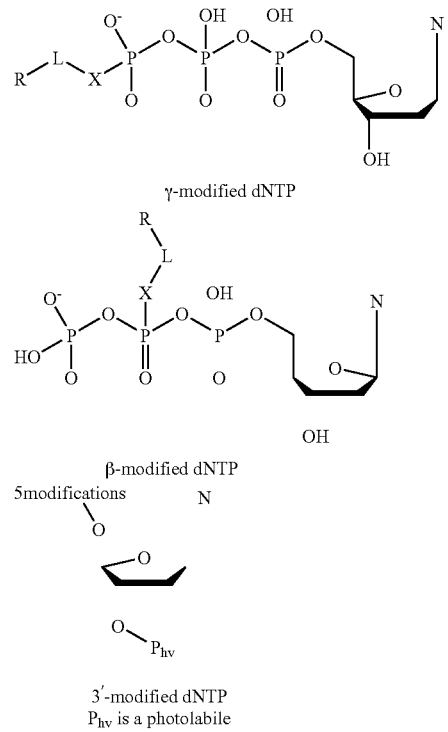

In above scheme, N=A, C, G, T; X=O, N, S, $CH_2$, etc.; L=linker, such as —$(CH_2)_n$—, —$(CH_2CH_2O)_2$—; R=fluorophore or quencher moieties, such as ANS, FAM, FITC, rhodamine, cyanine, pyrene, perylene; $P_{hv}$ is a photolabile group.

These modified dNTPs can be sued to identify a set of nucleotides that work with modified polymerase as an energy transfer pair to achieve high efficiency and accurate sequence reading. The positions that are of interest are the 5'-γ and 5'-β, since the modifications at these positions may not or least affect enzyme activity. The inventors plan to incorporate rhodamine derivatives, such as TMR or TAMRA, for FRET detection and DABCYL for quenching detection (the enzyme in using either type of dNTP'S will contain fluorescein moiety). An additional linker (L) between the dye moiety and phosphorous provides flexibility to obtain better fir of the nucleotide and the enzymatic active site and may provide stabilization to the resultant modified compound. The alteration at the phosphorous linkage is preferably an O (X=O). For all 5-modified dNTP's, if the 3'-OH is not blocked, the sequence will proceed continuously. The protection of the 3'-O position with a photolabile group causes reaction to pause after the addition of a dNTP. The sequence extension can continue after photo-deprotection of the 3'-$P_{hv}$. The 3'-protection is to be used along with 5'-modifications to overcome potential problems of background reading from fluorescent nucleotides.

Specifically, examples of the compounds the inventors plan to synthesize are the following: Set 1—these are 5'-γ or β-modifications, different dyes are needed so that different nucleotides can be differentiated by different wavelengths. These are the d-rhodamine family of molecules and have been widely used in traditional DNA sequencing. The linker and connector, $HNCH_2CH_2O$ will be varied to achieve the best result.

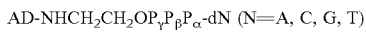

AD-NHCH$_2$CH$_2$OP$_\gamma$P$_\beta$P$_\alpha$-dN (N=A, C, G, T)

P$_\gamma$(AD-NHCH$_2$CH$_2$O)P$_\beta$P$_\alpha$-dN (N=A, C, G, T)

where AD: acceptor dye molecule, AD is selected from Lee et al., 1997; AD=5dR110, 5dR6G, 5dTMR, 5dROX Set 2—These are 5'-quencher (Q),3'-P$_{hv}$ modifications. Our laboratory has used this photolabile group in the synthesis of several photogenerated reagents, and have studied this reaction in great detail.

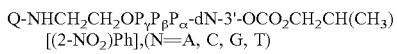

Q-NHCH$_2$CH$_2$OP$_\gamma$P$_\beta$P$_\alpha$-dN-3'-OCO$_2$CH$_2$CH(CH$_3$)
[(2-NO$_2$)Ph],(N=A, C, G, T)

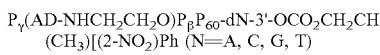

P$_\gamma$(AD-NHCH$_2$CH$_2$O)P$_\beta$P$_{60}$-dN-3'-OCO$_2$CH$_2$CH
(CH$_3$)[(2-NO$_2$)Ph (N=A, C, G, T)

The inventors will closely monitor the results of our experiments and implement changes in our synthesis plan as necessary.

The synthesis of γ-modified triphosphates will begin with typical reactions for triphosphate esterification, using a coupling reagent such as that shown in the Phase I Final Project Report section for the synthesis of γ-ANS-dATP. Although the reaction is simple, the isolation of the product requires great care since the compound may not be quite stable. For separation of the ANS dNTP products, low temperature was used and light must be kept away in the process. Rhodamine molecules are not stable under basic conditions and caution will be taken. However, since the inventors have had long time experiences in synthesis and there is a large of amount of information on the type of chemistry which can be used, the inventors do not anticipate significant problems. The synthesis of β-modified dNTP will require first protecting the active γ-phosphate. The inventors do not intend to spend major effort in making these compounds, unless the β-modified molecule is a strong candidate with desirable sequencing properties. To connect the linker with dye on one side and nucleotide on the other side, the inventors prefer to have amide and phosphate bonds, respectively. The bond formation of the linker is through well-known coupling reactions (through isothiocyannate ester, or NHS ester, etc.).

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

SEQUENCE LISTING

```
<160> NUMBER OF SEQ ID NOS: 9

<210> SEQ ID NO 1
<211> LENGTH: 7
<212> TYPE: DNA
<213> ORGANISM: Artificial
<220> FEATURE:
<223> OTHER INFORMATION: The sequences listed here are artifically
      generated DNA sequences synthesized to test fidelity of monomer
      incorporation due to substitution at the gamma phosphate of the
      dNTPs.
<220> FEATURE:
<221> NAME/KEY: Oligonucleotide
<222> LOCATION: (1)..(7)
<223> OTHER INFORMATION: An example of an oligonucleotide discussed the
      in the definition section of the application.

<400> SEQUENCE: 1 atgcctg                                                             7

<210> SEQ ID NO 2
<211> LENGTH: 19
<212> TYPE: DNA
<213> ORGANISM: Artificial
<220> FEATURE:
<223> OTHER INFORMATION: This sequence is a primer strand for Taq DNA
      polymerase.
<220> FEATURE:
<221> NAME/KEY: primer_bind
<222> LOCATION: (1)..(19)
<223> OTHER INFORMATION: Primer strand for Taq DNA polymerase

<400> SEQUENCE: 2
ggtactaagc ggccgcatg                                                19
```

<210> SEQ ID NO 3
<211> LENGTH: 20
<212> TYPE: DNA
<213> ORGANISM: Artificial
<220> FEATURE:
<223> OTHER INFORMATION: Template Strand - antisense to the primer
      strand of sequence 2 with the addition of a T residue at the end
      of the strand designated BOT-T 3'.
<220> FEATURE:
<221> NAME/KEY: Template
<222> LOCATION: (1)..(19)
<223> OTHER INFORMATION: Anti-sense to the primer sequence 2.

<400> SEQUENCE: 3
ccatgattcg ccggcgtact                                          20

<210> SEQ ID NO 4
<211> LENGTH: 20
<212> TYPE: DNA
<213> ORGANISM: Artificial
<220> FEATURE:
<223> OTHER INFORMATION: Template Strand - antisense to the primer
      strand of sequence 2 with the addition of a C residue at the end
      of the strand designated BOT-C 3'.
<220> FEATURE:
<221> NAME/KEY: Template
<222> LOCATION: (1)..(19)
<223> OTHER INFORMATION: Anti-sense to the primer sequence 2.

<400> SEQUENCE: 4
ccatgattcg ccggcgtacc                                          20

<210> SEQ ID NO 5
<211> LENGTH: 20
<212> TYPE: DNA
<213> ORGANISM: Artificial
<220> FEATURE:
<223> OTHER INFORMATION: Template Strand - antisense to the primer
      strand of sequence 2 with the addition of a G residue at the end
      of the strand designated BOT-G 3'.
<220> FEATURE:
<221> NAME/KEY: Template
<222> LOCATION: (1)..(19)
<223> OTHER INFORMATION: Anti-sense to the primer sequence 2.

<400> SEQUENCE: 5
ccatgattcg ccggcgracg                                          20

<210> SEQ ID NO 6
<211> LENGTH: 20
<212> TYPE: DNA
<213> ORGANISM: Artificial
<220> FEATURE:
<223> OTHER INFORMATION: Template Strand - antisense to the primer
      strand of sequence 2 with the addition of a A residue at the end
      of the strand designated BOT-A 3'.
<220> FEATURE:
<221> NAME/KEY: Template
<222> LOCATION: (1)..(19)
<223> OTHER INFORMATION: Anti-sense to the primer sequence 2.

<400> SEQUENCE: 6
ccatgattcg ccggcgtaca                                          20

<210> SEQ ID NO 7
<211> LENGTH: 23
<212> TYPE: DNA
<213> ORGANISM: Artificial
<220> FEATURE:

```
<223> OTHER INFORMATION: Template Strand - antisense to the primer
      strand of sequence 2 with the addition of a TAG residues at the
      end of the strand designated BOT-Sau 3'.
<220> FEATURE:
<221> NAME/KEY: Template
<222> LOCATION: (1)..(19)
<223> OTHER INFORMATION: Anti-sense to the primer sequence 2.

<400> SEQUENCE: 7
ccatgattcg ccggcgtacc tag                                            23

<210> SEQ ID NO 8
<211> LENGTH: 21
<212> TYPE: DNA
<213> ORGANISM: Artificial
<220> FEATURE:
<223> OTHER INFORMATION: Template Strand - antisense to the primer
      strand of sequence 2 with the addition of a TC residues at the end
      of the strand designated BOT-TC 3'.
<220> FEATURE:
<221> NAME/KEY: Template
<222> LOCATION: (1)..(19)
<223> OTHER INFORMATION: Anti-sense to the primer sequence 2.

<400> SEQUENCE: 8
ccatgattcg ccggcgtact c                                              21

<210> SEQ ID NO 9
<211> LENGTH: 23
<212> TYPE: DNA
<213> ORGANISM: Artificial
<220> FEATURE:
<223> OTHER INFORMATION: Template Strand - antisense to the primer
      strand of sequence 2 with the addition of a TTTC residues at the
      end of the strand designated BOT-3TC 3'.
<220> FEATURE:
<221> NAME/KEY: Template
<222> LOCATION: (1)..(19)
<223> OTHER INFORMATION: Anti-sense to the primer sequence 2.

<400> SEQUENCE: 9
ccatgattcg ccggcgtact ttc                                            23
```

We claim:

1. A method for using modified nucleotides to alter base incorporation fidelity comprising the step of adding a modified nucleotide including a molecular tag to a nucleotide polymerization medium comprising a nucleotide polymerizing agent, a primer, a template, and a pyrophosphorolysis inhibitor selected from the group consisting of compounds of the following general formulas and mixtures or combinations thereof:

$$Z\text{-}OPO_2O\text{-}Z' \qquad (a)$$

$$Z\text{-}PO_2O\text{-}Z' \qquad (b)$$

$$Z\text{-}OPO_2\text{-}Z' \qquad (c)$$

$$Z\text{-}PO_2\text{-}Z' \qquad (d)$$

$$Z\text{-}OPO_2\text{--}(OP(EE')O)_n\text{--}PO_2O\text{-}Z' \qquad (e)$$

$$Z\text{-}OPO_2\text{--}(OP(EE')O)_nPO_2\text{-}Z' \qquad (f)$$

$$Z\text{-}PO_2\text{--}(OP(EE')O)_nPO_2O\text{-}Z' \qquad (g)$$

$$Z\text{-}PO_2\text{--}(OP(EE')O)_nPO_2\text{-}Z' \qquad (h)$$

where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5, where the modified nucleotide increases base incorporation fidelity of the nucleotide polymerizing agent relative to a base incorporation fidelity of the nucleotide polymerizing agent in the absence of the modified nucleotide to produce an extended primer having reduced incorrect base incorporations and where the pyrophosphorolysis inhibits pryosphosphorolysis reduces the amount of pyrophosphorolysis occurring in the reaction.

2. The method of claim 1, wherein the modified nucleotide comprises a β and/or γ phosphate modified nucleotide.

3. The method of claim 1, wherein the modified nucleotide comprises a β phosphate modified nucleotide.

4. The method of claim 1, wherein the modified nucleotide comprises a γ phosphate modified nucleotide.

5. The method of claim 4, wherein the tag comprises aminonaphthalene-1-sulfonate (ANS).

6. A method for using modified nucleotides to alter base incorporation fidelity comprising the step of adding a modified nucleotide including a molecular tag to an assay for extending a nucleotide sequence, and a pyrophosphorolysis inhibitor selected from the group consisting of compounds of the following general formulas and mixtures or combinations thereof:

$$Z\text{-}OPO_2O\text{-}Z' \quad (a)$$

$$Z\text{-}PO_2O\text{-}Z' \quad (b)$$

$$Z\text{-}OPO_2\text{-}Z' \quad (c)$$

$$Z\text{-}PO_2\text{-}Z' \quad (d)$$

$$Z\text{-}OPO_2\text{---}(OP(EE')O)_n\text{---}PO_2O\text{-}Z' \quad (e)$$

$$Z\text{-}OPO_2\text{---}(OP(EE')O)_nPO_2\text{-}Z' \quad (f)$$

$$Z\text{-}PO_2\text{---}(OP(EE')O)_nPO_2O\text{-}Z' \quad (g)$$

$$Z\text{-}PO_2\text{---}(OP(EE')O)_nPO_2\text{-}Z' \quad (h)$$

where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5 and where the modified nucleotide alters base incorporation fidelity of a nucleotide polymerizing agent relative to abase incorporation fidelity of the polymerizing agent in the absence of the modified nucleotide, and the assay is selected from the group consisting of genotyping for in vitro reproductive methods (human and other organisms); single nucleotide polymorphism (SNP) detection; DNA sequencing; RNA sequencing; single nucleotide extension assays; amplified DNA product assays; rolling circle product assays; PCR product assays; allele-specific primer extension assays; single-molecule arrays (DNA, RNA, protein) assays; and drug toxicity evaluation assays.

7. A kit for performing a nucleotide polymerizing reaction comprising using at least one modified nucleotide including a molecular tag in the presence of a polymerizing agent, a primer, a template and a pyrophosphorolysis inhibitor selected from the group consisting of compounds of the following general formulas and mixtures or combinations thereof:

$$Z\text{-}OPO_2O\text{-}Z' \quad (a)$$

$$Z\text{-}PO_2O\text{-}Z' \quad (b)$$

$$Z\text{-}OPO_2\text{-}Z' \quad (c)$$

$$Z\text{-}PO_2\text{-}Z' \quad (d)$$

$$Z\text{-}OPO_2\text{---}(OP(EE')O)_n\text{---}PO_2O\text{-}Z' \quad (e)$$

$$Z\text{-}OPO_2\text{---}(OP(EE')O)_nPO_2\text{-}Z' \quad (f)$$

$$Z\text{-}PO_2\text{---}(OP(EE')O)_nPO_2O\text{-}Z' \quad (g)$$

$$Z\text{-}PO_2\text{---}(OP(EE')O)_nPO_2\text{-}Z' \quad (h)$$

where Z or Z' is a hydrogen atom or a thermally stable substituent comprising primarily one or more atoms selected from the group carbon, nitrogen, oxygen, sulfur and phosphorus with sufficient hydrogen atoms to satisfy valence requirements, E and E' are an oxygen atom or a thermally stable substituent comprising primarily one or more atoms selected from the group carbon, nitrogen, oxygen, sulfur and phosphorus with sufficient hydrogen atoms to satisfy valence requirements and n is an integer having a value between 0 and about 5 and where the modified nucleotide alters polymerizing agent extension fidelity for the at least one modified nucleotide compared to the polymerizing agent extension fidelity in the presence of the unmodified nucleotide corresponding to the at least one modified nucleotide.

8. The method of claim 1, wherein the tag is-covalently bonded to the modified nucleotide through a linker.

9. The method of claim 1, wherein the tag is covalently bonded to the modified nucleotide.

10. The method of claim 4, wherein the molecular tag comprises a fluorophore selected from the group consisting of 4-acetamido-4isothiocyanatostilbene-2,2'disulfonic acid; acridine and derivatives: acridine, acridine isothiocyanate; 5-(2'-aminoethyl) aminonaphthalene-1-sulfonic acid (EDANS); 4-amino-3-vinylsulfonyl)phenyl]naphthalimide-3,5 disulfonate; -(4-anilino-lnaphthyl)maleimide; anthranilamide; BODIPY; Brilliant Yellow; coumarin and derivatives: coumarin, 7-amino-4-methylcoumarin (AMC, Coumarin 120), 7-amino-4trifluoromethylcouluarin (Coumaran 151); cyanine dyes; cyanosine; 4',6-diaminidino-2phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4' diisothiocyanatostilbene-2,2'-disulfonic acid; 5-dimethylamino naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5carboxyfluorescein (FAM), 5-(4,6-dichlorotriazin-2-yl) aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (CibacronTM Brilliant Red 3B-A) rhodamine and derivatives: 6-carboxy-X-rhodamine (ROX), 6carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N, N, N', N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

11. The method of claim 4, wherein the molecular tag is selected from the group consisting of alkyl groups having between 1 and 30 carbon atoms, aryl groups having between about 6 and about 40 carbon atoms, or alkaryl and aralkyl groups having between about 7 and about 40 carbon atoms, or mixture or combinations thereof, where the carbon atoms are replace by one or more hetero atoms in the structure provided the structure represents a stable molecular system, where the hetero atoms selected from the group consisting of P, S, Si, N, and O.

12. The method of claim 4, wherein the molecular tag is selected from the group consisting of 4-aminophenol, 6-aminonaphthol, 4-nitrophenol, 6-nitronaphthol, 4-methylphenol, 6-chloronaphthol, 4-methoxyphenol, 6-bromonaphthol, 4-chlorophenol, 6-iodonaphthol, 4-bromophenol, 4,4'-dihydroxybiphenyl, 4-iodophenol, 8-hydroxyquinoline, 4-nitronaphthol, 3-hydroxypyridine, 4-aminonaphthol, umbelliferone, 4-methylnaphthol, resorufin, 4-methoxynaphthol, 8-hydroxypyrene, 4-chloronaphthol, 9-hydroxyanthracene, 4bromonaphthol, 6-nitro-9-hydroxyanthracene, 4-iodonaphthol, 3-hydroxyflavone, 6-methylnaphthol, fluorescein, 6-methoxynaphthol, 3-hydroxybenzoflavone, 1-hydroxy-2-propyne, 1-hydroxy-4-pentyne, 1-hydroxy -3-butyne, 1-hydroxy-5-hexyne, Methanol, Ethanol, Propanol, Isopropanol, Butanol, Tert-butanol, Hexanol, Cyclohexanol, Heptanol, Octanol, Decanol, Undecanol, Dodecanol, 1-acetoxymethanol (CH3OOCCH2-O-NTP), 2-acetoxyethanol, 3-acetoxypropanol, 4-acetoxybutanol, 5-acetoxypentanol, 6-acetoxyhexanol, 2-nitroethanol, 3-nitropropanol, 4-nitrobutanol, 5-nitropentanol, 5-nitrohexanol, 1-hydroxy-3-propene, 1-hydroxy-2-cyclohexene, 1-hydroxy-4-butene, 1 -hydroxy-3-propaldehyde, 1-hydroxy-5-pentene, 1-hydroxy-4-butanaldehyde, 1-hydroxy-6-hexene, 1-hydroxy-3-Butanone, Phenol, 4-methyl-3-hydroxypyridine, 4-Carboxyphenol, 5-methoxy-3-hydroxypyridine, 4-Acetoxymethylphenol, 5-nitro-3-hydroxypyridine, 4-nitrophenol, 5-acetoxymethyl-3-hydroxypyridine, 4-methylphenol, 6-methyl-8-hydroxyquinoline, 4-methoxyphenol 6-methoxy-8-hydroxyquinoline, 4-ethylphenol, 4-methyl-8-hydroxyquinoline, 4-butylphenol, 6-nitro-8-hydroxyquinoline, naphthol, 4-acetoxymethyl-8-hydroxyquinoline, 4 or 6 or 8 methylnaphthol pyrene, 4 or 6 or 8 methoxynaphthol, 6-methyl-8-hydroxypyrene, 4 or 6 or 8 nitronaphthol, 6-ethyl-8-hydroxypyrene, 4 or 6 or 8 ethylnaphthol, 6-nitro-8-hydroxypyrene, 4 or 6 or 8 butylnaphthol 6-(carboxysuccinimidylester)fluorescein, 4 or 6 or 8 acetoxymethylnaphthol, 6-carboxymethyl-2,7-dichlorofluorescein, Methanol Cyclohexanol, 2-carboxy ethanol, 3-carboxypropanol, 4-carboxybutanol, 2-hydroxyethanol, 3-hydroxypropanol, 4-hydroxybutanol, 2-aminoethanol, 2-nitroethanol, 3-aminopropanol, 3-nitropropanol, 4-aminobutanol, and 4-nitrobutanol.

13. The method of claim 4, wherein the modified nucleotide is selected from the group consisting of Adenosine-5'-(γ-ANS)triphosphate, Guanosine-5'-(γ-ANS) triphosphate, Cytosine-5'-(γ-ANS)triphosphate, Thymidine-5'-(γ-ANS)triphosphate, Adenosine-5'-(γ-4-nitrophenyl) triphosphate, Adenosine-5'-(γ-4-iodonaphthyl), Guanosine-5'-(γ-4-nitrophenyl)triphosphate, triphosphate Adenosine-5'-(γ-6-methylnaphthyl)triphosphate, Cytosine-5-(γ-4-nitrophenyl)triphosphate, Thymidine-5'-(γ-4-nitrophenyl) triphosphate, Adenosine-5'-(γ-6-methoxynaphthyl) triphosphate, Uracil-5'-(γ-4-nitrophenyl)triphosphate, 3-azido-3'-deoxythymidine-5'-(γ4 nitrophenyl)triphosphate, Adenosine-5'-(γ-6-aminonaphthyl)triphosphate, 3'-azido-2', 3'-dideoxythymidine-5'-(γ-4-nitrophenyl)triphosphate, Adenosine-5'-(γ-6-nitronaphthyl)triphosphate, 2',3'-didehydro-2',3'-dideoxythymidine-5'-(γ-4-nitrophenyl)triphosphate, Adenosine-5'-(γ-6-chloronaphthyl)triphosphate, Adenosine-5'-(γ-4-aminophenyl)triphosphate, Adenosine-5-(γ-6-bromonaphthyl)triphosphate, Adenosine-5'-(γ-4-methylphenyl)triphosphate, Adenosine-5'-(γ-6-iodonaphthyl) triphosphate, Adenosine-5'-(γ-4-methoxyphenyl) triphosphate, Adenosine-5'-(γ-4'-hydroxybiphenyl) triphosphate, Adenosine-5'-(γ-4-chlorophenyl)triphosphate, Adenosine-5'-(γ-8-quinolyl)triphosphate, Adenosine-5'-(γ-4-bromophenyl)triphosphate, Adenosine-5'-(γ-3-pyridyl) triphosphate, Adenosine-5'-(γ-umbelliferone), Adenosine-5'-(γ-4-iodophenyl)triphosphate, Adenosine-5'-(γ-4-nitronaphthyl) triphosphate, Adenosine-5'-(γ-resorufin) triphosphate, Adenosine-5'-(γ-pyrene)triphosphate, Adenosine-5'-(γ-4-aminonaphthyl)triphosphate, Adenosine-5'-(γ-anthracene)triphosphate, Adenosine5'-(Γ-6-nitroanthracene)triphosphate, Adenosine-5'-(γ-4-methylnaphthyl) triphosphate, Adenosine-5'-(γ-flavonyl)triphosphate, Adenosine-5'-(γ-4-methoxynaphthyl)triphosphate, Adenosine-5'-(γ-fluorescein)triphosphate, Adenosine-5'-(γ-benzoflavone)triphosphate, Adenosine-5'-(γ-4-chloronaphthyl) triphosphate, Adenosine-5'-(γ-(4-nitrophenyl)-γ'-(4-aminophenyl)triphosphate, Adenosine-5'-(γ-4-bromonaphthyl)triphosphate, Adenosine-5'-(γ-(4-nitrophenyl)-γ'-(4-nitronaphthyl)triphosphate, Adenosine-5'-(γ-methyl)triphosphate, Adenosine-5'-(γ-acetoxypropyl) triphosphate, Guanosine-5'-(γ-methyl)triphosphate, Cytosine-5'-(γ-methyl) triphosphate, Adenosine-5'-(γ-acetoxymethyl)triphosphate(CH3OOCCH,—O—NTP), Thymidine-5'-(γ-methyl)triphosphate, Uracil-5'-(γ-methyl)triphosphate, Adenosine-5'-(γ-acetoxyethyl) triphosphate, 3'-azido-3'-deoxythymidine-5-(γ-methyl)triphosphate, Adenosine-5-(γ-acetoxybutyl)triphosphate, 3'-azido-2',3'-dideoxythymidine-5'-(γ-methyl)triphosphate, Adenosine-5'-(γ, acetoxypentyl)triphosphate,2',3'-didehydro-2',3'-dideoxythymidine-5'-(γ-methyl) triphosphate, Adenosine-5'-(γ-acetoxyhexyl)triphosphate, Adenosine-5'-(γ-ethyl) triphosphate, Adenosine-5'-(γ-2-nitroethyl)triphosphate, Adenosine-5'-(γ-propyl)triphosphate, Adenosine-5'-(γ-4-butyl)triphosphate, Adenosine-5'-(γ-3-nitropropyl)triphosphate, Adenosine-5'-(γ-hexyl) triphosphate, Adenosine-5'-(γ-octyl)triphosphate, Adenosine-5'-(γ-4-nitrobutyl) triphosphate, Adenosine-5'-(γ-decyl)triphosphate, Adenosine-5'-(γ-dodecyl)triphosphate, Adenosine-5'-(γ-5-nitropentyl)triphosphate, Adenosine-5'-(γ-isopropyl)triphosphate, Adenosine-5'-(γ-tert-butyl) triphosphate, Adenosine-5'-(γ-methyl)-(γ'-ethyl)triphosphate, Adenosine-5'-(γ-cyclohexyl) triphosphate, Adenosine-5'-(γ-methyl)-(γ'-propyl)triphosphate, Adenosine-5'-(γ-2-propenyl) triphosphate, Adenosine-5'-(γ-3-butenyl)triphosphate, Guanosine-5'-(γ-2-propenyl)triphosphate, Adenosine-5-(γ-4-pentenyl)triphosphate, Cytosine-5'-(γ-2-propenyl)triphosphate, Adenosine-5'-(γ-5-hexenyl)triphosphate, Thymidine-5'-(γ-2-propenyl)triphosphate, Adenosine-5-(γ-cyclohexenyl)triphosphate, Uracil-5'-(7-2-propenyl) triphosphate, Adenosine-5'-(γ-3-propanaldehyde) triphosphate, 3'-azido-3'-deoxythymidine-5'-(γ-2-propenyl) triphosphate, Adenosine-5-(γ-4-butanaldehyde)triphosphate, 3'-azido-2',3'-dideoxythymidine-5'-(γ-2-propenyl) triphosphate, Adenosine-5'-(γ-3-butanone)triphosphate, 2',3'-didehydro-2', 3'-dideoxythymidine-5'-(γ-2-propenyl) triphosphate, Adenosine-5'-(γ-2-propynyl)triphosphate, 3'-azido-2', 3'-dideoxythymidine-5'-(γ-2-propynyl)triphosphate, Guanosine-5'-(γ-2-propynyl)triphosphate, Cytosine-5'-(γ-2-propynyl)triphosphate, 2',3'-didehydro-2',3'-dideoxythymidine-5'-(γ2-propynyl)triphosphate Thymidine 5'-(γ-2-propynyl)triphosphate, Uracil-5'-(γ-2-propynyl) triphosphate, Adenosine-5'-(γ-3-butynyl)triphosphate, 3'-azido-3'-deoxythymidine-5'-(γ-2-propynyl)triphosphate, Adenosine-5-(γ-4-pentynyl)triphosphate, Adenosine-5'-(γ-5-pentynyl) triphosphate, Adenosine-5'-(γ-4-phenyl)triphosphate, Adenosine-5'-(γ-(4 or 6 or 8 acetoxymethyl naphthyl) triphosphate, Guanosine-5'-(γ-4-phenyl)triphosphate, Cytosine-5'-(γ-4-phenyl) triphosphate, Adenosine-5'-(γ-(4- methylpyridyl)triphosphate, Thymidine-5'-(γ-4-phenyl) triphosphate, Uracil-5'-(γ-4-phenyl)triphosphate, Adenosine-5'-(γ-(5-methoxypyridyl)triphosphate, 3'-azido-3'-deoxythymidine-5'-(γ4-phenyl)triphosphate, Adenosine-5'-(γ(5-nitropyridyl)triphosphate, 3'-azido-2',3'-dideoxythymidine-5'-(γ-4-phenyl)triphosphate, Adenosine-5'-(γ-(5-acetoxymethylpyridyl)triphosphate, 2',3'-didehydro-2',3'-dideoxythymidine-5'-(γ-4-phenyl)triphosphate, Adenosine-5'-(γ-(6-methyl-1-quinolyl)triphosphate, Adenosine-5'-(γ-4-carboxyphenyl)triphosphate, Adenosine-5'-(γ-(6-methoxy-1-quinolyl)triphosphate,Adenosine-5'-(γ-(4-acetoxymethyl) phenyl)triphosphate, Adenosine-5'-(γ-(4-methyl-1-quinolyl) triphosphate, Adenosine-5'-(γ-4-nitrophenyl)triphosphate, Adenosine-5'-(γ4-methylphenyl)triphosphate,Adenosine-5'-(γ-(6-nitro-1-quinolyl)triphosphate, Adenosine-5'-(γ-4-methoxyphenyl)triphosphate, Adenosine-5'-(γ-(4-acetoxymethylpyrenyl)triphosphate, Adenosine-5'-(γ-4-ethylphenyl) triphosphate, Adenosine-5'-(γ-(6-methylpyrenyl) triphosphate, Adenosine-5'-(γ-4-butylphenyl)triphosphate, Adenosine 5'-(γ-naphthyl)triphosphate, Adenosine-5'-(γ-(6-ethylpyrenyl)triphosphate, Adenosine-5'-(γ-(4 or 6 or 8 methyl naphthyl)triphosphate, Adenosine-5'-(γ-(6-nitropyrenyl)triphosphate, Adenosine-5'-('-(4 or 6 or 8 methoxynaphthyl) triphosphate, Adenosine-γ-(γ-6-(carboxysuccinimidyl fluorescein)triphosphate, Adenosine-5'-(γ-(4 or 6 or 8 nitro naphthyl)triphosphate. Adenosine-5 (γ-6-carboxymethyl-2,7-dichlorofluorescein) triphosphate, Adenosine-5'-(γ-(4 or 6 or 8 ethyl naphthyl)triphosphate, Adenosine-5'-(γ-4-phenyl)-(γ'-4 nitrophenyl)triphosphate, Adenosine-5'-(γ-(4 or 6 or 8 butyl naphthyl)triphosphate, Adenosine-5'-(γ-4-phenyl)-(γ'-4 aminophenyl)triphosphate, Adenosine-5'-(γ-methyl)triphosphate, Adenosine-5'-(γ-3-aminopropyl) triphosphate, Guanosine-Y-(γ-methyl)triphosphate, Adenosine-5'-(γ-4-aminobutyl)triphosphate, Cytosine-5'-(γ-methyl)triphosphate Adenosine-5'-(γ-cyclohexyl) triphosphate, Thymidine-5'-(γ-methyl)triphosphate Adenosine-5'-(γ-2-carboxyethyl) triphosphate, Uracil-5'-(γ-methyl) triphosphate, Adenosine-5'-(γ-3-carboxypropyl) triphosphate, 3'-azido-3'-deoxythymidine-5'-(7-methyl) triphosphate, Adenosine-5'-(γ-4-carboxybutyl) triphosphate, 3'-azido-2',3'-dideoxythymidine-5'-(γ-methyl) triphosphate, Adenosine-5'-(γ-2-hydroxyethyl)triphosphate, 2',3'-didehydro-2',3'-dideoxythymidine-5'-(γ-methyl)triphosphate, Adenosine-5'-(γ-3-hydroxypropyl)triphosphate, Adenosine-5'-(γ-ethyl)triphosphate, Adenosine-5'-(γ-propyl)triphosphate, Adenosine-5'-(γ-4-hydroxybutyl)triphosphate, Adenosine-5'-(γ-4-butyl) triphosphate, Adenosine-5'-(γ-2-nitroethyl)triphosphate, Adenosine-5'-(γ-hexyl) triphosphate, Adenosine-5'-(γ-3-nitropropyl)triphosphate, Adenosine-5'-(γ-isopropyl) triphosphate, Adenosine-5'-(γ-4-nitrobutyl)triphosphate, Adenosine-5'-(γ-tert-butyl) triphosphate, Adenosine-5'-(γ-methyl)-(γ'-ethyl) triphosphate, Adenosine-5'-(γ-cyclohexyl)triphosphate, Adenosine-5'-(γ-2-aminoethyl)triphosphate, and Adenosine-5'-(γ-methyl)-(γ'-propyl) triphosphate.

14. The method of claim 6, wherein the tag is covalently bonded to the modified nucleotide through a Linker.

15. The method of claim 6, wherein the tag is covalently bonded to the modified nucleotide.

16. The method of claim 6, wherein the modified nucleotide comprises a β and/or γ phosphate modified nucleotide.

17. The method of claim 6, wherein the modified nucleotide comprises a β phosphate modified nucleotide.

18. The method of claim 6, wherein the modified nucleotide comprises a γ phosphate modified nucleotide.

19. The method of claim 18, wherein the modified nucleotide is selected from the group consisting of Adenosine-5'-(γ-ANS)triphosphate, Guanosine-5'-(γ-ANS) triphosphate, Cytosine-5'-(γ-ANS)triphosphate, Thymidine-5'-(γ-ANS)triphosphate, Adenosine-5'-(γ-4-nitrophenyl) triphosphate, Adenosine-5'-(γ-4-iodonaphthyl), Guanosine-5'-(γ-4-nitrophenyl)triphosphate, triphosphate Adenosine-5'-(γ-6-methylnaphthyl)triphosphate, Cytosine-5'-(γ-4-nitrophenyl)triphosphate, Thymidine-5'-(γ-4-nitrophenyl) triphosphate, Adenosine-5'-(γ-6-methoxynaphthyl) triphosphate, Uracil-5'-(γ-4-nitrophenyl)triphosphate, 3'-azido-3'-deoxythymidine-5'-(γ-4-nitrophenyl)triphosphate, Adenosine-5'-(γ-6-aminonaphthyl)triphosphate, 3'-azido-2',3'-dideoxythymidine-5'-(γ-4-nitrophenyl)triphosphate, Adenosine-5'-(γ-6-nitronaphthyl)triphosphate, 2',3'-didehydro-2',3'-dideoxythymidine-5'-(γ-4-nitrophenyl) triphosphate, Adenosine-5'-(γ-6-chloronaphthyl)triphosphate, Adenosine-5'-(γ-4-aminophenyl)triphosphate, Adenosine-5'-(γ-6-bromonaphthyl)triphosphate, Adenosine-5'-(γ-4-methylphenyl)triphosphate, Adenosine-5'-(γ-6-iodonaphthyl)triphosphate, Adenosine-5'-(γ-4-methoxyphenyl)triphosphate, Adenosine-5'-(γ-4'-hydroxybiphenyl) triphosphate, Adenosine-5-(γ-4-chlorophenyl)triphosphate, Adenosine-5'-(γ-8-quinolyl)triphosphate, Adenosine-5'-(γ-4-bromophenyl)triphosphate, Adenosine-5'-(γ-3-pyridyl) triphosphate, Adenosine-5'-(γ-umbelliferone), Adenosine-5'-(γ-4-iodophenyl)triphosphate, Adenosine-5'-(γ-4-nitronaphthyl) triphosphate, Adenosine-5'-(γ-resorufin) triphosphate, Adenosine-5'-(γ-pyrene)triphosphate, Adenosine-5'-(γ-4-aminonaphthyl)triphosphate, Adenosine-5'-(γ-anthracene)triphosphate, Adenosine-5'-(Γ-6-nitroanthracene)triphosphate, Adenosine-5'-(γ-4-methylnaphthyl) triphosphate, Adenosine-5'-(γ-flavonyl)triphosphate, Adenosine-5'-(γ-4-methoxynaphthyl)triphosphate, Adenosine-5'-(γ-fluorescein)triphosphate, Adenosine-5'-(γ-benzoflavone)triphosphate, Adenosine-5'-(γ-4-chloronaphthyl) triphosphate, Adenosine-5'-(γ-(4-nitrophenyl)-γ'-(4-aminophenyl)triphosphate, Adenosine-5'-(γ-4-bromonaphthyl)triphosphate, Adenosine-5'-(γ-(4-nitrophenyl)-γ'-(4-nitronaphthyl)triphosphate, Adenosine-5'-(γ-methyl)triphosphate, Adenosine-5'-(γ-acetoxypropyl) triphosphate, Guanosine-5'-(γ-methyl)triphosphate, Cytosine-5'-(γ-methyl)triphosphate, Adenosine-5'-(γ-acetoxymethyl)triphosphate(CH3OCCH,—O—NTP), Thymidine-5-(γ-methyl)triphosphate, Uracil-5'-(γ-methyl)triphosphate, Adenosine-5'-(γ-acetoxyethyl)triphosphate, 3'-azido -3'-deoxythymidine-5-(γ-methyl)triphosphate Adenosine-5'-(γ-acetoxybutyl)triphosphate, 3'-azido-2',3'-dideoxythymidine-5'-(γ-methyl)triphosphate, Adenosine-5'-(γ, acetoxypentyl)triphosphate, 2',3'-didehydro-2',3'-dideoxythymidine-5'-(γ-methyl)triphosphate, Adenosine-5'-(γ-acetoxyhexyl)triphosphate, Adenosine-5'-(γ-ethyl) triphosphate, Adenosine-5-(γ-2-nitroethyl)triphosphate, Adenosine-5'-(γ-propyl)triphosphate, Adenosine-5'-(γ-4-butyl)triphosphate, Adenosine-5'-(γ-3-nitropropyl)triphosphate, Adenosine-5'-(γ-hexyl)triphosphate, Adenosine-5'-(γ-octyl)triphosphate, Adenosine-5'-(γ-4-nitrobutyl) triphosphate, Adenosine-5'-(γ-decyl)triphosphate, Adenosine-5'-(γ-dodecyl)triphosphate, Adenosine-5'-(γ-5-nitropentyl)triphosphate, Adenosine-5'-(γ-isopropyl)triphosphate, Adenosine-5'-(γ-tert-butyl)triphosphate, Adenosine-5'-(γ-methyl)-(γ'-ethyl)triphosphate, Adenosine-5'-(γ-cyclohexyl)triphosphate, Adenosine-5'-(γ-methyl)-(γ'-propyl)triphosphate, Adenosine-5'-(γ-2-propenyl) triphosphate, Adenosine-5'-(γ-3-butenyl)triphosphate, Guanosine-5'-(γ-2-propenyl)triphosphate, Adenosine-5'-(γ-4-pentenyl)triphosphate, Cytosine-5-(γ-2-propenyl)triphosphate, Adenosine-5'-(γ-5-hexenyl)triphosphate, Thymidine-5'-(γ-2-propenyl)triphosphate, Adenosine-5'-(γ- cyclohexenyl)triphosphate, Uracil-5'-(7-2-propenyl) triphosphate, Adenosine-5'-(γ-3-propanaldehyde) triphosphate, 3'-azido-3'-deoxythymidine-5'-(γ-2-propenyl) triphosphate, Adenosine-5'-(γ-4-butanaldehyde) triphosphate, 3'-azido-2',3'-dideoxythymidine-5'-(γ-2-propenyl)triphosphate, Adenosine-5'-(γ-3-butanone) triphosphate, 2',3'-didehydro-2',3'-dideoxythymidine-5'-(γ-2-propenyl)triphosphate, Adenosine-5'-(γ-2-propynyl) triphosphate, 3'-azido-2',3'-dideoxythymidine-5'-(γ-2-propynyl)triphosphate, Guanosine-5'-(γ-2-propynyl) triphosphate, Cytosine-5'-(γ-2-propynyl)triphosphate, 2',3'-didehydro-2',3'-dideoxythymidine-5'-(γ-2-propynyl) triphosphate Thymidine 5'-(γ-2-propynyl)triphosphate, Uracil-5'-(γ-2-propynyl)triphosphate, Adenosine-5'-(γ-3-butynyl)triphosphate, 3'-azido-3'-deoxythymidine-5'-(γ-2-propynyl)triphosphate, Adenosine-5'-(γ-4-pentynyl)triphosphate, Adenosine-5'-(γ-5-pentynyl)triphosphate, Adenosine-5'-(γ-4-phenyl)triphosphate, Adenosine-5'-(γ-(4 or 6 or 8 acetoxymethyl naphthyl)triphosphate, Guanosine-5 (γ-4-phenyl)triphosphate, Cytosine-5'-(γ-4-phenyl)triphosphate, Adenosine-5'-(γ-(4-methylpyridyl)triphosphate, Thymidine-5'-(γ-4-phenyl)triphosphate, Uracil-5'-(γ-4-phenyl)triphosphate, Adenosine-5'-(γ-(5-methoxypyridyl)triphosphate, 3'-azido-3'-deoxythymidine-5'-(γ-4-phenyl)triphosphate, Adenosine-5'-(γ-(5-nitropyridyl)triphosphate, 3'-azido-2',3'-dideoxythymidine-5'-(γ-4-phenyl)triphosphate, Adenosine-5'-(γ-(5-acetoxymethylpyridyl)triphosphate, 2',3'-didehydro-2',3'-dideoxythymidine-5'-(γ-4-phenyl)triphosphate, Adenosine-5'-(γ-(6-methyl-1-quinolyl)triphosphate, Adenosine-5'-(γ-4-carboxyphenyl)triphosphate, Adenosine-5'-(γ-(6-methoxy-1-quinolyl)triphosphate, Adenosine-5'-(γ-(4-acetoxymethyl)phenyl)triphosphate, Adenosine-5'-(γ-(4-methyl-1-quinolyl)triphosphate, Adenosine-5'-(γ-4-nitrophenyl)triphosphate, Adenosine-5'-(γ-4-methylphenyl) triphosphate, Adenosine-5'-(γ-(6-nitro-1-quinolyl) triphosphate, Adenosine-5'-(γ-4-methoxyphenyl) triphosphate, Adenosine-5'-(γ-(4-acetoxymethylpyrenyl) triphosphate, Adenosine-5'-(γ-4-ethylphenyl)triphosphate, Adenosine-5'-(γ-(6-methylpyrenyl)triphosphate, Adenosine-5'-(γ-4-butylphenyl)triphosphate, Adenosine 5'-(γ-naphthyl) triphosphate, Adenosine-5'-(γ-(6-ethylpyrenyl)triphosphate, Adenosine-5'-(γ-(4 or 6 or 8 methylnaphthyl)triphosphate, Adenosine-5'-(γ-(6-nitropyrenyl)triphosphate, Adenosine-5'-(γ-(4 or 6 or 8 methoxynaphthyl)triphosphate, Adenosine-5'-(-γ-6-(carboxysuccinimidyl fluorescein)triphosphate, Adenosine-5'-(γ-(4 or 6 or 8 nitro naphthyl)triphosphate. Adenosine-5'-(γ-6-carboxymethyl-2,7-dichlorofluorescein) triphosphate, Adenosine-5'-(γ-(4 or 6 or 8 ethyl naphthyl) triphosphate, Adenosine-5'-(γ-4-phenyl)-(γ'-4 nitrophenyl)triphosphate, Adenosine-5'-(γ-(4 or 6 or 8 butyl naphthyl) triphosphate, Adenosine-5'-(γ-4-phenyl)-(γ-'4 aminophenyl)triphosphate, Adenosine-5'-(γ-methyl)triphosphate, Adenosine-5'-(γ-3-aminopropyl)triphosphate, Guanosine-5'-(γ-methyl)triphosphate, Adenosine-5'-(γ-4-aminobutyl)triphosphate, Cytosine-5'-(γ-methyl)triphosphate Adenosine-5'-(γ-cyclohexyl)triphosphate, Thymidine-5'-(γ-methyl)triphosphate Adenosine-5'-(γ-2-carboxyethyl)triphosphate, Uracil-5'-(γ-methyl)triphosphate, Adenosine-5'-(γ-3-carboxypropyl)triphosphate, 3'-azido-3'-deoxythymidine-5'-(7-methyl)triphosphate, Adenosine-5'-(γ-4'-carboxybutyl) triphosphate, 3'-azido-2',3'-dideoxythymidine-5'-(γ-methyl) triphosphate, Adenosine-5'-(γ-2-hydroxyethyl)triphosphate, 2',3'-didehydro-2',3'-dideoxythymidine-5'-(γ-methyl)triphosphate, Adenosine-5'-(γ-3-hydroxypropyl)triphosphate, Adenosine-5'-(γ-ethyl)triphosphate, Adenosine-5'-(γ-propyl)triphosphate, Adenosine-5'-(γ-4-hydroxybutyl)triphosphate, Adenosine-5'-(γ-4-butyl)triphosphate, Adenosine-5'-(γ-2-nitroethyl)triphosphate, Adenosine-5'-(γ-hexyl) triphosphate, Adenosine-5'-(γ-3-nitropropyl)triphosphate, Adenosine-5'-(γ-isopropyl)triphosphate, Adenosine-5'-(γ-4-nitrobutyl)triphosphate, Adenosine-5'-(γ-tert-butyl)triphosphate, Adenosine-5'-(γ-methyl)-(γ'-ethyl)triphosphate, Adenosine-5'-(γ-cyclohexyl)triphosphate, Adenosine-5'-(γ-2-aminoethyl)triphosphate, and Adenosine-5'-(γ-methyl)-(γ'-propyl)triphosphate.

20. The method of claim 1, wherein the polymerizing agent is selected from the group consisting of naturally occurring or synthetic polymerases and reverse transcriptases.

21. The method of claim 6, wherein the polymerizing agent is selected from the group consisting of naturally occurring or synthetic polymerases and reverse transcriptases.

22. The kit of claim 7, wherein the tag is covalently bonded to the modified nucleotide through a linker.

23. The kit of claim 7, wherein the tag is covalently bonded to the modified nucleotide.

24. The kit of claim 7, wherein the modified nucleotide comprises a β and/or γ phosphate modified nucleotide.

25. The kit of claim 7, wherein the modified nucleotide comprises a β phosphate modified nucleotide.

26. The kit of claim 7, wherein the modified nucleotide comprises a γ phosphate modified nucleotide.

27. The kit of claim 23, wherein the molecular tag comprises a fluorophore selected from the group consisting of 4-acetamido-4'-isothiocyanatostilbene-2,2'disulfonic acid; acridine and derivatives: acridine, acridine isothiocyanate; 5-(2'-aminoethyl) aminonaphthalene-1-sulfonic acid (EDANS); 4-amino-3-vinylsulfonyl)phenyl]naphthalimide-3,5disulfonate; -(4-anilino-lnaphthyl) maleimide; anthranilamide; BODIPY; Brilliant Yellow; coumarin and derivatives: coumarin, 7-amino-4-methylcoumarin (AMC, Coumarin 120), 7-amino-4trifluoromethylcouluarin (Coumaran 151); cyanine dyes; cyanosine; 4',6-diaminidino-2phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'diisothiocyanatostilbene-2,2'-disulfonic acid; 5-dimethylamino naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5carboxyfluorescein (FAM), 5-(4,6-dichlorotriazin-2-yl) aminofluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

28. The kit of claim 23, wherein the molecular tag is selected from the group consisting of alkyl groups having between 1 and 30 carbon atoms, aryl groups having between about 6 and about 40 carbon atoms, or alkaryl and aralkyl groups having between about 7 and about 40 carbon atoms, or mixture or combinations thereof, where the carbon atoms are replace by one or more hetero atoms in the structure provided the structure represents a stable molecular system, where the hetero atoms selected from the group consisting of P, S, Si, N, and O.

29. The kit of claim 23, wherein the molecular tag is selected from the group consisting of 4-aminophenol, 6-aminonaphthol, 4-nitrophenol, 6-nitronaphthol, 4-methylphenol, 6-chloronaphthol, 4-methoxyphenol, 6-bromonaphthol, 4-chlorophenol, 6-iodonaphthol, 4-bromophenol, 4,4'-dihydroxybiphenyl, 4-iodophenol, 8-hydroxyquinoline, 4-nitronaphthol, 3-hydroxypyridine, 4-aminonaphthol, umbelliferone, 4-methylnaphthol, resorufin, 4-methoxynaphthol, 8-hydroxypyrene, 4-chloronaphthol, 9-hydroxyanthracene, 4-bromonaphthol, 6-nitro-9-hydroxyanthracene, 4-iodonaphthol, 3-hydroxyflavone, 6-methylnaphthol, fluorescein, 6-methoxynaphthol, 3-hydroxybenzoflavone, 1-hydroxy-2-propyne, 1-hydroxy-4-pentyne, 1-hydroxy-3-butyne, 1-hydroxy-5-hexyne, Methanol, Ethanol, Propanol, Isopropanol, Butanol, Tert-butanol, Hexanol, Cyclohexanol, Heptanol, Octanol, Decanol, Undecanol, Dodecanol, 1-acetoxymethanol (CH3OOCCH2-O—NTP), 2-acetoxyethanol, 3-acetoxypropanol, 4-acetoxybutanol, 5-acetoxypentanol, 6-acetoxyhexanol, 2-nitroethanol, 3-nitropropanol, 4-nitrobutanol, 5-nitropentanol, 5-nitrohexanol, 1-hydroxy-3-propene, 1-hydroxy-2-cyclohexene, 1-hydroxy-4-butene, 1-hydroxy-3-propaldehyde, 1-hydroxy-5-pentene, 1-hydroxy-4-butanaldehyde, 1-hydroxy-6-hexene, 1-hydroxy-3-Butanone, Phenol, 4-methyl-3-hydroxypyridine, 4-Carboxyphenol, 5-methoxy-3-hydroxypyridine, 4-Acetoxymethylphenol, 5-nitro-3-hydroxypyridine, 4-nitrophenol, 5-acetoxymethyl-3-hydroxypyridine, 4-methylphenol, 6-methyl-8-hydroxyquinoline, 4-methoxyphenol 6-methoxy-8-hydroxyquinoline, 4-ethylphenol, 4-methyl-8-hydroxyquinoline, 4-butylphenol, 6-nitro-8-hydroxyquinoline, naphthol, 4-acetoxymethyl-8-hydroxyquinoline, 4 or 6 or 8 methylnaphthol pyrene, 4 or 6 or 8 methoxynaphthol, 6-methyl-8-hydroxypyrene, 4 or 6 or 8 nitronaphthol, 6-ethyl-8-hydroxypyrene, 4 or 6 or 8 ethylnaphthol, 6-nitro-8-hydroxypyrene, 4 or 6or 8 butylnaphthol 6-(carboxysuccinimidylester) fluorescein, 4 or 6 or 8 acetoxymethylnaphthol, 6-carboxymethyl-2,7-dichlorofluorescein, Methanol Cyclohexanol, 2-carboxy ethanol, 3-carboxypropanol, 4-carboxybutanol, 2-hydroxyethanol, 3-hydroxypropanol, 4-hydroxybutanol, 2-aminoethanol, 2-nitroethanol, 3-aminopropanol, 3-nitropropanol, 4-aminobutanol, and 4-nitrobutanol.

30. The kit of claim 26, wherein the modified nucleotide is selected from the group consisting of Adenosine-5'-(γ-ANS)triphosphate, Guanosine-5'-(γ-ANS)triphosphate, Cytosine-5'-(γ-ANS)triphosphate, Thymidine-5'-(γ-ANS) triphosphate, Adenosine-5'-(γ-4-nitrophenyl)triphosphate, Adenosine-5'-(γ-4-iodonaphthyl), Guanosine-5'-(γ-4-nitrophenyl)triphosphate, triphosphate Adenosine-5'-(γ-6-methylnaphthyl)triphosphate, Cytosine-5'-(γ-4-nitrophenyl)triphosphate, Thymidine-5'-(γ-4nitrophenyl)triphosphate, Adenosine-5'(γ-6-methoxynaphthyl)triphosphate, Uracil-5'-(γ-4-nitrophenyl)triphosphate, 3'-azido -3'-deoxythymidine-5'-(γ-4-nitrophenyl)triphosphate, Adenosine-5'-(γ-6-aminonaphthyl)triphosphate, 3'-azido-2',3'-dideoxythymidine-5'-(γ-4-nitrophenyl)triphosphate, Adenosine-5'-(γ-6-nitronaphthyl)triphosphate, 2',3'-didehydro-2',3'-dideoxythymidine-5'-(γ-4-nitrophenyl)triphosphate, Adenosine-5'-(γ-6-chloronaphthyl)triphosphate, Adenosine-5'-(γ-4-aminophenyl)triphosphate, Adenosine-5'-(γ-6-bromonaphthyl)triphosphate, Adenosine-5'-(γ-4-methylphenyl)triphosphate, Adenosine-5'-(γ-6-iodonaphthyl)triphosphate, Adenosine-5'-(γ-4-methoxyphenyl)triphosphate, Adenosine-5'-(γ-4'-hydroxybiphenyl)triphosphate, Adenosine-5'-(γ-4-chlorophenyl)triphosphate, Adenosine-5'-(γ-8-quinolyl) triphosphate, Adenosine-5'-(γ-4-bromophenyl)triphosphate, Adenosine-5'-(γ-3-pyridyl)triphosphate, Adenosine-5'-(γ-umbelliferone), Adenosine-5'-(γ-4-iodophenyl)triphosphate, Adenosine-5'-(γ4-nitronaphthyl)triphosphate, Adenosine-5'-(γ-resorufin)triphosphate, Adenosine-5'-(γ-pyrene)triphosphate, Adenosine-5'-(γ-4-aminonaphthyl)triphosphate, Adenosine-5'-(γ-anthracene)triphosphate, Adenosine-5-(Γ-6-nitroanthracene)triphosphate, Adenosine-5'-(γ4-methylnaphthyl)triphosphate, Adenosine-5'-(γ-flavonyl) triphosphate, Adenosine-5'-(γ-4-methoxynaphthyl)triphosphate, Adenosine-5'-(γ-fluorescein)triphosphate, Adenosine-5'-(γ-benzoflavone)triphosphate, Adenosine-5'-(γ-4-chloronaphthyl)triphosphate, Adenosine-5'-(γ-(4-nitrophenyl)-γ'-(4-aminophenyl)triphosphate, Adenosine-5'-(γ-4-bromonaphthyl)triphosphate, Adenosine-5'-(γ-(4-nitrophenyl)-γ'-(4-nitronaphthyl)triphosphate, Adenosine-5'-(γ-methyl)triphosphate, Adenosine-5'-(γ-acetoxypropyl) triphosphate, Guanosine-5'-(γ-methyl)triphosphate, Cytosine-5'-(γ-methyl)triphosphate, Adenosine-5'-(γ-acetoxymethyl)triphosphate (CH3OOCCH,—O—NTP), Thymidine-5'-(γ-methyl)triphosphate, Uracil5-(65 -methyl) triphosphate, Adenosine-5'-(γ-acetoxyethyl)triphosphate, 3'-azido-3'-deoxythymidine-5-(γ-methyl)triphosphate, Adenosine-5'-(γ-acetoxybutyl)triphosphate, 3'-azido-2',3'-dideoxythymidine-5'-(γ-methyl)triphosphate, Adenosine-5' (γ, acetoxypentyl)triphosphate, 2',3'-didehydro-2',3'-dideoxythymidine-5'-(γ-methyl)triphosphate, Adenosine-5'-(γ-acetoxyhexyl)triphosphate, Adenosine-5'-(γ-ethyl) triphosphate, Adenosine-5'-(γ-2-nitroethyl)triphosphate, Adenosine-5'-(γ-propyl)triphosphate, Adenosine-5'-(γ-4-butyl)triphosphate, Adenosine-5'-(γ-3-nitropropyl)triphosphate, Adenosine-5'-(γ-hexyl)triphosphate, Adenosine-5'-(γ-octyl)triphosphate, Adenosine-5'-(γ-4-nitrobutyl) triphosphate, Adenosine-5'-(γ-decyl)triphosphate, Adenosine-5'-(γ-dodecyl)triphosphate, Adenosine-5'-(γ-5-nitropentyl)triphosphate, Adenosine-5'-(γ-isopropyl)triphosphate, Adenosine-5'-(γ-tert-butyl)triphosphate, Adenosine-5'-(γ-methyl)-(γ'-ethyl)triphosphate, Adenosine-5'-(γcyclohexyl)triphosphate, Adenosine-5'-(γ-methyl)-(γ'-propyl)triphosphate, Adenosine-5'-(γ-2-propenyl) triphosphate, Adenosine-5'-(γ-3-butenyl)triphosphate, Guanosine-5'-(γ-2-propenyl)triphosphate, Adenosine-5'-(γ-4-pentenyl)triphosphate, Cytosine-5'-(γ-2-propenyl)triphosphate, Adenosine-5 '-(γ-5-hexenyl)triphosphate, Thymidine-5'-(γ-2-propenyl)triphosphate, Adenosine-5'-(γ-cyclohexenyl)triphosphate, Uracil-5'-(7-2-propenyl) triphosphate, Adenosine-5'-(γ-3-propanaldehyde) triphosphate, 3'-azido-3'-deoxythymidine-5'-(γ-2-propenyl) triphosphate, Adenosine-5'-(γ-4-butanaldehyde) triphosphate, 3'-azido-2',3'-dideoxythymidine-5'-(γ-2-propenyl)triphosphate, Adenosine-5'-(γ-3-butanone) triphosphate, 2',3'-didehydro-2',3'-dideoxythymidine-5'-(γ-2-propenyl)triphosphate, Adenosine-5'-(γ-2-propynyl) triphosphate, 3'-azido-2',3'-dideoxythymidine-5'-(γ-2-propynyl)triphosphate, Guanosine-5'-(γ-2-propynyl) triphosphate, Cytosine-5'-(γ-2-propynyl)triphosphate, 2',3'-didehydro-2',3'-dideoxythymidine-5'-(γ-2-propynyl)

triphosphate Thymidine 5'-(γ-2-propynyl)triphosphate, Uracil-5'-(γ-2-propynyl)triphosphate, Adenosine-5'-(γ-3-butynyl)triphosphate, 3'-azido-3'-deoxythymidine-5'-(γ-2-propynyl)triphosphate, Adenosine-5'-(γ-4-pentynyl)triphosphate, Adenosine-5'-(γ-5-pentynyl)triphosphate, Adenosine-5-(γ-4-phenyl)triphosphate, Adenosine-5'-(γ-(4 or 6 or 8 acetoxymethyl naphthyl)triphosphate, Guanosine-5'-(γ-4phenyl)triphosphate, Cytosine-5'-(γ-4-phenyl)triphosphate, Adenosine-5'-(γ-(4-methylpyridyl)triphosphate, Thymidine-5'-(γ-4-phenyl)triphosphate, Uracil-5'-(γ-4-phenyl) triphosphate, Adenosine-5'-(γ-(5-methoxypyridyl) triphosphate, 3'-azido-3'-deoxythymidine-5'-(γ-4-phenyl) triphosphate, Adenosine -5'-(γ-(5-nitropyridyl)triphosphate, 3'-azido-2',3'-dideoxythymidine-5'-(γ-4-phenyl)triphosphate, Adenosine-5'-(γ-(5-acetoxymethylpyridyl)triphosphate, 2',3'-didehydro-2',3'-dideoxythymidine-5'-(γ-4-phenyl)triphosphate, Adenosine-5'-(γ-(6-methyl-1-quinolyl) triphosphate, Adenosine-5'-(γ-4-carboxyphenyl) triphosphate, Adenosine-5'-(γ-(6-methoxy-1-quinolyl) triphosphate, Adenosine-5'-(γ-(4-acetoxymethyl) phenyl) triphosphate, Adenosine-5'-(γ-(4-methyl-1-quinolyl) triphosphate, Adenosine-5'-(γ-(4-nitrophenyl)triphosphate, Adenosine-5'-(γ-4-methylphenyl)triphosphate, Adenosine-5'-(γ-(6-nitro-1-quinolyl)triphosphate, Adenosine-5'-(γ-4-methoxyphenyl)triphosphate, Adenosine-5'-(γ-(4-acetoxymethylpyrenyl)triphosphate, Adenosine-5'-(γ-4-ethylphenyl) triphosphate, Adenosine-5'-(γ-(6-methylpyrenyl) triphosphate, Adenosine-5'-(γ-4-butylphenyl)triphosphate, Adenosine 5'-(γ-naphthyl)triphosphate, Adenosine-5'-(γ-(6-ethylpyrenyl)triphosphate, Adenosine-5'-(γ-(4 or 6 or 8 methyl naphthyl)triphosphate, Adenosine-5'-(γ-(6-nitropyrenyl)triphosphate, Adenosine-5'-(γ-(4 or 6 or 8 methoxynaphthyl)triphosphate, Adenosine-5'-(γ-6-(carboxysuccinimidyl fluorescein)triphosphate, Adenosine-5'-(γ-(4 or 6 or 8 nitro naphthyl)triphosphate. Adenosine-5'-(γ-6-carboxymethyl-2,7-dichlorofluorescein)triphosphate, Adenosine-5'-(γ-(4 or 6 or 8 ethyl naphthyl)triphosphate, Adenosine-5'-(γ-4-phenyl)-(γ'-4 nitrophenyl)triphosphate, Adenosine-5'-(γ-(4 or 6 or 8 butyl naphthyl)triphosphate, Adenosine-5'-(γ-4-phenyl)-(γ'-4 aminophenyl)triphosphate, Adenosine-5'-(γ-methyl)triphosphate, Adenosine-5-(γ-3-aminopropyl) triphosphate, Guanosine-5'-(γ-methyl)triphosphate, Adenosine-5'-(γ-4-aminobutyl)triphosphate, Cytosine-5'-(γ-methyl)triphosphate Adenosine-5'-(γ-cyclohexyl)triphosphate, Thymidine-5'-(γ-methyl)triphosphate Adenosine-5'-(γ-2-carboxyethyl)triphosphate, Uracil-5'-(γ-methyl) triphosphate, Adenosine-5'-(γ-3-carboxypropyl) triphosphate, 3'-azido-3'-deoxythymidine-5'-(7-methyl) triphosphate, Adenosine-5'-(γ-4-carboxybutyl)triphosphate, 3'-azido-2',3'-dideoxythymidine-5'-(γ-methyl)triphosphate, Adenosine-5'-(γ-2-hydroxyethyl)triphosphate, 2',3'-didehydro-2',3'-dideoxythymidine-5'-(γ-methyl)triphosphate, Adenosine-5'-(γ-3-hydroxypropyl)triphosphate, Adenosine-5'-(γ-ethyl)triphosphate, Adenosine-5'-(γ-propyl)triphosphate, Adenosine-5'-(γ-4-hydroxybutyl)triphosphate, Adenosine-5'-(γ-4-butyl)triphosphate, Adenosine-5'-(γ-2-nitroethyl)triphosphate, Adenosine-5'-(γ-hexyl)triphosphate, Adenosine-5'-(γ-3-nitropropyl)triphosphate, Adenosine-5'-(γ-isopropyl)triphosphate, Adenosine-5'-(γ-4-nitrobutyl) triphosphate, Adenosine-5'-(γ-tert-butyl)triphosphate, Adenosine-5'-(γ-methyl)-(γ'-ethyl)triphosphate, Adenosine-5'-(γ-cyclohexyl)triphosphate, Adenosine-5'-(γ-2-aminoethyl)triphosphate, and Adenosine-5'-(γ-methyl)-(γ'-propyl) triphosphate.

31. The kit of claim 7, wherein the polymerizing agent is selected from the group consisting of naturally occurring or synthetic polymerases and reverse transcriptases.

* * * * *